(12) United States Patent
Hirabayashi

(10) Patent No.: US 9,561,012 B2
(45) Date of Patent: Feb. 7, 2017

(54) METHOD OF DECIDING RISK OF OBSTRUCTIVE SLEEP APNEA SYNDROME, METHOD OF DECIDING SINKING OF HYOID BONE, PROGRAMS, X-RAY DIAGNOSTIC SYSTEM, AND METHOD OF MAKING ORAL APPLIANCE

(71) Applicant: CEPHMEDICAL CORPORATION, Nagano (JP)

(72) Inventor: Daiki Hirabayashi, Nagano (JP)

(73) Assignee: Cephmedical Corporation, Nagano (JP)

( * ) Notice: Subject to any disclaimer, the term of this patent is extended or adjusted under 35 U.S.C. 154(b) by 0 days.

(21) Appl. No.: 14/651,792

(22) PCT Filed: Dec. 13, 2013

(86) PCT No.: PCT/JP2013/083446
§ 371 (c)(1),
(2) Date: Jun. 12, 2015

(87) PCT Pub. No.: WO2014/097982
PCT Pub. Date: Jun. 26, 2014

(65) Prior Publication Data
US 2015/0320379 A1    Nov. 12, 2015

(30) Foreign Application Priority Data

Dec. 17, 2012 (JP) .................................. 2012-274274
Feb. 1, 2013 (JP) .................................. 2013-018055
(Continued)

(51) Int. Cl.
*A61B 6/00* (2006.01)
*A61B 6/04* (2006.01)
(Continued)

(52) U.S. Cl.
CPC ................ *A61B 6/505* (2013.01); *A61B 6/50* (2013.01); *A61B 6/5205* (2013.01);
(Continued)

(58) Field of Classification Search
None
See application file for complete search history.

(56) References Cited

U.S. PATENT DOCUMENTS 9,153,022 B2 * 10/2015 Finkelstein et al. . A61B 5/1075

OTHER PUBLICATIONS

Albajalan, Osama B., A. R. Samsudin, and Rozita Hassan. "Craniofacial morphology of Malay patients with obstructive sleep apnoea." The European Journal of Orthodontics 33, No. 5 (2011): 509-514.*

(Continued)

*Primary Examiner* — Michelle Hausmann
(74) *Attorney, Agent, or Firm* — K&L Gates LLP

(57) ABSTRACT

Provided are a method of deciding the risk of obstructive sleep apnea syndrome capable of deciding the risk of a subject to become obstructive sleep apnea syndrome objectively and easily in a short time, its program and an X-ray diagnostic system having the program.

The method includes detecting at least the hyoid bone, sella S, gonion Go and menton Me by lateral head and neck radiography of the subject; and deciding whether the center of the body or the whole of the body of the detected hyoid bone is included in an area above a perpendicular drawn toward the extended line of the segment S-Go from Me or not.

10 Claims, 109 Drawing Sheets

(30) Foreign Application Priority Data

Mar. 18, 2013 (JP) ................................. 2013-054708
Jul. 8, 2013 (JP) ................................. 2013-142467

(51) Int. Cl.
*A61B 6/10* (2006.01)
*A61B 5/00* (2006.01)
*G06F 19/00* (2011.01)

(52) U.S. Cl.
CPC .......... *A61B 6/5217* (2013.01); *A61B 5/4818* (2013.01); *A61B 6/04* (2013.01); *A61B 6/107* (2013.01); *A61B 6/501* (2013.01); *G06F 19/3431* (2013.01)

(56) References Cited

OTHER PUBLICATIONS

Deberry-Borowiecki, Bernard, Andrzej Kukwa, and Robert HI Blanks. "Cephalometric analysis for diagnosis and treatment of obstructive sleep apnea." The Laryngoscope 98, No. 2 (1988): 226-234.*
Kawashima, Shigeto, Timo Peltomäki, Juhani Laine, and Olli Rönning. "Cephalometric evaluation of facial types in preschool children without sleep-related breathing disorder." International journal of pediatric otorhinolaryngology 63, No. 2 (2002): 119-127.*
Battagel, J. M., A. Johal, P. R. L'estrange, C. B. Croft, and B. Kotecha. "Changes in airway and hyoid position in response to mandibular protrusion in subjects with obstructive sleep apnoea (OSA)." The European Journal of Orthodontics 21, No. 4 (1999): 363-376.*
Vieira, Bruno B., Carla E. Itikawa, Leila A. de Almeida, Heidi S. Sander, Regina MF Fernandes, Wilma T. Anselmo-Lima, and Fabiana CP Valera. "Cephalometric evaluation of facial pattern and hyoid bone position in children with obstructive sleep apnea syndrome." International journal of pediatric otorhinolaryngology 75, No. 3 (2011): 383-386.*
Lowe, Alan A., M. Murat Özbek, Keisuke Miyamoto, Eung-Kwon Pae, and John A. Fleetham. "Cephalometric and demographic characteristics of obstructive sleep apnea: an evaluation with partial least squares analysis." The Angle orthodontist 67, No. 2 (1997): 143-154.*
Lin, Yen-Chun, Hsiang-Chien Lin, and Hung-Huey Tsai. "Changes in the pharyngeal airway and position of the hyoid bone after treatment with a modified bionator in growing patients with retrognathia." Journal of Experimental & Clinical Medicine 3.2 (2011): 93-98.*
Khanna, Rohit, Tripti Tikku, and V. P. Sharma. "Position and orientation of hyoid bone in class II división 1 subjects: A cephalometric study." J Indian Orthod Soc 45 (2011): 212-8.*
Bibby, R. E., and C. B. Preston. "The hyoid triangle." American journal of orthodontics 80.1 (1981): 92-97.*
Lee, R. W., et al. "Craniofacial phenotyping in obstructive sleep apnea—a novel quantitative photographic approach." Sleep 32.1 (2009): 37-45.*
International Search Report issued in connection with International Patent Application No. PCT/JP2013/083446, dated Mar. 11, 2014. (8 pages).
Notification of Reason(s) for Refusal issued in connection with Japanese Patent Application No. 2013-018211, dated Mar. 12, 2013. (5 pages).
Sonsuwan Nuntigar et al., The relationships between cephalometric parameters and severity of obstructive sleep apnea, Auris Nasus Larynx, Feb. 2011, vol. 38 No. 1, pp. 83-87.
Toshitaka Muto et al., "Utility of Cephalogram in Diagnostic Tool of Obstructive Sleep Apnea Syndrome—Cephalometric Study on Relationship between Pharyngeal Airway Space and Craniofacial Morphology-", Kenko Kanri Jigyodan Kenkyu Josei Ronbunshu, Oct. 30, 2004 (Oct. 30, 2004), vol. 20, pp. 27-34. (Also cited in International Search Report issued in connection with related International Patent Application No. PCT/JP2013/083446, dated Mar. 11, 2014).
Haruto Katahira et al., "The effect of tongue position to oral appliance treatment in patients with snore symptom", Tsurumi University dental journal, May 10, 2005 (May 10, 2005), vol. 31, No. 2, pp. 111-117. (Also cited in International Search Report issued in connection with related International Patent Application No. PCT/JP2013/083446, dated Mar. 11, 2014).
Edited by workshop of sleep respiratory disorder "Guideline for diagnosis and treatment of sleep apnea syndrome of adults", pp. 15-16, p. 25(Medical Review Corporation, published in Jul. 2005) (Also cited in the presently pending U.S. Appl. No. 14/651,792 at paragraphs [0003] to [0005]).

* cited by examiner

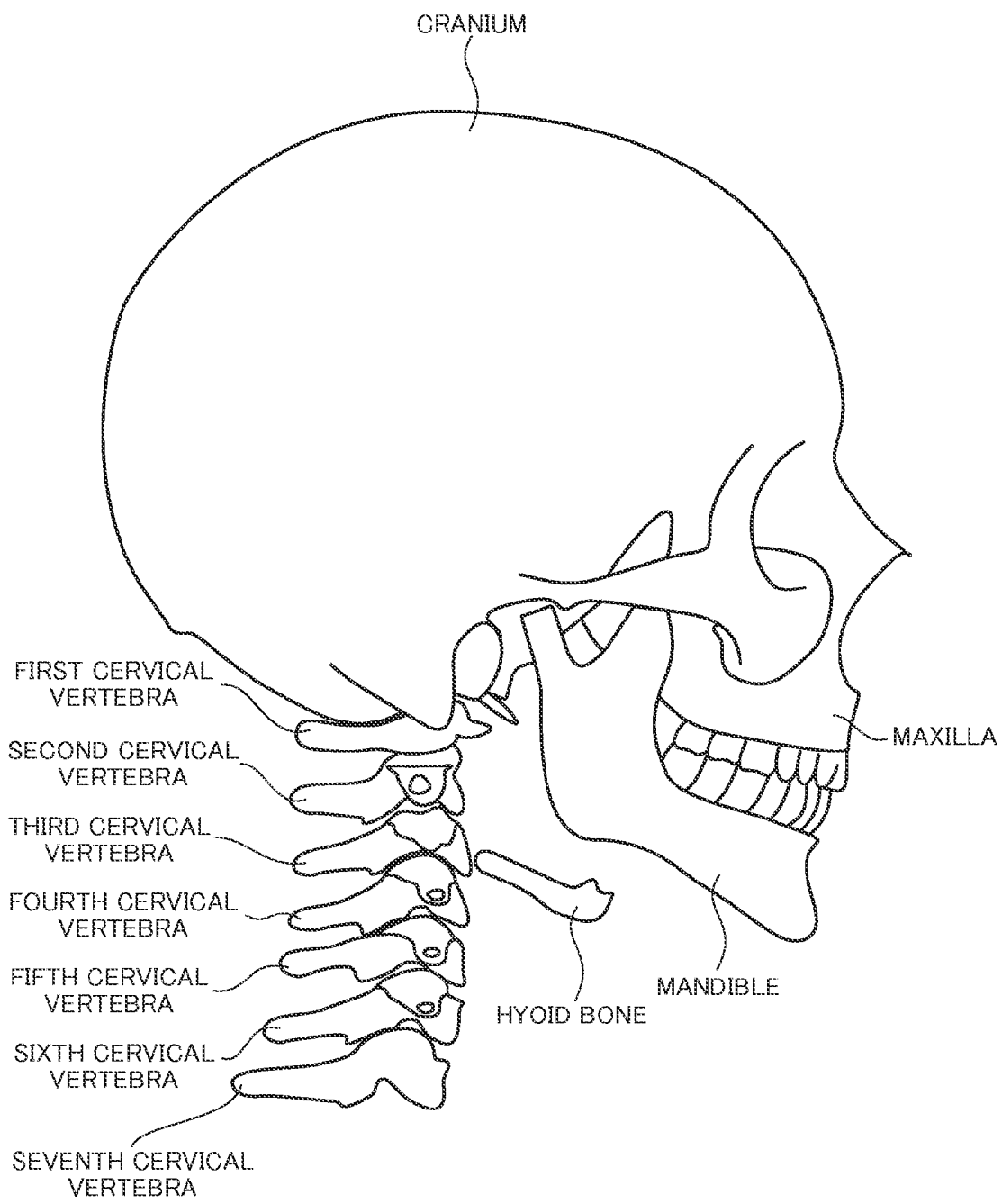

METHOD OF DECIDING RISK OF OBSTRUCTIVE SLEEP APNEA SYNDROME, METHOD OF DECIDING SINKING OF HYOID BONE, PROGRAMS, X-RAY DIAGNOSTIC SYSTEM, AND METHOD OF MAKING ORAL APPLIANCE

CROSS REFERENCES TO RELATED APPLICATIONS

The present application is a national stage of International Application No. PCT/JP2013/083446 filed on Dec. 13, 2013 and claims priority to Japanese Patent Application No. 2012-274274 filed on Dec. 17, 2012, Japanese Patent Application No. 2013-018055 filed on Feb. 1, 2013, Japanese Patent Application No. 2013-054708 filed on Mar. 18, 2013, and Japanese Patent Application No. 2013-142467 filed on Jul. 8, 2013, the disclosure of which is incorporated herein by reference.

BACKGROUND

The present invention relates to a method of deciding the risk of obstructive sleep apnea syndrome, a method of deciding sinking of the hyoid bone, programs, an X-ray diagnostic system and a method of making an oral appliance, which are preferably applied to decide the risk of a subject to become obstructive sleep apnea syndrome, or to decide the presence or absence or the degree of sinking of the hyoid bone, or to make an oral appliance for treatment of obstructive sleep apnea syndrome based on the result of decision.

BACKGROUND ART

Obstructive sleep apnea syndrome (OSAS) is a disease in which the upper respiratory tract of a patient is obstructed during sleep and respiration stops. It is known that obstructive sleep apnea syndrome leads to aggravation of life prognosis through a rise in blood pressure, complications from arrhythmia, acceleration of arteriosclerosis, etc. due to marked decrease of arterial oxygen saturation ($SaO_2$) etc. Obstructive sleep apnea syndrome results in wakefulness and excessive daytime sleepiness (EDS) due to midway arousal reaction associated with apnea. On the other hand, obstructive sleep apnea syndrome not only lowers working efficiency due to disorder of attention, recognition, memory, etc. but also becomes the cause of traffic accidents, industrial accidents, etc. Therefore, obstructive sleep apnea syndrome becomes a serious social problem.

Conventionally, for example, diagnosis of obstructive sleep apnea syndrome is carried out as follows (for example, see non-patent literature 1). That is, for a patient diagnosed by a medical institution, if two or more among EDS, a feeling of suffocation, a gasp and repeating awakening during sleep, lack of feeling fine at the time of rising, a feeling of fatigue in the daytime and lack of power of concentration are recognized, polysomnography (PSG) is carried out. As a result, when an apnea and hypopnea index (AHI)≥5 and a large majority of apnea is obstructive apnea, diagnosis as obstructive sleep apnea syndrome is decided. If AHI<5, development is observed. On the other hand, if two or more among EDS, a feeling of suffocation, a gasp and repeating awakening during sleep, lack of feeling fine at the time of rising, a feeling of fatigue in the daytime and lack of power of concentration are not recognized, an examination by a simple diagnostic device is carried out. The simple diagnostic device is an examination system for simultaneously recording air flow through nares, breathing movement of the chest or abdomen, tracheal sounds, percutaneous oxygen saturation of arterial blood ($SpO_2$), etc. and thereafter carrying out automatic analysis. If AHI≥5 as a result of the examination by the simple diagnostic device, multiple sleep latency test (MSLT) is carried out. As a result, if sleep disorder is found, PSG is carried out. If sleep disorder is not found, development is observed. As a result of the examination by the simple diagnostic device, if AHI<5, development is observed.

On the other hand, not infrequently, obstructive sleep apnea syndrome is accompanied by morphological abnormity of the upper respiratory tract. Therefore, observation of the upper respiratory tract by visual examination, upper respiratory tract endoscope, etc. is indispensable to diagnose obstructive sleep apnea syndrome and it is considered that more objective morphological evaluation of the upper respiratory tract is possible by carrying out cephalometry etc. (for example, see non-patent literature 1). More specifically, described in non-patent literature 1 are extension of the distance between the mandibular plane and the hyoid bone (height of the hyoid bone)(lower part of the hyoid bone), extension of the length of the soft palate, reduction of the degree of projection of the apical base of the mandible, etc. as features of patients of obstructive sleep apnea syndrome.

PRIOR ART LITERATURE

Non-Patent Literature

[NON-PATENT LITERATURE 1] Edited by workshop of sleep respiratory disorder"Guideline for diagnosis and treatment of sleep apnea syndrome of adults", pp. 15-16, p. 25 (Medical Review Corporation, published in July, 2005)

SUMMARY

Subjects to be Solved by Invention

However, for PSG, one must enter the hospital and be subjected to examination over night, so PSG has drawbacks that it not only takes a long time to diagnose but also gives patients serious mental and physical burden. In addition, it is difficult for a simple diagnostic device to diagnose correctly. Furthermore, the effectiveness of morphological evaluation of the upper respiratory tract by cephalometry is unknown. On the other hand, if the risk of a subject to become obstructive sleep apnea syndrome is easily known, it is possible to take measures to reduce the risk to stop becoming obstructive sleep apnea syndrome. However, heretofore, no effective method of deciding the risk has been proposed.

Therefore, a subject to be solved by the present invention is to provide a method of deciding the risk of obstructive sleep apnea syndrome capable of deciding the risk of a subject to become obstructive sleep apnea syndrome objectively and easily in a short time, its program, an X-ray diagnostic system having the program and a method of making an oral appliance capable of making easily an effective oral appliance for treatment of obstructive sleep apnea syndrome based on the result of decision of the risk of obstructive sleep apnea syndrome.

Another subject to be solved by the present invention is to provide a method of deciding sinking of the hyoid bone capable of deciding the presence or absence or the degree of sinking of the hyoid bone of a subject objectively and easily in a short time, its program, an X-ray diagnostic system having the program and a method of making an oral appliance capable of making easily an effective oral appliance for treatment of sinking of the hyoid bone based on the result of decision of sinking of the hyoid bone.

The above subjects and the other subjects will be apparent from the following description of the present description.

Means for Solving the Subjects

In the process of earnest study to solve the subjects, the inventor of the present invention analyzed the position of the hyoid bone, especially the position of the body of the hyoid bone in lateral head and neck radiographs taken for patients diagnosed as obstructive sleep apnea syndrome and subjects without respiratory disorder and found that the position of the center of the body of the hyoid bone was definitely different between the two parties. Furthermore, when posteroanterior head and neck radiographs or anteroposterior head and neck radiographs of patients diagnosed as obstructive sleep apnea syndrome were taken, the hyoid bone, that is not observed for patients without respiratory disorder because it overlaps with the mandible etc., was definitely observed. Based on this observation, the inventor found that it is possible to decide the risk of a patient to become obstructive sleep apnea syndrome easily by deciding that when a posteroanterior head and neck radiograph or an anteroposterior head and neck radiograph of the patient is taken, the hyoid bone was observed in the image or not. The present invention has been worked out as the results of the earnest study based on the knowledge that the inventor obtained.

That is, to solve the above subjects, according to the invention, there is provided a method of deciding the risk of obstructive sleep apnea syndrome, comprising:

using at least the hyoid bone, sella S, gonion Go and menton Me which are detected by lateral head and neck radiography of a subject and deciding whether the detected center of the body of the hyoid bone is included in an area above a perpendicular drawn toward the extended line of the segment S-Go from Me or not.

The method of deciding the risk of obstructive sleep apnea syndrome is specifically carried out by a computer having a program comprising the above step. Typically, the method of deciding the risk of obstructive sleep apnea syndrome comprises: the first step of detecting at least the hyoid bone, sella S, gonion Go and menton Me by lateral head and neck radiography of the subject; and the second step of deciding whether the detected center of the body of the hyoid bone is included in the area above the perpendicular drawn toward the extended line of the segment S-Go from Me or not. More specifically, in this case, the method of deciding the risk of obstructive sleep apnea syndrome is carried out by a computer having a program comprising the first step and the second step. According to the method of deciding the risk of obstructive sleep apnea syndrome, when the center of the body of the hyoid bone is included in the area above the perpendicular drawn toward the extended line of the segment S-Go from Me, it can be decided that there is no risk of obstructive sleep apnea syndrome, and when it is not included in the area, in other words, when it is included in an area below the perpendicular drawn toward the extended line of the segment S-Go from Me, it can be decided that there is the risk of obstructive sleep apnea syndrome. Preferably, in the second step, it is decided whether the detected center of the body of the hyoid bone is included in the first triangle formed by the extended line of the segment S-Go, the perpendicular drawn toward the extended line of the segment S-Go from Me and the segment Go-Me or not. In this case, when the center of the body of the hyoid bone is included in the inside of the first triangle, it can be decided that there is no risk of obstructive sleep apnea syndrome, and when it locates in an area below the first triangle, it can be decided that there is the risk of obstructive sleep apnea syndrome. According to the method of deciding the risk of obstructive sleep apnea syndrome, as needed, in the first step, condylion Cd is further detected by lateral head and neck radiography of the subject, and in the second step, it is decided that which area of the inside of the first triangle, the inside of the second triangle formed by the extended line of the segment Cd-Go, a perpendicular drawn toward the extended line of the segment Cd-Go from Me and a perpendicular drawn toward the extended line of the segment S-Go from Me and the area below the second triangle the detected center of the body of the hyoid bone is included in. In this case, when the center of the body of the hyoid bone is included in the inside of the first triangle, it can be decided that there is no risk of obstructive sleep apnea syndrome, and when it locates in the inside of the second triangle or the area below the second triangle, it can be decided that there is the risk of obstructive sleep apnea syndrome. Furthermore, generally, when the center of the body of the hyoid bone locates in the area below the second triangle, it can be decided that the risk of obstructive sleep apnea syndrome is higher than the case where the center of the body of the hyoid bone locates in the inside of the second triangle. Detection of the center of the body of the hyoid bone, S, Go, Me and Cd in the first step typically can be carried out by image processing using a computer, for example.

Here, S, Go, Me and Cd are measured points to be obtained by lateral head and neck radiography, especially cephalometric radiography. The positions of each measured point are shown in FIG. 1. "S" is an abbreviation of Sella, and is a central point of pot-shaped shaded image of the sella turcica of the sphenoid bone. "Go" is an abbreviation of Gonion, and is a cross point of the angle of the mandible and the bisector of the cross angle between the line connecting the posterior plane of the head of the temporomandibular joint and the posterior part of the angle of the mandible and the mandibular plane. "Me" is an abbreviation of the menton, and is the lowest point of the median section image of a chin. "Cd" is the upper most point of the head of the mandible (condylion). FIG. 1 shows the first triangle and the second triangle.

As shown in FIG. 2, the hyoid bone is a mobile single bone separate from other bones of head skeletal system, which is generally considered to locate at a height of the same level as the third cervical vertebra of the front neck. The hyoid bone is connected with the mandible, the styloid process, the manubrium and the scapula by muscles and ligaments. As shown in FIG. 3A (right front outer side) and FIG. 3B (front plane view), the hyoid bone is comprised of the body (the body of the hyoid bone), the greater horn and the lesser horn and has a U-shape as a whole. The body is located in the central part of the hyoid bone and faces toward. The greater horn is comprised of the body and the both edge parts of the hyoid bone continuing from the body. The lesser horn is a small process projecting upward from a place near the junction of the greater horn and the body toward the styloid process and connected with the styloid process via the stylohyoid ligament. As shown in FIG. 3C, the cross section of the body of the hyoid bone on the median sagittal plane has a square shape with the rounded corners.

According to lateral head and neck radiography, because the X-ray transmission length penetrating through the body of the hyoid bone is much greater than that of the other parts of the hyoid bone, the body is definitely detected as a rectangular shape with the rounded corners and the greater horn is detected continuous with the body.

Furthermore, according to the invention, there is provided a method of deciding sinking of the hyoid bone, comprising:

using at least the hyoid bone, sella S, gonion Go and menton Me which are detected by lateral head and neck radiography of a subject and deciding whether the detected center of the body of the hyoid bone is included in an area above a perpendicular drawn toward the extended line of the segment S-Go from Me.

More specifically, the method of deciding sinking of the hyoid bone is carried out by a compute having a program comprising the above step. The method of deciding sinking of the hyoid bone typically comprises the first step of detecting at least the hyoid bone, sella S, gonion Go and menton Me by lateral head and neck radiography of the subject and the second step of deciding whether the detected center of the body of the hyoid bone is included in the area above the perpendicular drawn toward the extended line of the segment S-Go from Me or not. More specifically, in this case, the method of deciding sinking of the hyoid bone is carried out by a computer having a program comprising the first step and the second step. As needed, the method of deciding sinking of the hyoid bone decides in the second step whether the detected center of the body of the hyoid bone is included in the inside of the first triangle formed by the extended line of the segment S-Go, the perpendicular drawn toward the extended line of the segment S-Go from Me and the segment Go-Me. Furthermore, as needed, in the first step, condylion Cd is further detected by lateral head and neck radiography of the subject and in the second step, it is decided which area of the inside of the first triangle, the inside of the second triangle formed by the extended line of the segment Cd-Go, a perpendicular drawn toward the extended line of the segment Cd-Go from Me and the perpendicular drawn toward the extended line of the segment S-Go from Me and an area below the second triangle the detected center of the body of the hyoid bone is included in. Detection of the center of the body of the hyoid bone, S, Go, Me and Cd in the first step is typically carried out by image processing using a computer, for example.

The method of deciding the risk of obstructive sleep apnea syndrome and the method of deciding sinking of the hyoid bone can be easily carried out by a computer having at least one of the predetermined programs comprising the first step and the second step, as described above. Kinds of the computer are not limited and may be any one of a desk top type, a lap top type, various mobile terminals such as a tablet terminal etc. The programs can be stored in various computer-readable recording media such as, for example, a CD-ROM etc., or can be provided through electrical communication line such as internet etc. Typically, for example, lateral head and neck radiography of the subject is carried out using an X-ray diagnostic system with the computer having the program and the method of deciding the risk of obstructive sleep apnea syndrome and the method of deciding sinking of the hyoid bone are carried out based on the result. The computer and the X-ray diagnostic system may be connected by cable communications or radio communications.

Furthermore, according to the invention, there is provided a method of deciding the risk of obstructive sleep apnea syndrome, comprising:

deciding whether the hyoid bone is detected or not in an image taken by posteroanterior head and neck radiography or anteroposterior head and neck radiography of a subject.

Here, posteroanterior head and neck radiography is a radiography in which X rays transmit from the rear to the front of the subject and posteroanterior head and neck radiography is a radiography in which X rays transmit from the front to the rear of the subject. When the hyoid bone is not detected in the image taken by posteroanterior head and neck radiography or the anteroposterior head and neck radiography, it can be decided that there is no risk of obstructive sleep apnea syndrome. And when the hyoid bone is detected in the image taken by posteroanterior head and neck radiography or the anteroposterior head and neck radiography, it can be decided that there is the risk of obstructive sleep apnea syndrome. The case where the hyoid bone is not detected in the image taken by posteranterior head and neck radiography or anteroposterior head and neck radiography corresponds to a case where the hyoid bone is hidden by the mandible, in other words, the mandible and the hyoid bone cannot be distinguished. The case where the hyoid bone is detected in the image taken by posteranterior head and neck radiography or anteroposterior head and neck radiography corresponds to a case where the hyoid bone is not hidden by the mandible, because the position of the hyoid bone is low and the mandible and the hyoid bone can be distinguished. The method of deciding the risk of obstructive sleep apnea syndrome can be easily carried out by a computer having a predetermined program comprising the above step. Kinds of the computer are not limited and may be any one of a desktop type, a laptop type, various mobile terminals such as a tablet terminal etc. The program can be stored in various computer-readable recording media such as, for example, a CD-ROM etc., or can be provided through electrical communication line such as internet etc. Typically, for example, lateral head and neck radiography of the subject is carried out by an X-ray diagnostic system having a computer comprising the program and the method of deciding the risk of obstructive sleep apnea syndrome is carried out based on the result. The computer and the X-ray diagnostic system may be connected with cable communications or wireless communications.

In lateral head and neck radiography, posteroanterior head and neck radiography or anteroposterior head and neck radiography, it is preferable to take a radiograph under the same tilt in the front-rear direction of the head of the subject. The tilt in the front-rear direction of the head is typically set so that for example, the Frankfort plane of the head or a plane near to it (for example, a plane tilted at an angle within ±5° to the Frankfort plane becomes parallel to the floor surface (or the horizontal plane). In order to set the tilt in the front-rear direction of the head of the subject, it is preferable to use an X-ray radiographic apparatus or an X-ray radiographic method as described below.

The X-ray radiographic apparatus comprises: a pair of arms provided facing each other, ear rods respectively provided on inside surfaces facing each other of the pair of arms; and a head tilt setting device for setting the tilt in the front-rear direction of the head of the subject which is provided at at least one of the pair of arms or outside of the pair of arms. The pair of arms is typically provided facing each other with a reference line therebetween, and is constituted to be able to rotate around the reference line. The head tilt setting device typically sets the head tilt of a subject under the state inserting the ear rods of the pair of arms in the external acoustic openings of both ears of the subject. The head tilt setting device typically sets the head tilt so that when looking at the head from the lateral side (side surface), a straight line connecting the first reference point on the arms or the ear rods with the second reference point of the face of the subject becomes the horizontal line, or a straight line tilted at a predetermined angle to the horizontal line. The head tilt setting device has preferably the function of a protractor for measuring the inclination angle to the horizontal line centered on the first reference point. By using the function of a protractor, the tilt in the front-rear direction of the head can be set accurately. The inclination angle to the horizontal line centered on the first reference point may be a positive angle (when the straight line connecting the first reference point with the second reference point tilts upward to the horizontal line), or a negative angle (when the straight line connecting the first reference point with the second reference point tilts downward to the horizontal line).

The head tilt setting device is comprised of, for example, a transparent plate provided integrally with the arm, or provided on the exterior surface of the arm. The transparent plate is typically provided vertically to the central axis of the ear rods. The transparent plate preferably has a horizontal plane verification mechanism. The horizontal plane verification mechanism may be provided to the transparent plate or may be provided outside of the transparent plate. The horizontal plane verification mechanism can be used for an inspector to recognize the horizontal plane when setting the head tilt using the head tilt setting device. As described later, it can be said that the horizontal plane verification mechanism essentially constitutes a part of the head tilt setting device. That is, it can be said that the head tilt setting device has the transparent plate and the horizontal plane verification mechanism. As the horizontal plane verification mechanism, for example, a horizontal plate provided on the transparent plate protruding inside vertically to the transparent plate is used. In addition, as the horizontal plane verification mechanism, a colored horizontal line provided at the position of both sides of the transparent plate facing each other can be used. Confirmation of the horizontal plane may be carried out with an optical device (including a light source and a scanning mechanism) capable of irradiating a visible light beam or scanning it in the horizontal plane. The visible light beam may be a laser beam generated by a laser source such as a semiconductor laser (preferably, an eye-safe laser) or a beam-like light which is made from the light emitted from a light-emitting diode. The optical device may be provided to the transparent plate or may be provided outside of the transparent plate. Or, when providing the horizontal plane verification mechanism outside of the transparent plate, as the horizontal plane verification mechanism, for example, a horizontal plate capable of moving up and down or moving in the horizontal plane, an optical device (including a light source and a scanning mechanism) capable of scanning the visible light beam in the horizontal plane as the same as the optical device described above, a horizontal colored line, etc. may be used, but the horizontal plane verification mechanism is not limited to these. The horizontal plate may be a simple plate, and further, for example, the one having a foldable scale-like constitution which is able to open and close in the horizontal plane. The colored line is, for example, a thin linear wire made of metal, carbon fiber, plastics, etc. of which surface is colored, or a linear transparent fiber colored by making a visible light such as a red light or a green light, etc. wave guide from the end face. Further, the colored line may be the visible light beam itself. On the transparent plate constituting the head tilt setting device, as needed, a scale showing a length made of X-ray shielding materials is provided. Preferably, the transparent plate is provided on one of the pair of arms, and another transparent plate provided with a scale showing a length made of X-ray shielding materials is provided on the other arm of the pair of arms. These scales can serve as a reference of the length in radiographs or images obtained by cephalometric radiography. The head tilt setting device may be, for example, a camera (a digital still camera, a video camera, etc.) taking the head of the subject from the lateral direction and a display (a liquid crystal display, an organic EL display, etc.) displaying the images taken by the camera, and a protractor measuring the inclination angle to the horizontal line centered on the first reference point may be displayed on the display and looking at the display, the tilt of the head of the subject may be set to the desired angle.

In order to make the straight line connecting the first reference point with the second reference point become the Frankfort plane of the head or a plane near to it, the first reference point is selected to be, for example, the uppermost point of the ear rods (which coincides with the portions of both ears of a subject at the time of taking a radiograph), and the second reference point is selected to be, for example, the orbitale, the orbital margin just under the center of the pupil, or the center of the palpebral fissure, etc.

The X-ray radiographic apparatus is, for example, a cephalometric X-ray radiographic apparatus, but may be the other X-ray radiographic apparatus for medical and dental use, or may be a computed tomography (CT) apparatus, etc. For example, it is possible to construct an X-ray diagnostic apparatus for diagnosing obstructive sleep apnea syndrome by incorporating the function of deciding the risk of obstructive sleep apnea syndrome into the X-ray radiographic apparatus. Furthermore, it is also possible to construct a medical examination car for diagnosing obstructive sleep apnea syndrome by installing the X-ray diagnostic apparatus for diagnosing obstructive sleep apnea syndrome to a car such as a bus etc.

Furthermore, according to a method of measuring head tilt in taking a radiograph, when taking a radiograph of the head of the subject, set is the tilt in the front-rear direction of the head of the subject under the state that the ear rods respectively provided on inside surfaces facing each other of a pair of arms provided to mutually facing each other are inserted in the external acoustic openings of both ears of the subject so that the straight line connecting the first reference point on the arm or the ear rods with the second reference point of the face of the subject becomes the horizontal line or a straight line tilted at a predetermined angle to the horizontal line when looking at the head from the lateral direction. For this, preferably, the tilt of the head is measured by the head tilt setting device having the function of a protractor for measuring the inclination angle to the horizontal line centered on the first reference point.

It is also possible to use a stand for X-ray radiographic apparatus having the head tilt setting device for setting the tilt in the front-rear direction of the head of the subject when taking a radiograph. Here, the stand for X-ray radiographic apparatus is typically set so that the head tilt setting device comes to the same position as the head tilt setting device in the X-ray radiographic apparatus at the time of taking a radiograph.

It is also possible to use a chair for X-ray radiographic apparatus having the head tilt setting device for setting the tilt in the front-rear direction of the head of the subject at the time of taking a radiograph. Here, the head tilt setting device of the chair for X-ray radiographic apparatus is typically set at the same position as the head tilt setting device in the X-ray radiographic apparatus at the time of taking a radiograph.

In the stand for X-ray radiographic apparatus and the chair for X-ray radiographic apparatus, regarding other than those of mentioned above, the explanation concerning the X-ray radiographic apparatus comes into effect unless it is contrary to its character.

According to the X-ray radiographic apparatus, the method of measuring head tilt in taking a radiograph, the stand for X-ray radiographic apparatus and the chair for X-ray radiographic apparatus, it is possible to take a lateral head and neck radiograph, a posteroanterior head and neck radiograph and an anteroposterior head and neck radiograph under the same tilt in the front-rear direction of the head of the subject easily and with high reproducibility.

By the way, conventionally, an oral appliance (this is not a formal name and referred also as a mouthpiece.) has been used for treatment of obstructive sleep apnea syndrome. The oral appliance is divided into two types, one moving the mandible forward for the maxilla by attaching the oral appliance in the oral cavity and another one supporting the tongue forward. However, until now, the oral appliance has been made by dentists according to symptoms of a patient after repeated trial and error. Therefore, it takes a lot of time to make the oral appliance and it is not always possible to obtain the oral appliance effective for treatment. The present inventor has come to the conclusion that these problems can be solved by the result of decision by the method of deciding the risk of obstructive sleep apnea syndrome or the method of deciding sinking of the hyoid bone and devised a novel method of making an oral appliance.

That is, according to the invention, there is provided a method of making an oral appliance, comprising:

using at least the hyoid bone, sella S, gonion Go and menton Me which are detected by lateral head and neck radiography of a subject and deciding whether the detected center of the body of the hyoid bone is included in an area above a perpendicular drawn toward the extended line of the segment S-Go from Me or not; and making an oral appliance based on the result of decision.

According to the method of making an oral appliance, as needed, condylion Cd detected by lateral head and neck radiography of the subject is further used and it is decided which area of the area above the perpendicular drawn toward the extended line of the segment S-Go from Me, an area between the perpendicular drawn toward the extended line of the segment S-Go from Me and a perpendicular drawn toward the extended line of the segment Cd-Go from Me and an area below the perpendicular drawn toward the extended line of the segment Cd-Go from Me the detected center of the body of the hyoid bone is included in and based on the result of decision the oral appliance is made. And when it is decided that the detected center of the body of the hyoid bone is not included in the area above the perpendicular drawn toward the extended line of the segment S-Go from Me, the oral appliance is made so that when the oral appliance is attached in the oral cavity of the subject, the hyoid bone is lifted up by forward movement of the mandible for the maxilla, and as a result, the center of the body the hyoid bone is included in the area above the perpendicular drawn toward the extended line of the segment S-Go from Me. Or, when it is decided that the detected center of the body of the hyoid bone is included in the area between the perpendicular drawn toward the extended line of the segment S-Go from Me and the perpendicular drawn toward the extended line of the segment Cd-Go from Me, the oral appliance is made so that when the oral appliance is attached in the oral cavity of the subject, by forward movement of the mandible for the maxilla, the center of the body of the hyoid bone is included in the area above the perpendicular drawn toward the extended line of the segment S-Go from Me. Furthermore, when it is decided that the center of the body of the hyoid bone is included in the area below the perpendicular drawn toward the extended line of the segment Cd-Go from Me, the oral appliance is made so that when the oral appliance is attached in the oral cavity of the subject, by forward movement of the mandible for the maxilla, the center of the body of the hyoid bone is included in the area between the perpendicular drawn toward the extended line of the segment S-Go from Me and the perpendicular drawn toward the extended line of the segment Cd-Go from Me or the area above the perpendicular drawn toward the extended line of the segment S-Go from Me. Or, it is decided whether the detected center of the body of the hyoid bone is included in the inside of the first triangle formed by the extended line of the segment S-Go, the perpendicular drawn toward the extended line of the segment S-Go from Me and the segment Go-Me or not, and based on the result of decision the oral appliance is made. And when it is decided that the detected center of the body of the hyoid bone is not included in the inside of the first triangle, the oral appliance is made so that when the oral appliance is attached in the oral cavity, by forward movement of the mandible for the maxilla, the center of the body of the hyoid bone is included in the inside of the first triangle. Or, condylion Cd detected by lateral head and neck radiography of the subject is further used, and it is decided which area of the inside of the first triangle, the inside of the second triangle formed by the extended line of the segment Cd-Go, the perpendicular drawn toward the extended line of the segment Cd-Go from Me and the perpendicular drawn toward the extended line of the segment S-Go from Me and an area below the second triangle the detected center of the body of the hyoid bone is included in and based on the result of decision the oral appliance is made. And when it is decided that the detected center of the body of the hyoid bone is included in the inside of the second triangle, the oral appliance is made so that when the oral appliance is attached in the oral cavity, by forward movement of the mandible for the maxilla, the center of the body of the hyoid bone is included in the inside of the first triangle. Or, when it is decided that the detected center of the body of the hyoid bone is included in the area below the perpendicular drawn toward the extended line of the segment Cd-Go from Me, the oral appliance is made so that when the oral appliance is attached in the oral cavity of the subject, by forward movement of the mandible for the maxilla, the center of the body of the hyoid bone is included in the inside of the second triangle or the first triangle. Depending on the subject, when it is decided that the detected center of the body of the hyoid bone is not included in the area above the perpendicular drawn toward the extended line of the segment S-Go from Me or the inside of the first triangle, it may be difficult or a great burden to move the mandible forward for the maxilla by a single oral appliance to make the detected center of the body of the hyoid bone included in the area above the perpendicular drawn toward the extended line of the segment S-Go from Me or the inside of the first triangle. In this case, it may be possible to prepare plural kinds of oral appliance capable of moving the mandible forward for the maxilla by different distances and use these oral appliances sequentially to move the mandible forward for the maxilla stepwise. Or, even if the detected center of the body of the hyoid bone of a subject is decided to be included in the area above the perpendicular drawn toward the extended line of the segment S-Go from Me or the inside of the first triangle, when the hyoid bone sinks a little, the center of the body of the hyoid bone may become not included in the area above the perpendicular drawn toward the extended line of the segment S-Go from Me or the inside of the first triangle. For such a subject, it is possible to make an oral appliance so as to pull up the hyoid bone to prevent sinking of the hyoid bone from happening.

Furthermore, according to the invention, there is provided a method of making an oral appliance, comprising:

deciding whether the hyoid bone is detected in an image taken by posteroanterior head and neck radiography or anteroposterior head and neck radiography of a subject or not; and making an oral appliance based on the result of decision.

According to the method of making an oral appliance, when the hyoid bone is detected in the image, the oral appliance is made so that when the oral appliance is attached in the oral cavity of the subject, by forward movement of the mandible for the maxilla, the hyoid bone is not detected in the image taken by posteroanterior head and neck radiography or anteroposterior head and neck radiography of the subject.

In each of the above inventions deciding the risk of obstructive sleep apnea syndrome or deciding sinking of the hyoid bone by deciding which area the center of the body of the hyoid bone belongs to, it is possible to use the whole of the body of the hyoid bone instead of the center of the body of the hyoid bone and decide the risk of obstructive sleep apnea syndrome or decide sinking of the hyoid bone by deciding which area the whole of the body of the hyoid bone belongs to. For example, it is possible to use a method of deciding the risk of obstructive sleep apnea syndrome or a method of deciding sinking of the hyoid bone, comprising; using at least the hyoid bone, sella S, gonion Go and menton Me which are detected by lateral head and neck radiography of a subject and deciding whether the whole of the body of the detected hyoid bone is included in the area above the perpendicular drawn toward the extended line of the segment S-Go from Me or not. Furthermore, in each of the above inventions, gnathion Gn or pogonion Pog may be used instead of Me.

Effect of the Invention

According to the invention, it is possible to decide the risk of a subject to become obstructive sleep apnea syndrome or the presence or absence or the degree of sinking of the hyoid bone of a subject objectively and easily in a short time. In addition, it is possible to make an oral appliance effective for treatment of obstructive sleep apnea syndrome or sinking of the hyoid bone easily based on the result of decision of the risk of obstructive sleep apnea syndrome or decision of sinking of the hyoid bone.

Additional features and advantages are described herein, and will be apparent from the following Detailed Description and the figures.

BRIEF DESCRIPTION OF THE FIGURES

FIG. 2 A left side view of the cranium.

DETAILED DESCRIPTION

Modes for carrying out the invention (hereafter referred as "embodiments") will now be explained below.

1. The First Embodiment

In the first embodiment, the method of deciding the risk of obstructive sleep apnea syndrome based on lateral head and neck radiography of a subject is described.

Figure 4:
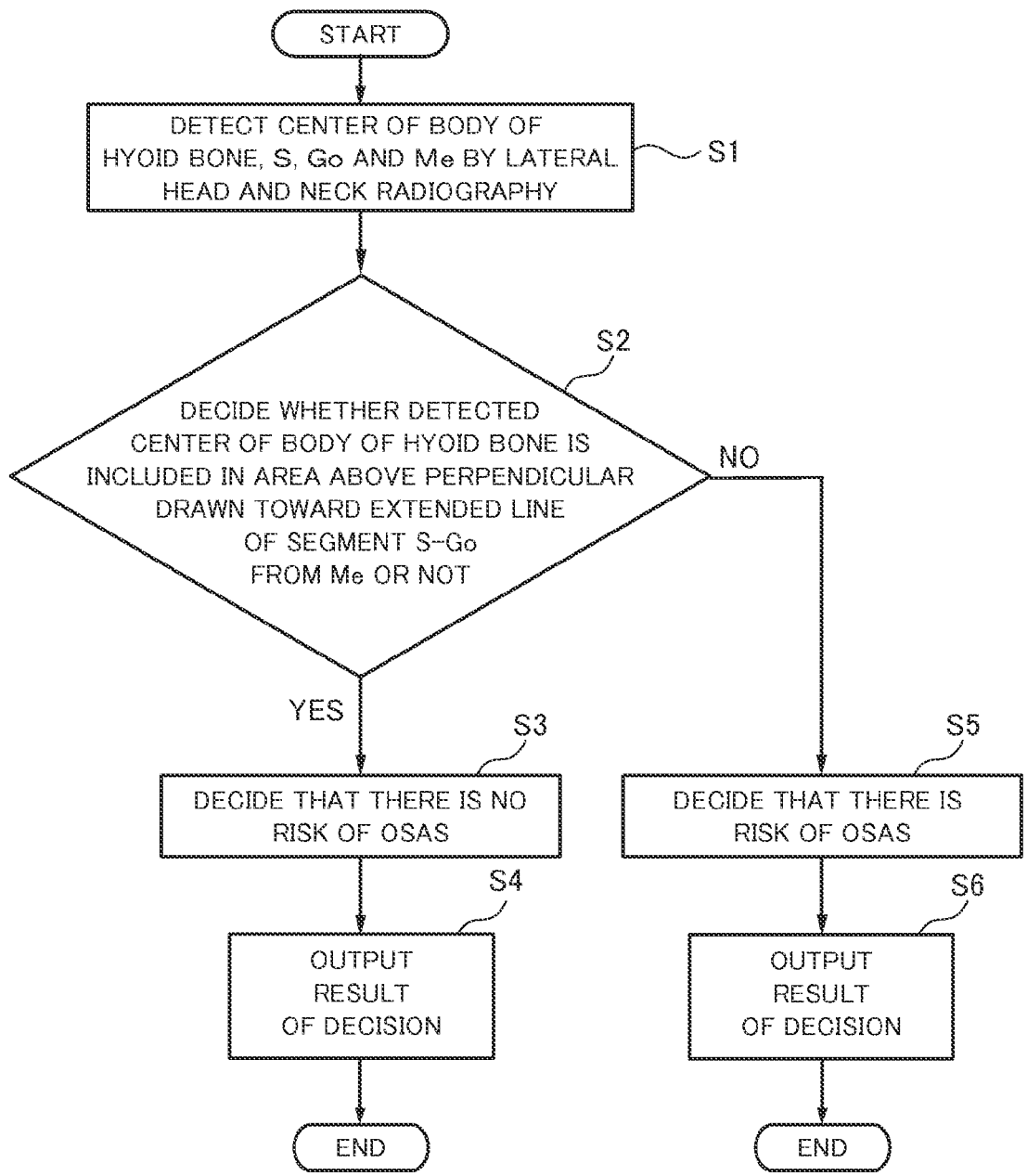
FIG. 4 A flow chart showing a method of deciding the risk of obstructive sleep apnea syndrome according to the first embodiment of the invention.

FIG. 4 shows a flow chart of the method of deciding the risk of obstructive sleep apnea syndrome. Programs are created according to the flow chart and are executed on a computer.

In step S1, the center of the body of the hyoid bone, S, Go and Me are detected by lateral head and neck radiography of the subject. That is, lateral head and neck radiography of the subject is carried out and the center of the body of the hyoid bone, S, Go and Me are detected from the image or radiograph. Radiography is carried out at centric occlusion or at a position near to it. Furthermore, radiography is carried out by setting the tilt in the front-rear direction of the head of the subject so that the Frankfort plane of the head becomes parallel to the floor surface.

Figure 5A:
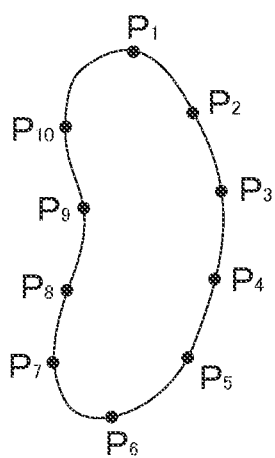
FIG. 5A A schematic drawing for explaining an example of input method of the body of the hyoid bone on the image taken by lateral head and neck radiography in the method of deciding the risk of obstructive sleep apnea syndrome according to the first embodiment of the invention.
Figure 5B:
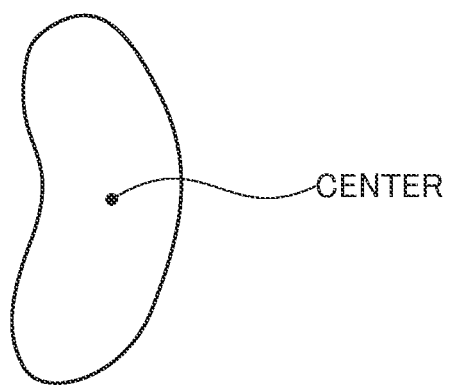
FIG. 5B A schematic drawing for explaining an example of input method of the body of the hyoid bone on the image taken by lateral head and neck radiography in the method of deciding the risk of obstructive sleep apnea syndrome according to the first embodiment of the invention.

Detection of the center of the body of the hyoid bone, S, Go and Me can be carried out, for example, in the state where the image is displayed on a display connected with a computer as follows. First, with respect to S, Go and Me, a cursor is moved to S, Go and Me by on the display using a mouse and clicked. Or, when a touch panel display is used, S, Go and Me are touched by fingers of the hand, touch pen, etc. on the display. In this way, S, Go and Me can be detected. The body of the hyoid bone can be detected as follows. That is, plural points showing the whole outline are clicked by the mouse on the outline of the body of the hyoid bone (the hyoid bone body) on the image and these points are connected by a straight line or a curved line, preferably a smooth curved line. A program connecting these points by a straight line or a curved line can be easily created. The outline of the body of the hyoid bone (the hyoid bone body) observed on the image has generally a rectangular shape having four rounded edges, which is relatively simple shape. Therefore, usually four to ten points will suffice for the number of these points. However, the more the number of points is, it is possible to depict the outline more correctly. Or, when the touch panel display is used, it is possible to trace the outline of the body of the hyoid bone on the display by fingers of the hand, touch pen, etc., magnifying and displaying the body of the hyoid bone as needed. The center of the body of the hyoid bone can be detected by obtaining the center of the figure made up of the outline of the body of the hyoid bone (the hyoid bone body) detected as described above. An example is shown in FIG. 5A and FIG. 5B. As shown in FIG. 5A, in the example, points $P_1$ to $P_{10}$ are clicked by using the mouse on the outline of the body of the hyoid bone on the image so as to depict the whole outline and these points $P_1$ to $P_{10}$ are connected smoothly by a curved line, so that an input image of the body of the hyoid bone (the hyoid bone body) can be obtained as shown in FIG. 5B. From the input image of the body of the hyoid bone obtained in this way the center of the body of the hyoid bone can be obtained as follows. That is, for example, the input image of the body of the hyoid bone is displayed on the xy coordinate plane with the x axis in the lateral direction and the y axis in the vertical direction. Y coordinates of the uppermost point and the lowermost point of the input image on the xy coordinate plane are obtained and the y coordinate of the uppermost point is denoted as $y_1$ and the y coordinate of the lowermost point is denoted as $y_2$. Then the y coordinate of the center of the input image of the body of the hyoid bone is denoted as $(y_1+y_2)/2$. Next, a straight line (a straight line parallel to the x axis) denoted as $(y_1+y_2)/2$ is drawn and x coordinates of two points at which the straight line intersects with the input image are denoted as $x_1$ and $x_2$. As a result, the x coordinate of the center of the input image of the body of the hyoid bone is equal to $(x_2+x_2)/2$. From the above, coordinates of the center of the input image of the body of the hyoid bone can be obtained as $((x_1+x_2)/2, (y_1+y_2)/2)$. Or, the center of the body of the hyoid bone can also be obtained by obtaining the center of gravity of the figure made up of the outline of the body of the hyoid bone by calculation. Unless the body of the hyoid bone has a peculiar shape, the position of the center of gravity almost coincides with the center having the coordinates of $((x_1+x_2)/2, (y_1+y_2)/2)$.

Figure 6:
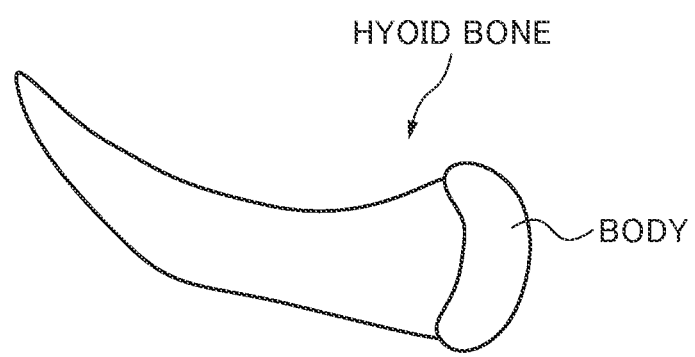
FIG. 6 A schematic drawing showing an example of the shape of the hyoid bone observed on the image taken by lateral head and neck radiography in the method of deciding the risk of obstructive sleep apnea syndrome according to the first embodiment of the invention.

The center of the body of the hyoid bone can also be detected by using image recognition technique as follows. That is, the shape of the whole hyoid bone observed on the image taken by lateral head and neck radiography is almost the same and has a curved shape as a whole as shown in FIG. 6, in which the body of the hyoid bone (the hyoid bone body) constitutes the right side part of the hyoid bone. Therefore, the position of the body of the hyoid bone (the hyoid bone body) is detected by conventionally known pattern recognition technique, specifically, for example, template matching technique. That is, the image data of the image taken by lateral head and neck radiography is taken in a computer, the standard shape of the hyoid bone shown in FIG. 6 is used as the standard image, i.e., the template and the image is used as an input image. As the hyoid bone locates in the lowermost part of the image, the input image can be limited to the lowermost part of the image, resulting a sharp reduction of data of the input image. And by moving the template on the input image, the position of the hyoid bone on the image can be detected. In this way, the body of the hyoid bone (the hyoid bone body) can be detected as the right side part of the hyoid bone and then the center of the body of the hyoid bone can be detected.

In step S2, it is decided whether the detected center of the body of the hyoid bone is included in the area above the perpendicular drawn toward the extended line of the segment S-Go from Me or not.

When it is decided in step S2 that the detected center of the body of the hyoid bone is included in the area above the perpendicular drawn toward the extended line of the segment S-Go from Me, it is decided in step S3 that there is no risk of OSAS.

In step S4, the result of decision that there is no risk of OSAS is output to, for example, a display.

When it is decided in step S2 that the detected center of the body of the hyoid bone is not included in the area above the perpendicular drawn toward the extended line of the segment S-Go from Me, it is decided in step S5 that there is the risk of OSAS.

In step S6, the result of decision that there is the risk of OSAS is output to, for example, the display.

Doctors can finally decide the risk of becoming OSAS by using also the result of other examinations conventionally used for examination of OSAS etc. in addition to the above decision, as needed. This is the same for the borderline case where the detected center of the body of the hyoid bone locates on the perpendicular drawn toward the extended line of the segment S-Go from Me or near to it.

According to the method of deciding the risk of obstructive sleep apnea syndrome according to the first embodiment, based on the center of the body of the hyoid bone, S, Go and Me which are detected by lateral head and neck radiography, it is possible to decide the risk of becoming OSAS objectively and in a short time with certain accuracy without depending on experiences of a doctor.

2. The Second Embodiment

In the second embodiment, the method of deciding the risk of obstructive sleep apnea syndrome based on lateral head and neck radiography of a subject is described.

Figure 7:
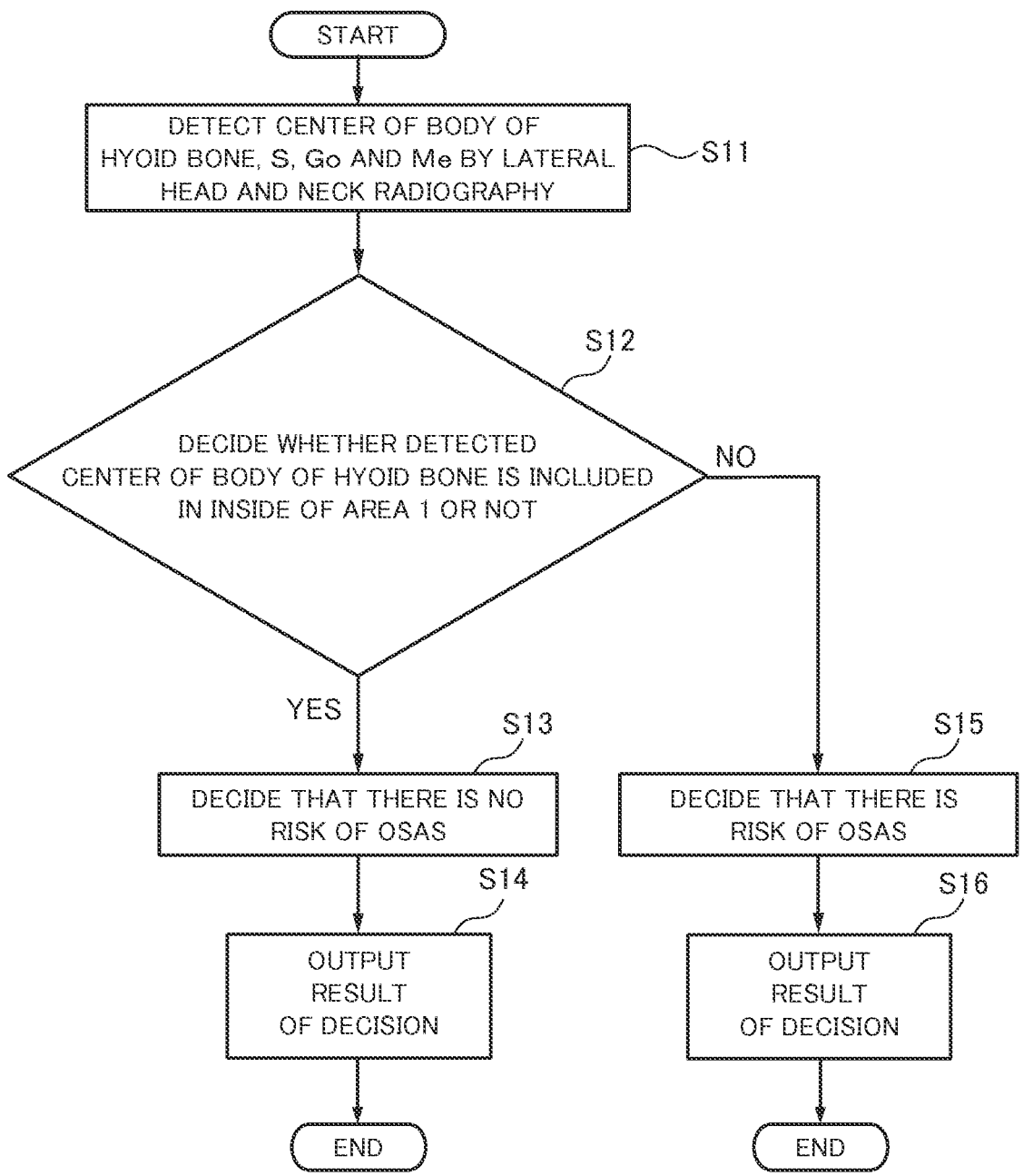
FIG. 7 A flow chart showing a method of deciding the risk of obstructive sleep apnea syndrome according to the second embodiment of the invention.

FIG. 7 shows a flow chart of the method of deciding the risk of obstructive sleep apnea syndrome. Programs are created according to the flow chart and are executed on a computer.

In step S11, the center of the body of the hyoid bone, S, Go and Me are detected by lateral head and neck radiography of the subject. That is, lateral head and neck radiography of the subject is carried out and the center of the body of the hyoid bone, S, Go and Me are detected from the image or radiograph. Radiography is carried out at centric occlusion or at a position near to it. Furthermore, radiography is carried out by setting the tilt in the front-rear direction of the head so that the Frankfort plane of the head of the subject becomes parallel to the floor surface.

Detection of the center of the body of the hyoid bone, S, Go and Me can be carried out as the same as the first embodiment.

In step S12, it is decided whether the detected center of the body of the hyoid bone is included in the inside of the first triangle (hereafter referred as "the area 1") formed by the extended line of the segment S-Go, the perpendicular drawn toward the extended line of the segment S-Go from Me and the segment Go-Me or not.

When it is decided in step S12 that the detected center of the body of the hyoid bone is included in the inside of the area 1, it is decided in step S13 that there is no risk of OSAS.

In step S14, the result of decision that there is no risk of OSAS is output to, for example, the display.

When it is decided in step S12 that the detected center of the body of the hyoid bone is not included in the inside of the area 1, in other words, it locates below the area 1, it is decided in step S15 that there is the risk of OSAS.

In step S16, the result of decision that there is the risk of OSAS is output to, for example, the display.

Doctors can finally decide the risk of becoming OSAS by using also the result of other examinations conventionally used for examination of OSAS etc. in addition to the above decision, as needed. This is the same for the borderline case where the detected center of the body of the hyoid bone locates on the base of the area 1 (the perpendicular drawn toward the extended line of the segment S-Go from Me) or the side (the extended line of the segment S-Go) or near to it.

According to the method of deciding the risk of obstructive sleep apnea syndrome according to the second embodiment, based on the center of the body of the hyoid bone, S, Go and Me which are detected by lateral head and neck radiography, it is possible to decide the risk of becoming OSAS objectively and in a short time with certain accuracy without depending on experiences of a doctor.

3. The Third Embodiment

In the third embodiment, the method of deciding the risk of obstructive sleep apnea syndrome based on lateral head and neck radiography of a subject is described.

Figure 8:
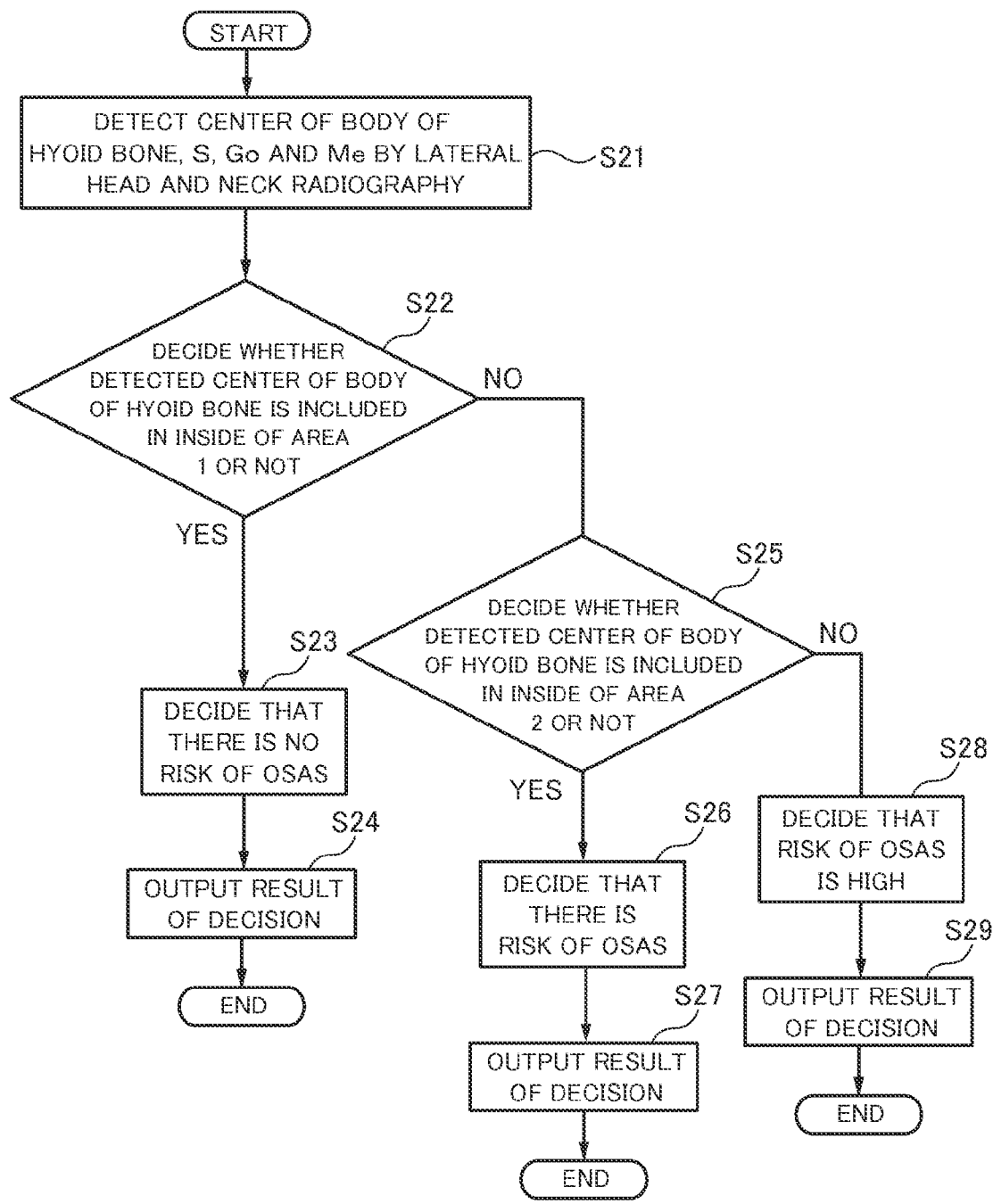
FIG. 8 A flow chart showing a method of deciding the risk of obstructive sleep apnea syndrome according to the third embodiment of the invention.
Figure 9:
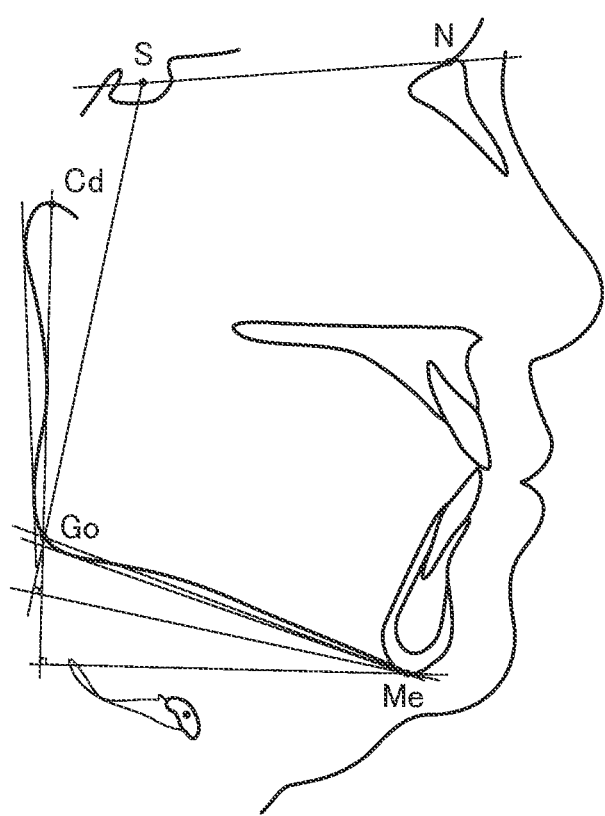
FIG. 9 A tracing made based on a lateral head and neck radiograph of a patient 1.
Figure 10:
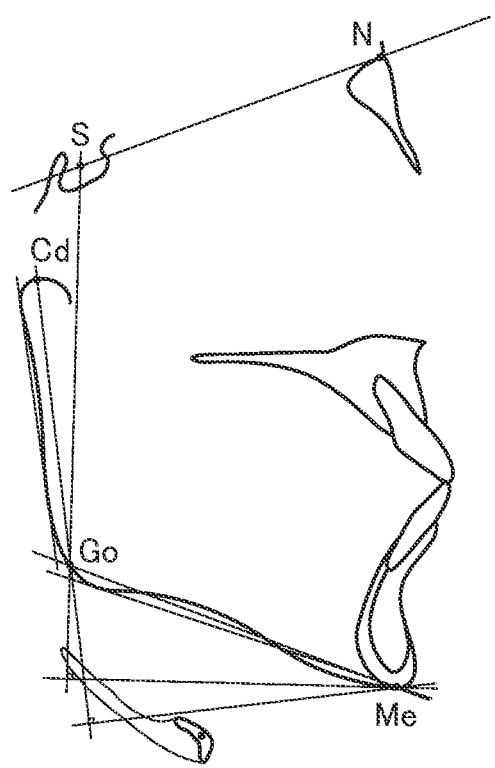
FIG. 10 A tracing made based on a lateral head and neck radiograph of a patient 2.
Figure 11:
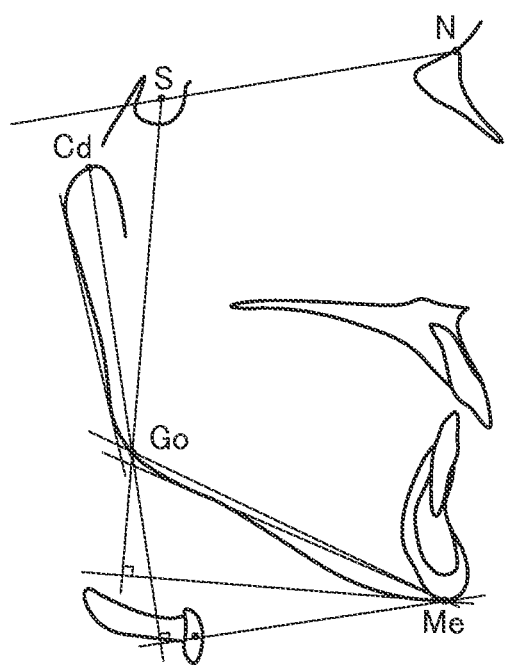
FIG. 11 A tracing made based on a lateral head and neck radiograph of a patient 3.
Figure 12:
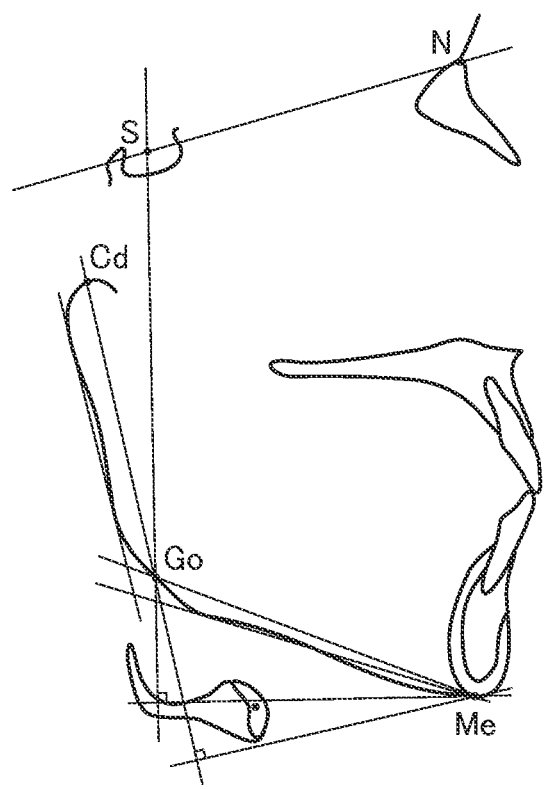
FIG. 12 A tracing made based on a lateral head and neck radiograph of a patient 4.
Figure 13:
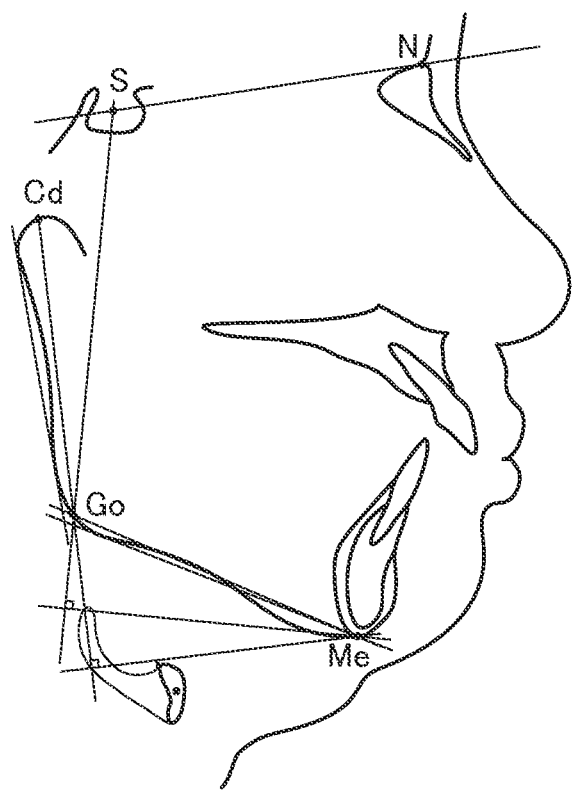
FIG. 13 A tracing made based on a lateral head and neck radiograph of a patient 5.
Figure 14:
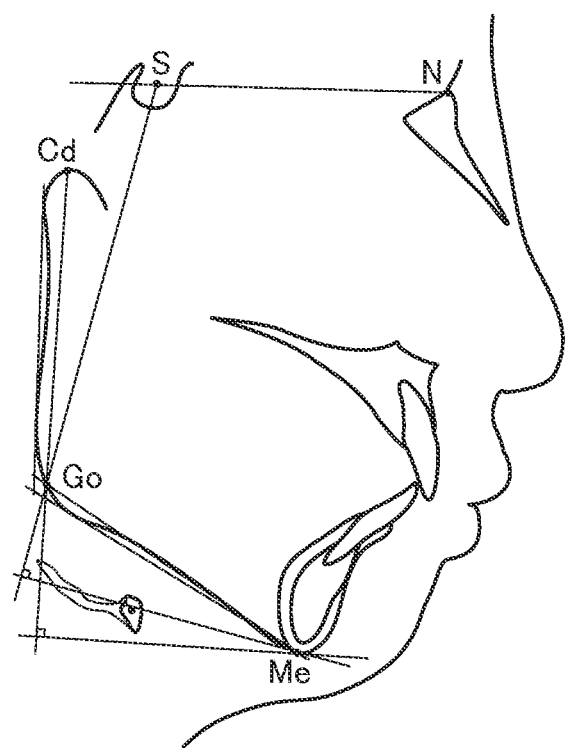
FIG. 14 A tracing made based on a lateral head and neck radiograph of a patient 6.
Figure 15:
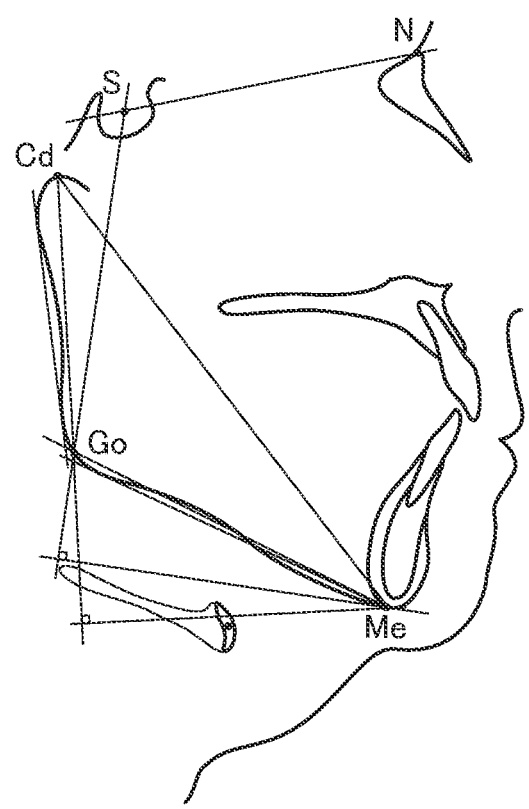
FIG. 15 A tracing made based on a lateral head and neck radiograph of a patient 7.
Figure 16:
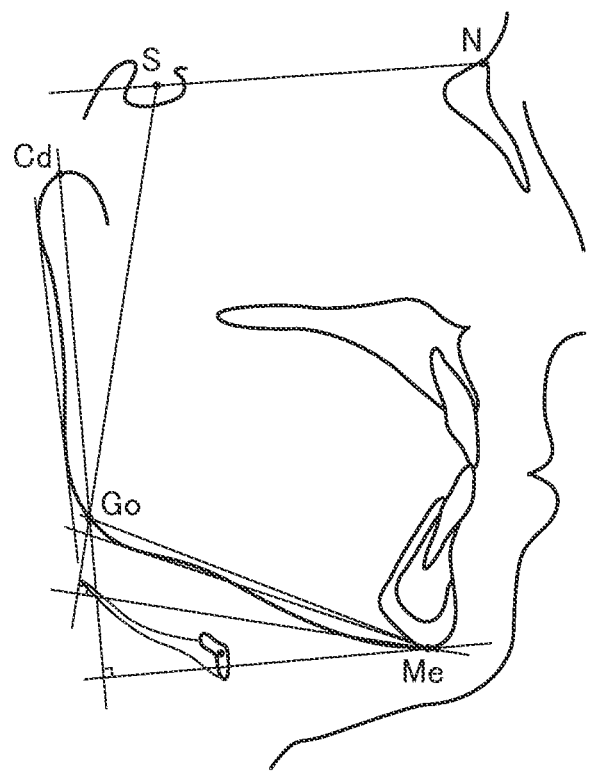
FIG. 16 A tracing made based on a lateral head and neck radiograph of a patient 8.
Figure 17:
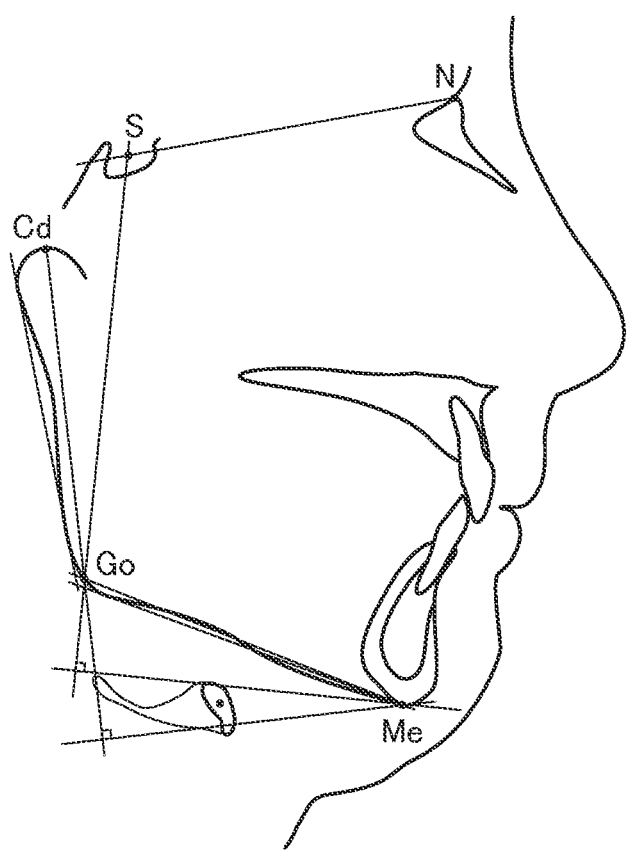
FIG. 17 A tracing made based on a lateral head and neck radiograph of a patient 9.
Figure 18:
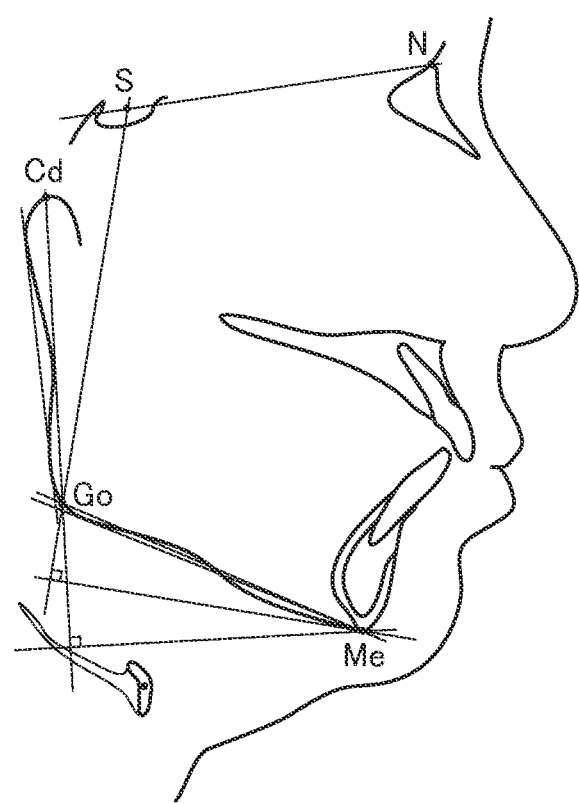
FIG. 18 A tracing made based on a lateral head and neck radiograph of a patient 10.
Figure 19:
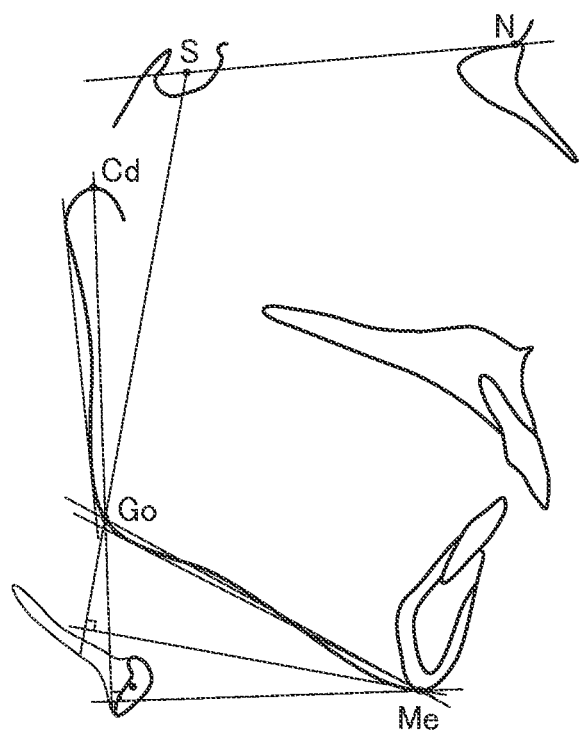
FIG. 19 A tracing made based on a lateral head and neck radiograph of a patient 11.
Figure 20:
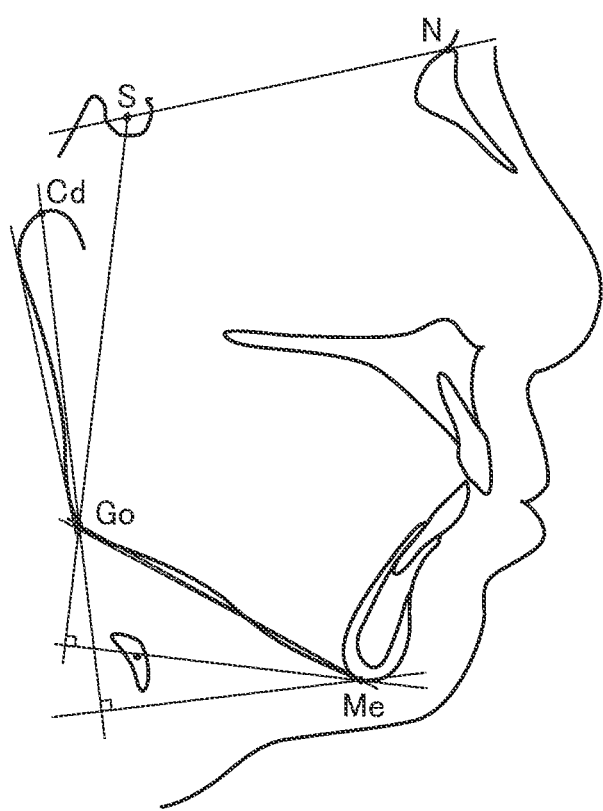
FIG. 20 A tracing made based on a lateral head and neck radiograph of a patient 12.
Figure 21:
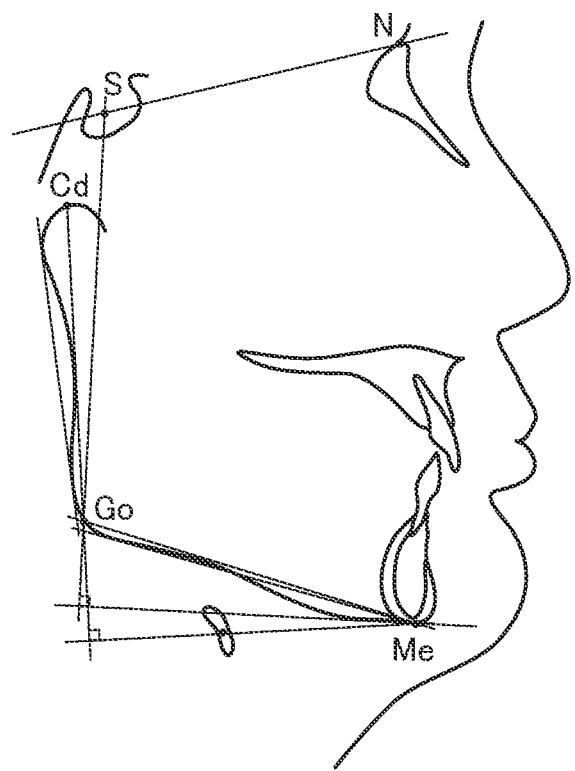
FIG. 21 A tracing made based on a lateral head and neck radiograph of a patient 13.
Figure 22:
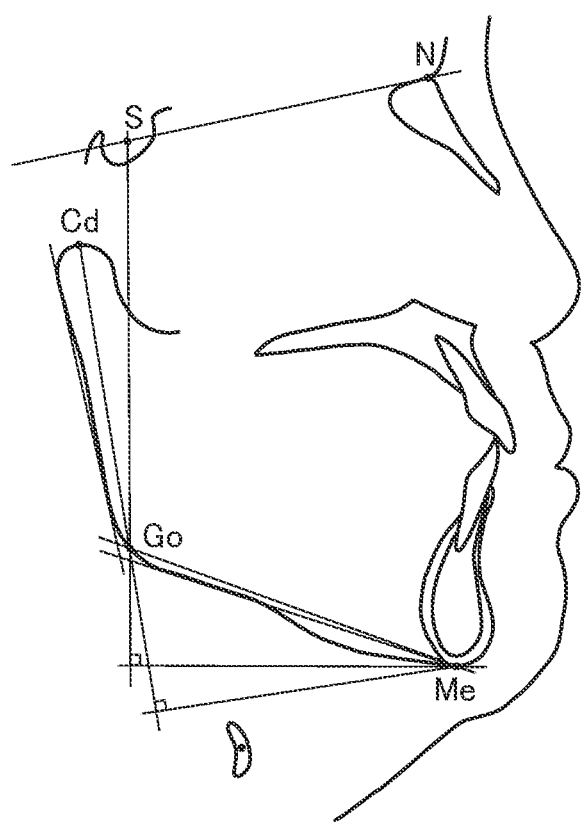
FIG. 22 A tracing made based on a lateral head and neck radiograph of a patient 14.
Figure 23:
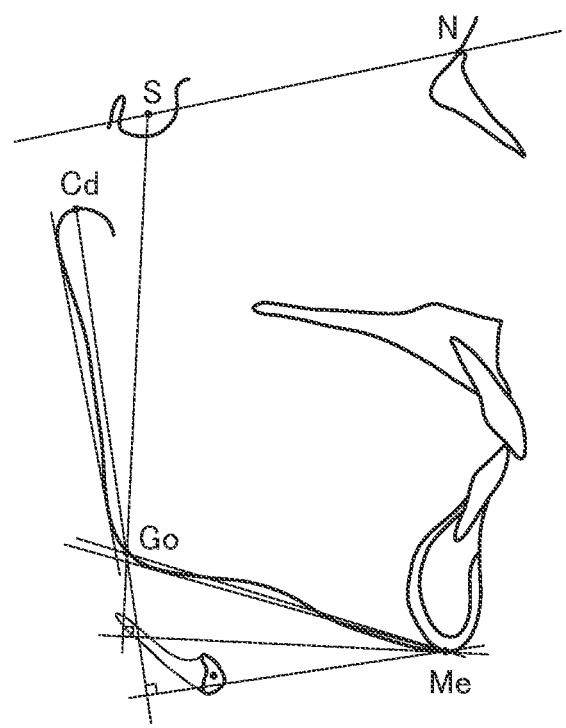
FIG. 23 A tracing made based on a lateral head and neck radiograph of a patient 15.
Figure 24:
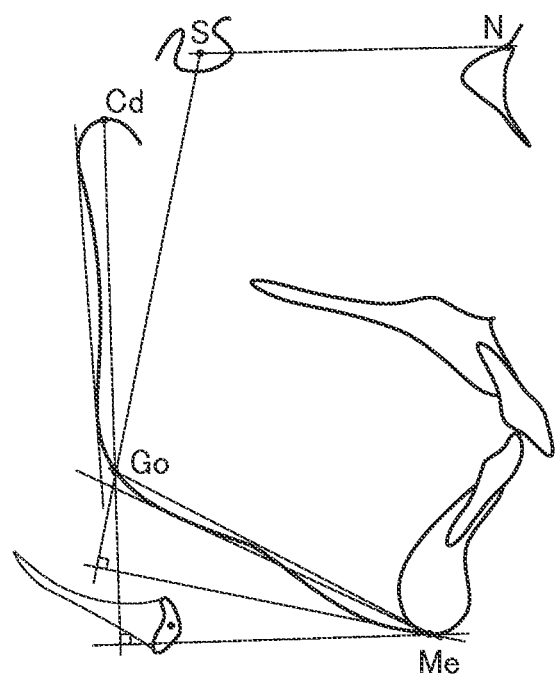
FIG. 24 A tracing made based on a lateral head and neck radiograph of a patient 16.
Figure 25:
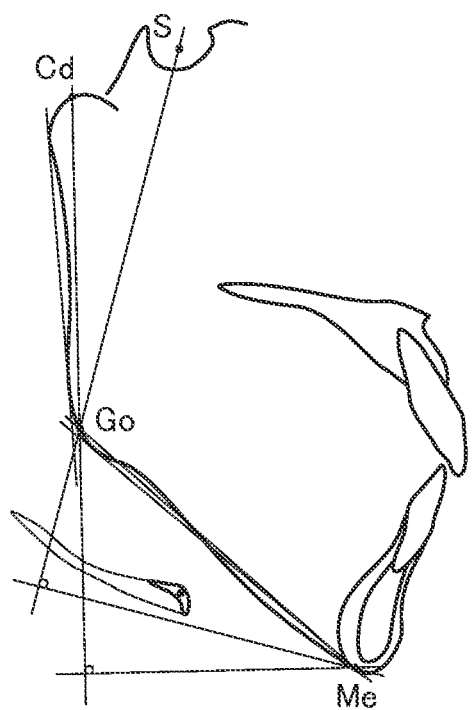
FIG. 25 A tracing made based on a lateral head and neck radiograph of a subject 17.
Figure 26:
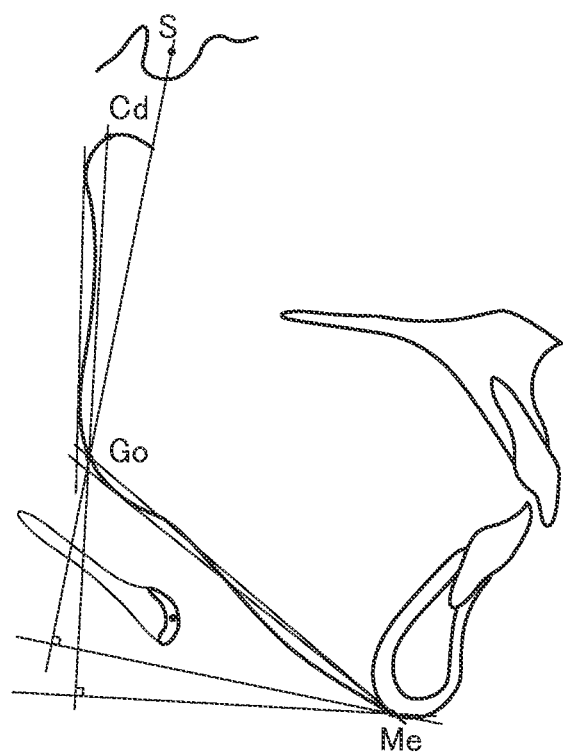
FIG. 26 A tracing made based on a lateral head and neck radiograph of a subject 18.
Figure 27:
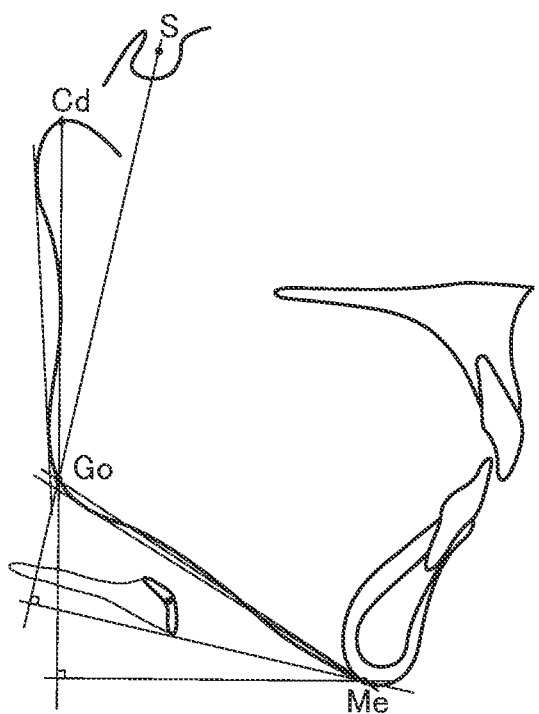
FIG. 27 A tracing made based on a lateral head and neck radiograph of a subject 19.
Figure 28:
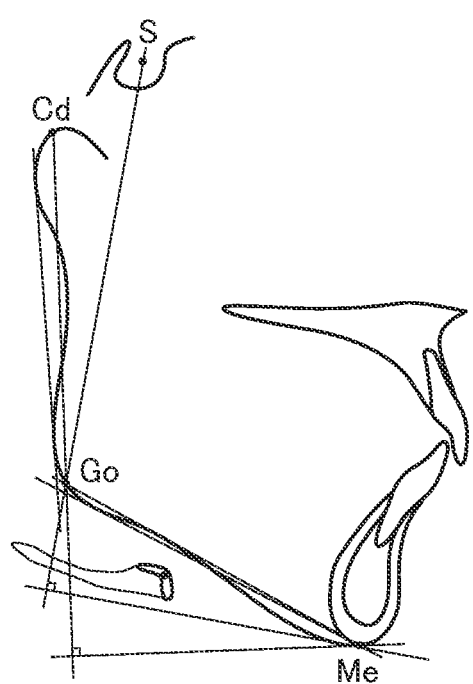
FIG. 28 A tracing made based on a lateral head and neck radiograph of a subject 20.
Figure 29:
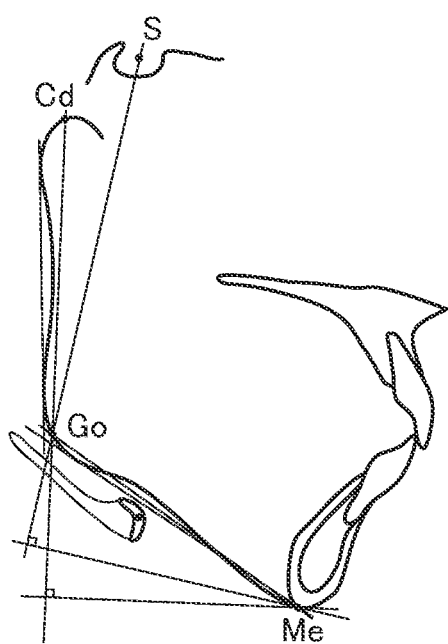
FIG. 29 A tracing made based on a lateral head and neck radiograph of a subject 21.

FIG. 8 shows a flow chart of the method of deciding the risk of obstructive sleep apnea system. Programs are created according to the flow chart and are executed on a computer.

In step S21, the center of the body of the hyoid bone, S, Go, Me and Cd are detected by lateral head and neck radiography of the subject. That is, lateral head and neck radiography of the subject is carried out and the center of the body of the hyoid bone, S, Go, Me and Cd are detected from the image or radiograph. Radiography is carried out at centric occlusion or at a position near to it. Furthermore, radiography is carried out by setting the tilt in the front-rear direction of the head so that the Frankfort plane of the head of the subject becomes parallel to the floor surface.

Detection of the center of the body of the hyoid bone, S, Go, Me and Cd can be carried out as the same as the first embodiment.

In step S22, it is decided whether the detected center of the body of the hyoid bone is included in the inside of the area 1 or not.

When it is decided in step S22 that the detected center of the body of the hyoid bone is included in the inside of the area 1, it is decided in step S23 that there is no risk of OSAS.

In step S24, the result of decision that there is no risk of OSAS is output to for example, the display.

When it is decided in step S22 that the detected center of the body of the hyoid bone is not included in the inside of the area 1, in other words, it locates below the area 1, it is decided in step S25 whether the detected center of the body of the hyoid bone is included in the inside of the second triangle (hereafter referred as "the area 2") formed by the extended line of the segment Cd-Go, the perpendicular drawn toward the extended line of the segment Cd-Go from Me and the perpendicular drawn toward the extended line of the segment S-Go from Me.

When it is decided in step S25 that the detected center of the body of the hyoid bone is included in the inside of the area 2, it is decided in step S26 that there is the risk of OSAS.

In step S27, the result of decision that there is the risk of OSAS is output to, for example, the display.

When it is decided in step S25 that the detected center of the body of the hyoid bone is not included in the inside of the area 2, in other words, it locates in the area 3, it is decided in step S28 that the risk of OSAS is high.

In step S29, the result of decision that the risk of OSAS is high is output to, for example, the display.

Doctors can finally decide the risk of becoming OSAS by using also the result of other examinations conventionally used for examination of OSAS etc. in addition to the above decision, as needed. This is the same for the borderline case where the detected center of the body of the hyoid bone locates on the base of the area 1 (the perpendicular drawn toward the extended line of the segment S-Go from Me) or the side (the extended line of the segment S-Go) or near to it, or, it locates on the base of the area 2 (the perpendicular drawn toward the extended line of the segment Cd-Go from Me) or the side (the extended line of the segment Cd-Go) or near to it.

According to the method of deciding the risk of obstructive sleep apnea syndrome according to the third embodiment, based on the center of the body of the hyoid bone, S, Go, Me and Cd which are detected by lateral head and neck radiography, it is possible to decide the risk of becoming OSAS objectively and in a short time with certain accuracy without depending on experiences of a doctor.

Example 1

Taken were head and neck radiographs of sixteen patients who were diagnosed as a serious illness, a medium illness or a slight illness by examination of OSAS carried out by PSG. Radiography was carried out at centric occlusion or at a position near to it by setting the Frankfort plane parallel to the floor surface.

Tracings of the patients 1 to 16 are shown in FIG. 9 to FIG. 24. AHI (supine position) and $SaO_2$ (the lowest value) obtained by PSG of the patients 1 to 16 are as follows. With respect to the patient 13, $SpO_2$ (the lowest value) is shown instead of $SaO_2$ (the lowest value).

| Patient | AHI | $SaO_2$ (%) |
|---|---|---|
| 1 | 43.1 | 70 |
| 2 | 36.8 | 87 |
| 3 | 30.2 | 83 |
| 4 | 62.9 | 73 |
| 5 | 53.5 | 71 |
| 6 | 25.7 | 79 |
| 7 | 112.5 | 85 |
| 8 | 11.9 | 93 |
| 9 | 35.5 | 80 |
| 10 | 66.0 | 76 |
| 11 | 24.8 | 92 |
| 12 | 9.6 | 90 |
| 13 | 41.1 | 68($SpO_2$) |
| 14 | 59.7 | 80 |
| 15 | 71.2 | 71 |
| 16 | 43.9 | 85 |

As a control group, five subjects 17 to 21 who were not recognized respiratory disorder during sleep were adopted. Head and neck radiographs of the subject 17 to 21 were taken. Tracings of the subjects 17 to 21 are shown in FIG. 25 to FIG. 29.

The center of the body of the hyoid bone of the patients 1 to 16 were detected. As a result, the area in which the center of the body of the hyoid bone locates was as follows.

| Patient | Area in which the center of the body of the hyoid bone locates | Risk of becoming OSAS |
|---|---|---|
| 1 | area 3 | yes(high) |
| 2 | area 3 | yes(high) |
| 3 | area 2 | yes |
| 4 | area 2 | yes |
| 5 | area 3 | yes(high) |
| 6 | area 2 | yes |
| 7 | area 3 | yes(high) |
| 8 | area 2 | yes |
| 9 | area 2 | yes |
| 10 | area 3 | yes(high) |
| 11 | area 2 | yes |
| 12 | area 2 | yes |
| 13 | area 2 | yes |
| 14 | area 3 | yes(high) |
| 15 | area 2 | yes |
| 16 | area 2 | yes |

The center of the body of the hyoid bone of the subjects 17 to 21 were detected. As a result, the area in which the center of the body of the hyoid bone locates was as follows.

| Subject | Area in which the center of the body of the hyoid bone locates | Risk of becoming OSAS |
|---|---|---|
| 17 | area 1 | no |
| 18 | area 1 | no |
| 19 | area 1 | no |
| 20 | area 1 | no |
| 21 | area 1 | no |

As understood from the above result, it is possible to decide the risk of becoming OSAS by taking a head and neck radiography and detect which area of the areas 1, 2 and 3 the center of the body of the hyoid bone locates from the image or the radiograph.

4. The Fourth Embodiment

In the fourth embodiment, the method of deciding the risk of obstructive sleep apnea syndrome based on posteroanterior radiography of a subject is described.

Figure 30:
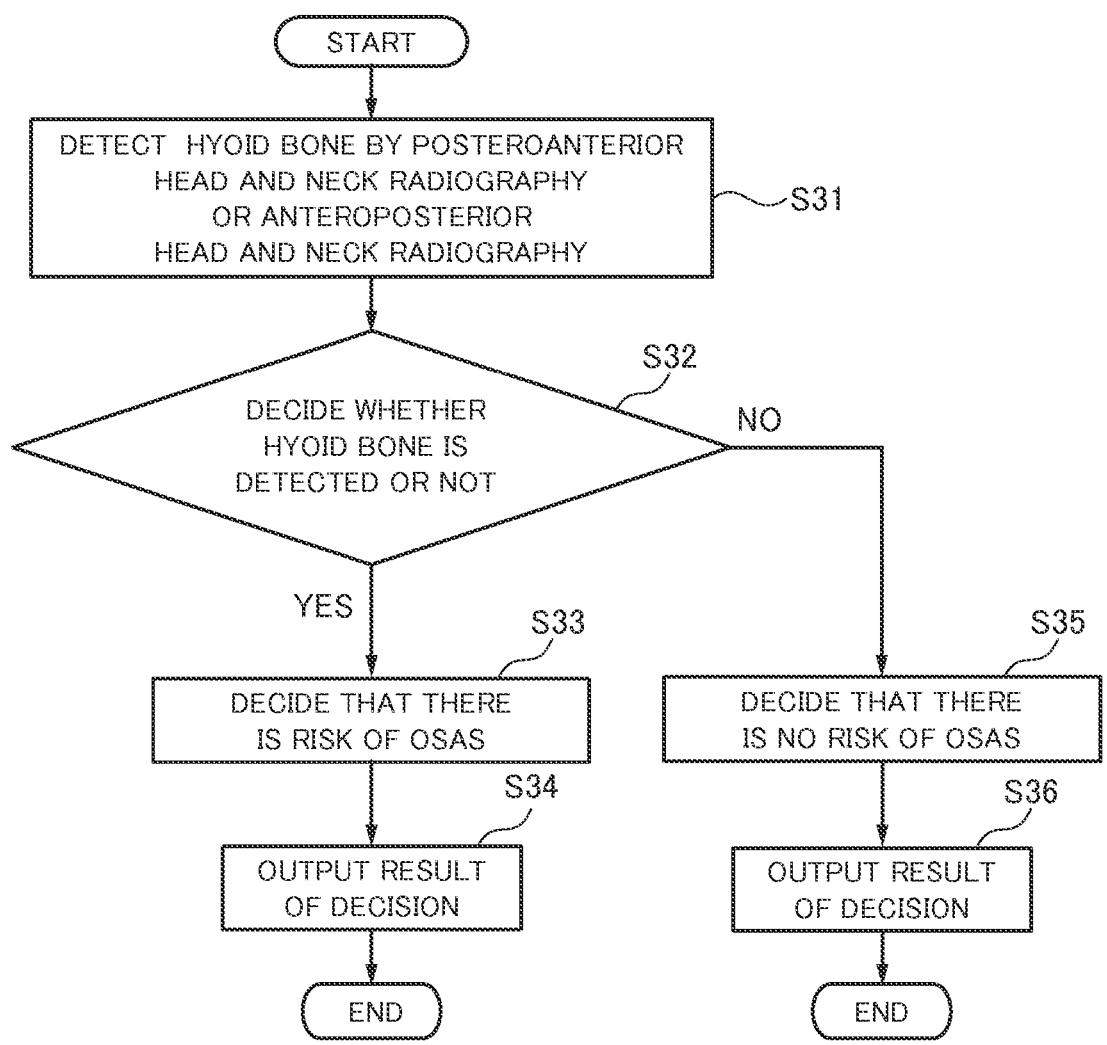
FIG. 30 A flow chart showing a method of deciding the risk of obstructive sleep apnea syndrome according to the fourth embodiment of the invention.

FIG. 30 shows a flow chart of the method of deciding the risk of obstructive sleep apnea syndrome. Programs are created according to the flow chart and are executed on a computer.

In step S31, posteroanterior head and neck radiography of a subject is carried out and the hyoid bone is detected from the image. Radiography is carried out at centric occlusion or at a position near to it. Radiography is carried out by setting the tilt in the front-rear direction of the head so that the Frankfort plane of the head of the subject becomes parallel to the floor surface.

Figure 3A:
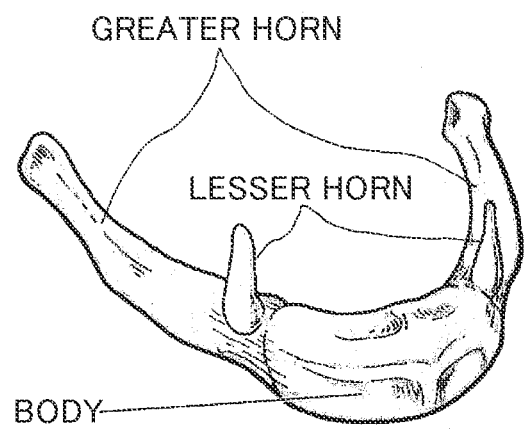
FIG. 3A A perspective view showing the hyoid bone.
Figure 3B:
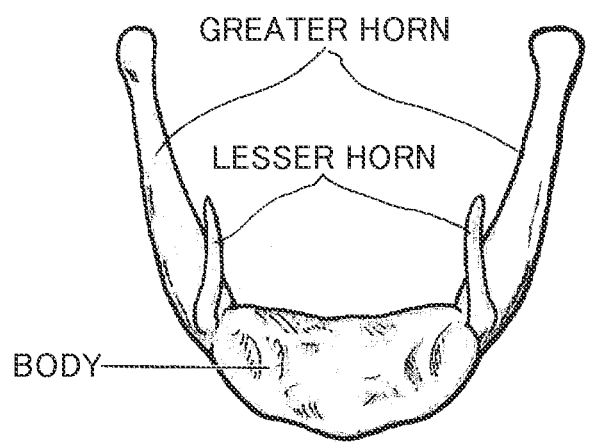
FIG. 3B A cross sectional view showing the hyoid bone.
Figure 3C:
FIG. 3C A cross sectional view showing the body of the hyoid bone.

Detection of the hyoid bone can be carried out, for example, by image recognition technique in the state where the image is displayed on the display connected with a computer as follows. That is, the shape of the whole hyoid bone observed on the image taken by posteroanterior head and neck radiography is almost the same and the hyoid bone has, as a whole, a shape with its both end parts bent outward in the diagonally upward direction with respect to its central part (See FIG. 3A and FIG. 3B). Therefore, the position of the hyoid bone is detected by using conventionally known pattern recognition technique, specifically, for example, template matching technique. That is, the image data of the image taken by posteroanterior head and neck radiography is taken in a computer, the standard shape of the hyoid bone is used as the standard image, i.e., the template and the image is used as an input image. As the hyoid bone locates in the lowermost part of the image, the input image can be limited to the lowermost part of the image, resulting a sharp reduction of data of the input image. And by moving the template on the input image, the hyoid bone on the image can be detected.

In step S32, it is decided whether the hyoid bone is detected or not.

When the hyoid bone is detected in step S32, it is decided in step S33 that there is the risk of OSAS.

In step S34, the result of decision that there is the risk of OSAS is output to, for example, the display.

When the hyoid bone is not detected in step S32, it is decided in step S35 that there is no risk of OSAS.

In step S36, the result of decision that there is no risk of OSAS is output to, for example, the display.

Doctors can finally decide the risk of becoming OSAS by using also the result of other examinations conventionally used for examination of OSAS etc. in addition to the above decision, as needed.

According to the method of deciding the risk of obstructive sleep apnea syndrome according to the fourth embodiment, it is possible to decide the risk of becoming OSAS objectively and in a short time with certain accuracy without depending on experiences of a doctor.

Example 2

Taken were a lateral head and neck radiograph and a posteroanterior head and neck radiograph of the subject 22. Radiography was carried out at centric occlusion or a position near to it by setting the Frankfort plane parallel to the floor surface.

Figure 31:
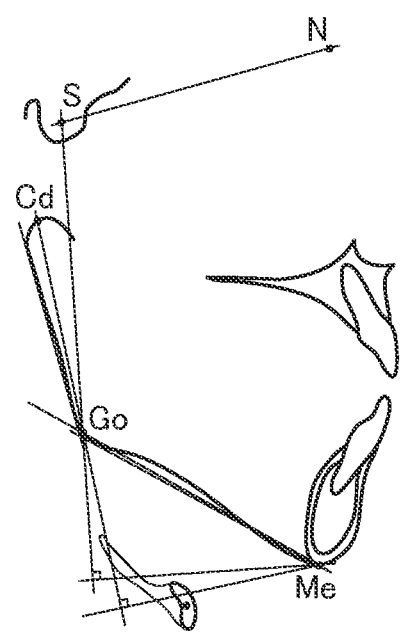
FIG. 31 A tracing made based on a lateral head and neck radiograph of a subject 22.
Figure 32:
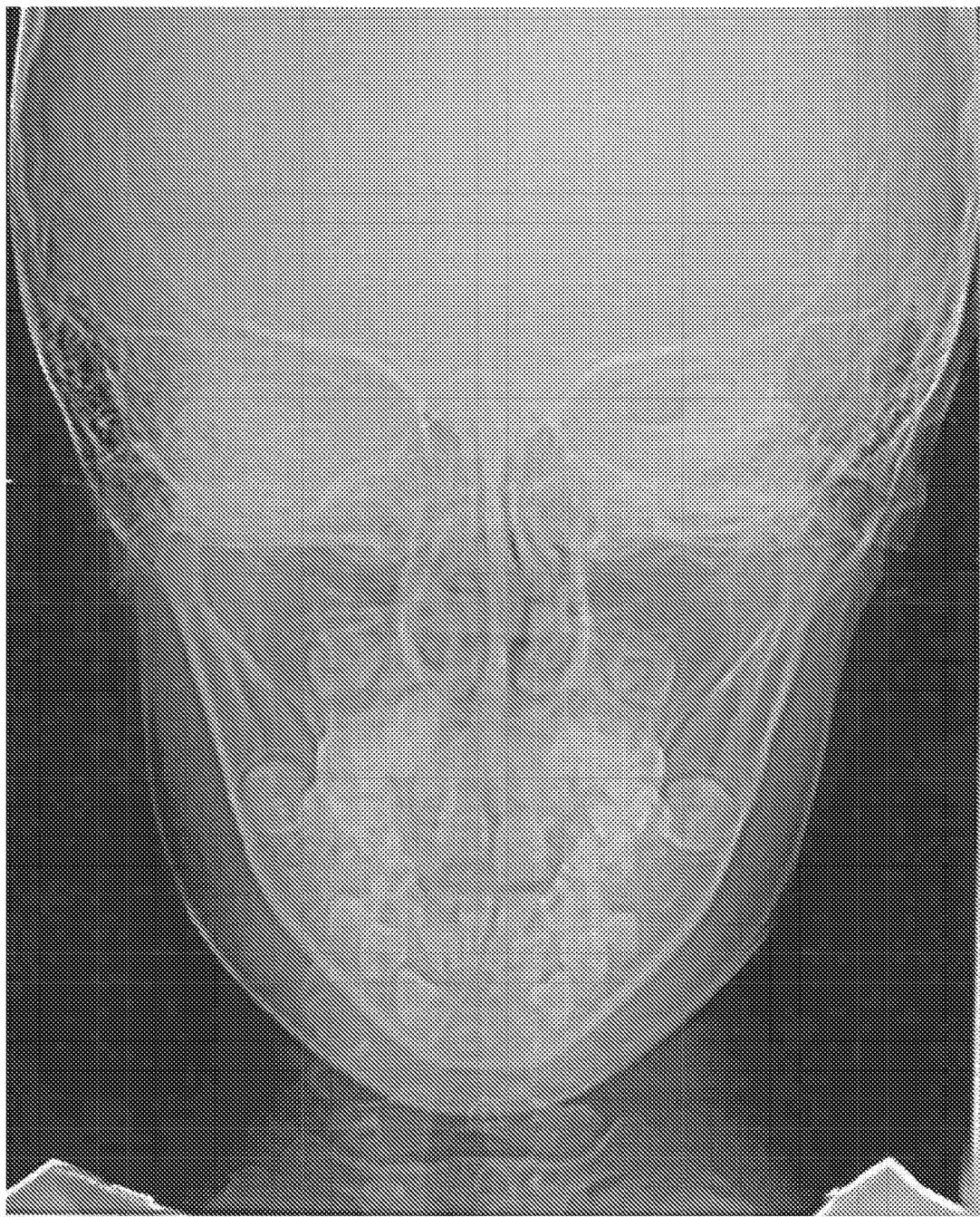
FIG. 32 A substitute picture for a drawing showing a posteroanterior head and neck radiograph of the subject 22.

A tracing of the lateral head and neck radiograph of the subject 22 is shown is FIG. 31. The posteroanterior head and neck radiograph of the subject 22 is shown in FIG. 32.

The center of the body of the hyoid bone, S, Go, Me and Cd were detected from FIG. 31. As a result, it was known that the center of the body of the hyoid bone located in the inside of the area 3 and the risk of becoming OSAS was high. On the other hand, the hyoid bone was detected from FIG. 32, so that the hyoid bone was detected below the mandible. That is, as the hyoid bone was detected, it can be decided that there is the risk of becoming OSAS. Taking into consideration that the center of the body of the hyoid bone locates in the inside of the area 3, it is possible to decide that the risk of becoming OSAS of the subject 22 is high.

According to the method of deciding the risk of obstructive sleep apnea syndrome according to the fourth embodiment, by deciding whether the hyoid bone is detected by posteroanterior head and neck radiography or not, it is possible to decide the risk of becoming OSAS objectively and in a short time with certain accuracy without depending on experiences of a doctor.

5. The Fifth Embodiment

In the fifth embodiment, the method of deciding sinking of the hyoid bone based on lateral head and neck radiography of a subject is described.

Figure 33:
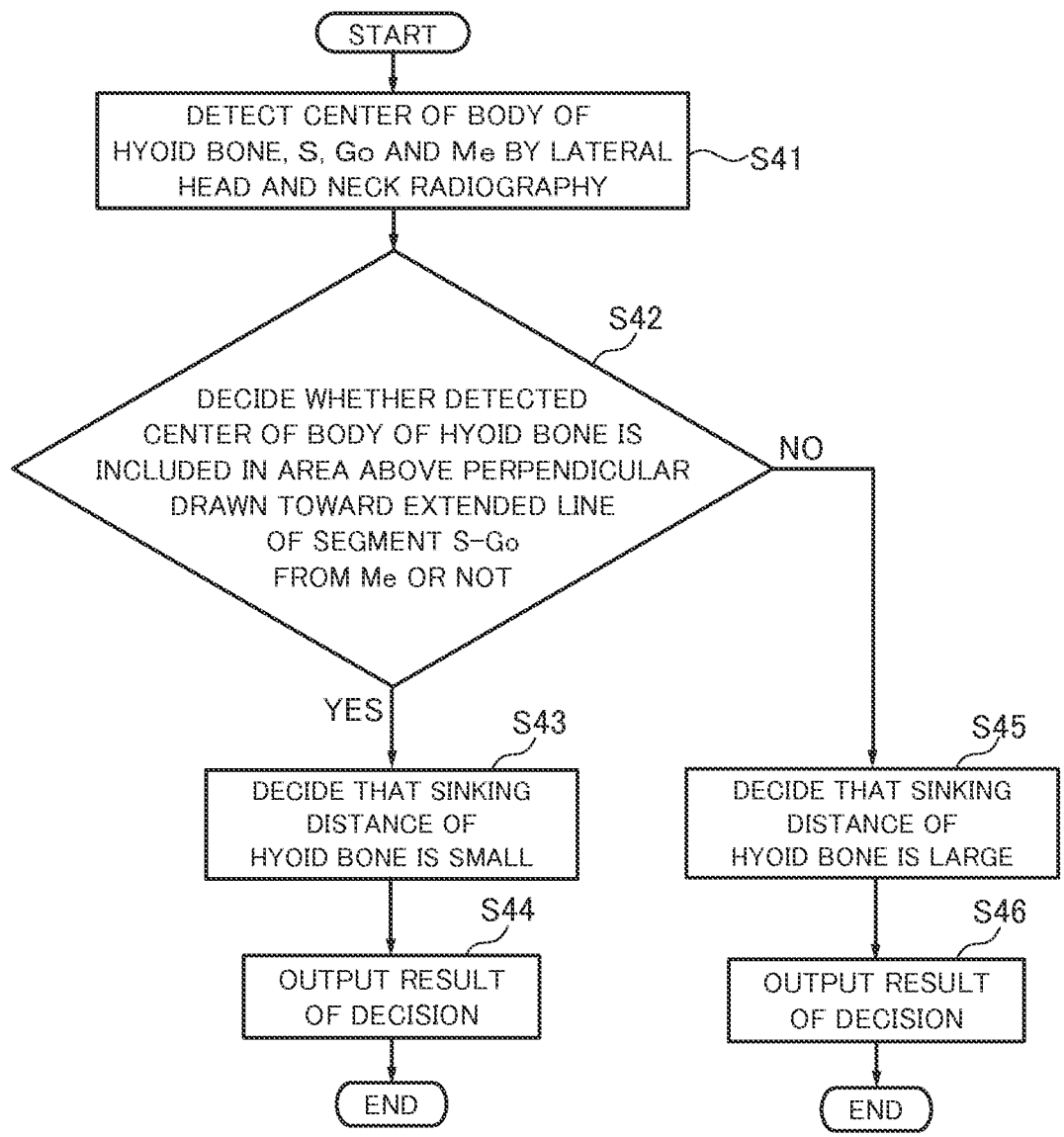
FIG. 33 A flowchart showing a method of deciding sinking of the hyoid bone according to the fifth embodiment of the invention.

FIG. 33 shows a flow chart of the method of deciding sinking of the hyoid bone. Programs are created according to the flow chat and are executed on a computer.

In step S41, lateral head and neck radiography of the subject is carried out and the center of the body of the hyoid bone, S, Go and Me are detected from the image. Radiography is carried out at centric occlusion or at a position near to it. Furthermore, radiography is carried out by setting the tilt in the front-rear direction of the head so that the Frankfort plane of the head of the subject becomes parallel to the floor surface.

Detection of the center of the body of the hyoid bone, S, Go and Me can be carried out as the same as the first embodiment.

In step S42, it is decided whether the detected center of the body of the hyoid bone is included in the area above the perpendicular drawn toward the extended line of the segment S-Go from Me or not.

When it is decided in step S42 that the detected center of the body of the hyoid bone is included in the area above the perpendicular drawn toward the extended line of the segment S-Go from Me, it is decided in step S43 that the sinking distance of the hyoid bone is small.

In step S44, the result of decision that the sinking distance of the hyoid bone is small is output to, for example, to the display.

When it is decided in step S42 that the center of the body of the hyoid bone is not included in the area above the perpendicular drawn toward the extend line of the segment S-Go from Me, it is decided in step S45 that the sinking distance of the hyoid bone is large.

In step S46, the result of decision that the sinking distance of the hyoid bone is large is output to, for example, the display.

According to the method of deciding sinking of the hyoid bone according to the fifth embodiment, based on the center of the body of the hyoid bone, S, Go and Me which are detected by lateral head and neck radiography, it is possible to decide the presence or absence or the degree of sinking of the hyoid bone objectively and in a short time with certain accuracy without depending on experiences etc. of a doctor.

6. The Sixth Embodiment

In the sixth embodiment, the method of deciding sinking of the hyoid bone based on lateral head and neck radiography of a subject is described.

Figure 34:
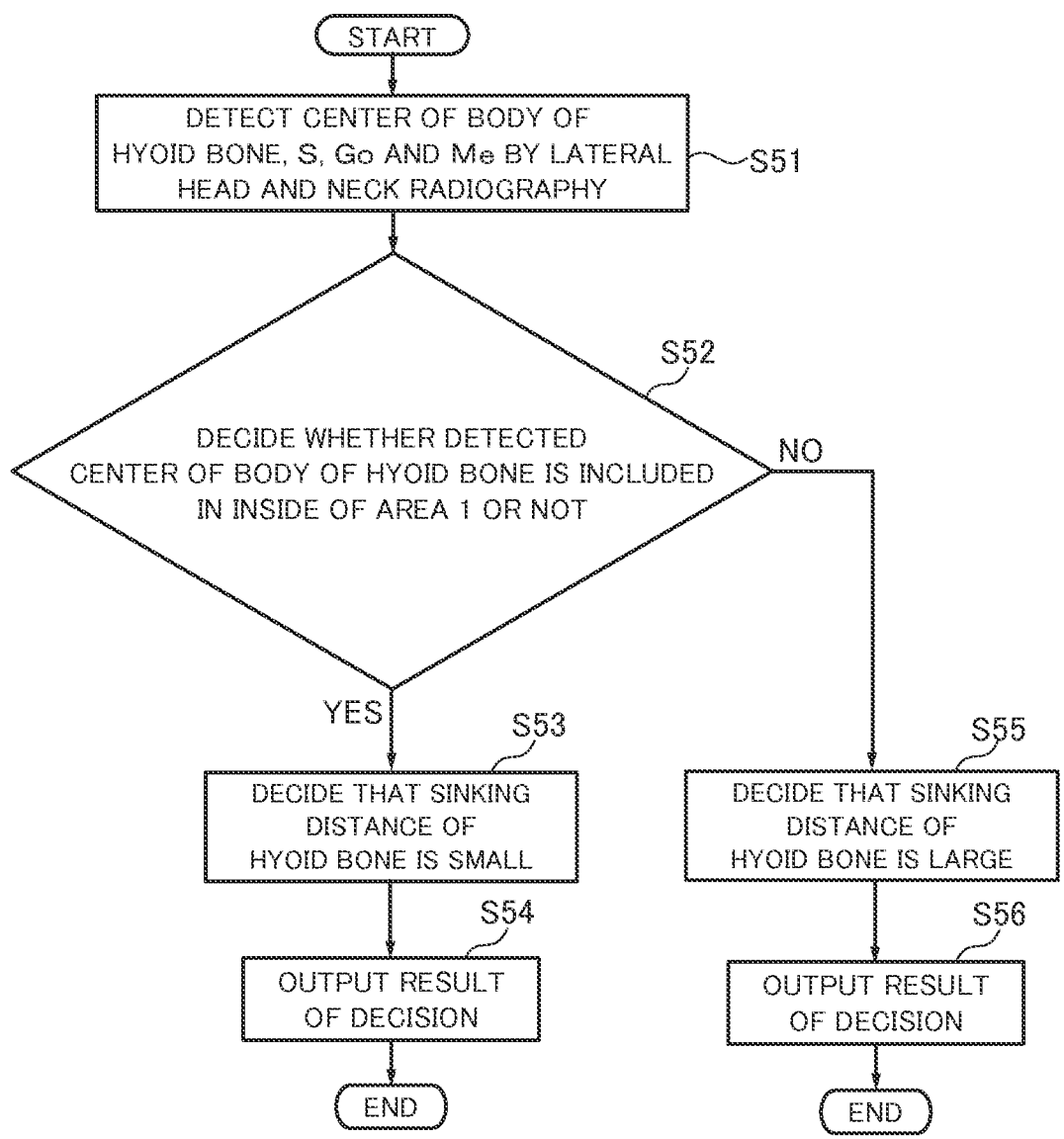
FIG. 34 A flowchart showing a method of deciding sinking of the hyoid bone according to the sixth embodiment of the invention.

FIG. 34 shows a flow chart of the method of deciding sinking of the hyoid bone. Programs are created according to the flowchart and are executed on a computer.

In step S51, lateral head and neck radiography of the subject is carried out and the center of the body of the hyoid bone, S, Go and Me are detected from the image. Radiography is carried out at centric occlusion or at a position near to it. Furthermore, the radiography is carried out by setting the tilt in the front-rear direction of the head so that the Frankfort plane of the head of the subject becomes parallel to the floor surface.

Detection of the center of the body of the hyoid bone, S, Go and Me can be carried out as the same as the first embodiment.

In step S52, it is decided whether the detected center of the body of the hyoid bone is included in the inside of the area 1 or not.

When it is decided in step S52 that the detected center of the body of the hyoid bone is included in the inside of the area 1, it is decided in step S53 that the sinking distance of the hyoid bone is small.

In step S54, the result of decision that the sinking distance of the hyoid bone is small is output to, for example, the display.

When it is decided in step S52 that the detected center of the body of the hyoid bone is not included in the inside of the area 1, in other words, it locates below the area 1, it is decided in step S55 that the sinking distance of the hyoid bone is large.

In step S56, the result of decision that the sinking distance of the hyoid bone is large is output to, for example, the display.

According to the method of deciding sinking of the hyoid bone according to the sixth embodiment, based on the center of the body of the hyoid bone, S, Go and Me which are detected by lateral head and neck radiography, it is possible to decide the presence or absence or the degree of sinking of the hyoid bone objectively and in a short time with certain accuracy without depending on experiences etc. of a doctor.

7. The Seventh Embodiment

In the seventh embodiment, a method of deciding sinking of the hyoid bone based on lateral head and neck radiography of a subject is described.

Figure 35:
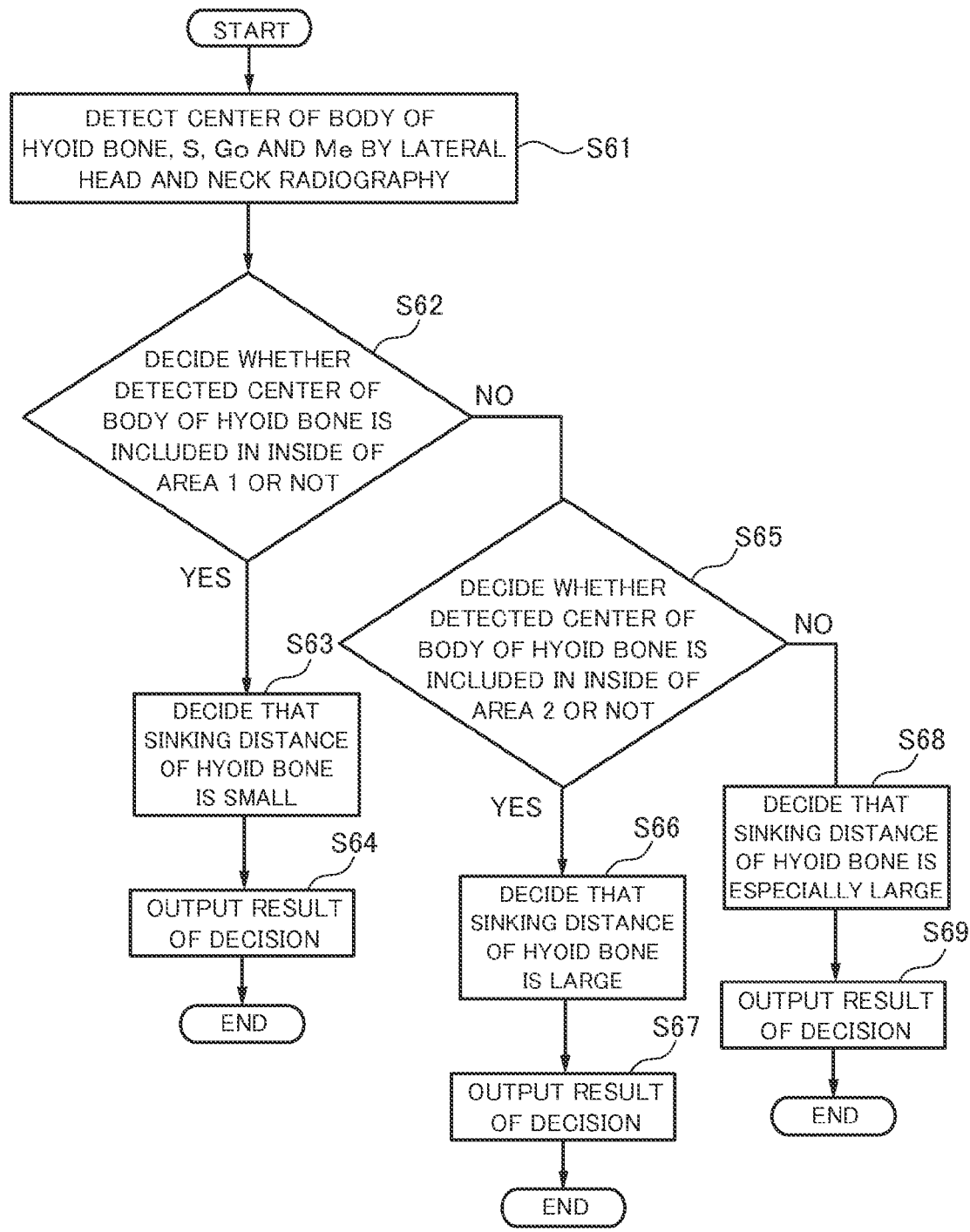
FIG. 35 A flowchart showing a method of deciding sinking of the hyoid bone according to the seventh embodiment of the invention.

FIG. 35 shows a flow chart of the method of deciding sinking of the hyoid bone. Programs are created according to the flowchart and are executed on a computer.

In step S61, lateral head and neck radiography of the subject is carried out and the center of the body of the hyoid bone, S, Go, Me and Cd are detected from the image. Radiography is carried out at centric occlusion or at a position near to it. Furthermore, radiography is carried out by setting the tilt in the front-rear direction of the head so that the Frankfort plane of the head of the subject becomes parallel to the floor surface.

Detection of the center of the body of the hyoid bone, S, Go, Me and Cd can be carried out as the same as the first embodiment.

In step S62, it is decided whether the detected center of the body of the hyoid bone is included in the inside of the area 1 or not.

When it is decided in step S62 that the detected center of the body of the hyoid bone is included in the inside of the area 1, it is decided in step S63 that the sinking distance of the hyoid bone is small.

In step S64, the result of decision that the sinking distance of the hyoid bone is small is output to, for example, the display.

When it is decided in step S62 that the detected center of the body of the hyoid bone is not included in the inside of the area 1, in other words, it locates below the area 1, it is decided in step S65 whether the center of the body of the hyoid bone is included in the inside of the area 2 or not.

When it is decided in step S65 that the detected center of the body of the hyoid bone is included in the inside of the area 2, it is decided in step S66 that the sinking distance of the hyoid bone is large.

In step S67, the result of decision that the sinking distance of the hyoid bone is large is output to, for example, the display.

When it is decided in step S65 that the detected center of the body of the hyoid bone is not included in the inside of the area 2, in other words, it locates below the area 2, that is, in the area 3, it is decided in step S68 that the sinking distance of the hyoid bone is especially large.

In step S69, the result of decision that the sinking distance of the hyoid bone is especially large is output to, for example, the display.

According to the method of deciding sinking of the hyoid bone according to the seventh embodiment, based on the center of the body of the hyoid bone, S, Go, Me and Cd which are detected by lateral head and neck radiography, it is possible to decide the presence or absence or the degree of sinking of the hyoid bone objectively and in a short time with certain accuracy without depending on experiences etc. of a doctor.

8. The Eighth Embodiment

In the eighth embodiment, described is an X-ray diagnostic system capable of carrying out the methods of deciding the risk of obstructive sleep apnea syndrome or the methods of deciding sinking of the hyoid bone according to the first to the seventh embodiments.

That is, the X-ray diagnostic system has a computer having the stored programs to carry out one or more among the methods of deciding the risk of obstructive sleep apnea syndrome or the methods of deciding sinking of the hyoid bone according to the first to the seventh embodiments based on the image taken by lateral head and neck radiography, posteroanterior head and neck radiography and anteroposterior head and neck radiography.

According to the eighth embodiment, by carrying out any one of lateral head and neck radiography, posteroanterior head and neck radiography and anteroposterior head and neck radiography and carrying out one or more among the methods of deciding the risk of obstructive sleep apnea syndrome or the methods of deciding sinking of the hyoid bone according to the first to the seventh embodiments based on the obtained image, it is possible to decide the risk of becoming OSAS or the presence or absence or the degree of sinking of the hyoid bone of the subject.

9. The Ninth Embodiment

In the ninth embodiment, described is a cephalometric radiographic apparatus which is preferably used for lateral head and neck radiography, posteroanterior head and neck radiography and anteroposterior head and neck radiography of the subject in the methods of deciding the risk of obstructive sleep apnea syndrome or the methods of deciding sinking of the hyoid bone according to the first to the seventh embodiments. By combining a computer having the stored programs to carry out one or more among the methods of deciding the risk of sleep apnea syndrome or the methods of deciding sinking of the hyoid bone according to the first to the seventh embodiments with the cephalometric radiographic apparatus, it is possible to construct the X-ray diagnostic system capable of deciding the risk of obstructive sleep apnea syndrome or deciding sinking of the hyoid bone.

Figure 36:
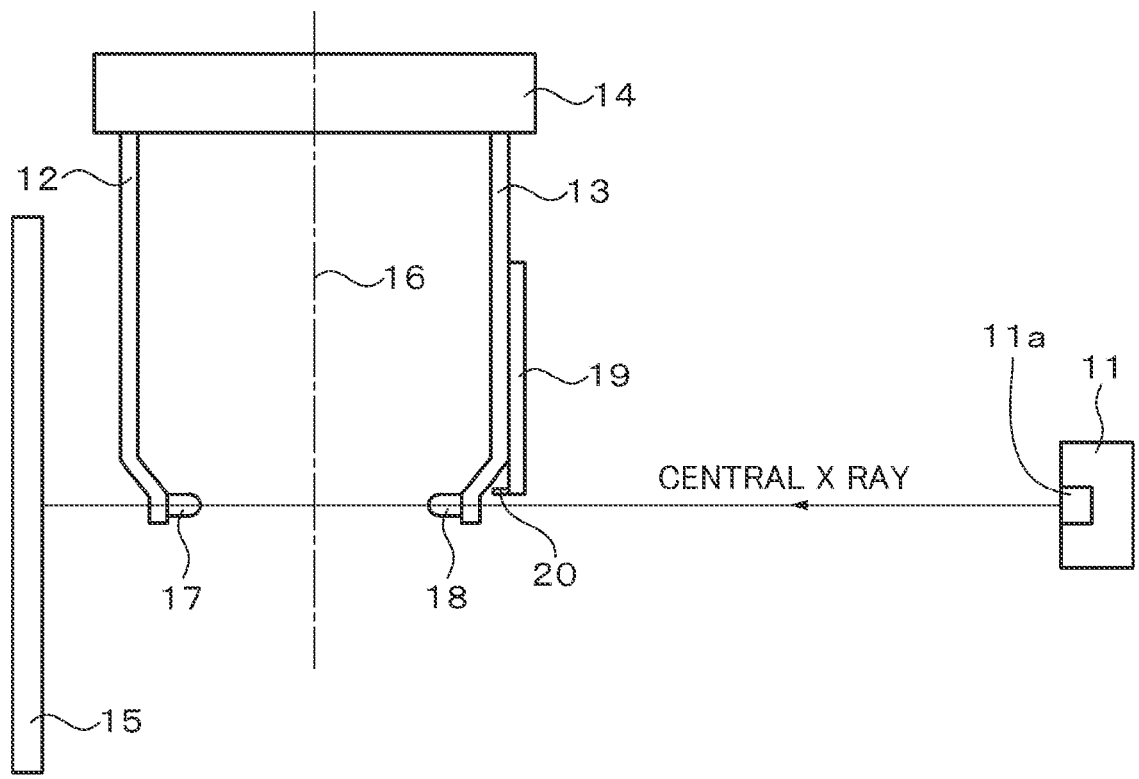
FIG. 36 A schematic drawing looking at a cephalometric radiographic apparatus according to the ninth embodiment that is preferably applied to lateral head and neck radiography, posteroanterior head and neck radiography and anteroposterior head and neck radiography in the first to the seventh embodiments of the invention.

FIG. 36 shows the cephalometric radiographic apparatus according to the ninth embodiment. As shown in FIG. 36, the cephalometric radiographic apparatus has an X-ray generator 11, arms 12 and 13, an arm control device 14, and an X-ray detector 15. The X-ray generator 11 has an X-ray tube 11a, and from the X-ray tube 11a, X rays are generated. The arm control device 14 is supported for the floor surface by a support part of which drawing is omitted.

The X rays generated from the X-ray tube 11a are irradiated to the head of a subject, the X rays transmitted through the head enter into the X-ray detector 15, and the transmission X-ray image is obtained. The X-ray detector 15 is not specifically limited, but, for example, an X-ray film, an imaging plate, a semiconductor detector, etc. are used. The transmission X-ray image is, as necessary, converted to a digital image signal, for example. Although not illustrated, the transmission X-ray image obtained in the X-ray detector 15 is taken in an image collecting part.

The arms 12 and 13 are provided facing each other with a reference line 16 parallel to the vertical line and perpendicular to the central X ray therebetween. The upper parts of the arms 12 and 13 are fixed to the arm control device 14. And by the arm control device 14, the arms 12 and 13 are able to rotate around the reference line 16, move up and down in a parallel direction to the reference line 16, and move translatory in an opposite direction each other in the horizontal direction. The width of the lower parts of the arms 12 and 13 becomes gradually narrowing towards the bottom edge, and the bottom edge has a circular shape (see FIG. 37). Also, the bottom edges of the arms 12 and 13, after folded back at a predetermined angle inward to the vertical line respectively, again becomes parallel to the vertical line. At least the parts of the arms 12 and 13 irradiated by X-rays at the time of taking a radiograph are constituted of transparent materials. Generally, almost all the parts of the arms 12 and 13 are constituted of the transparent materials. The inside surfaces facing each other of the bottom edges of the arms 12 and 13 are respectively provided concentrically with column-shaped ear rods 17 and 18 with pointed tips. As the ear rods 17 and 18, publicly known ear rods can be used. The outlines of the ear rods 17 and 18 come out at the time of taking a radiograph.

At least on one of the exterior surfaces of the arms 12 and 13, a head tilt setting device 19 for setting the tilt in the front-rear direction of the head of a subject is fixed. In FIG. 36, an example that the head tilt setting device 19 is fixed to the exterior surface of the arm 13 is shown. In this case, the head tilt setting device 19 is constituted of a rectangular transparent plate vertical to the central axis of the ear rod 18. As the transparent plate, a transparent plastic plate such as an acrylic plate, a PET (polyethylene terephthalate) plate, etc. or a glass plate, etc. can be used. The transparent plate may be that a necessary mechanical strength can be obtained, and thickness is enough not to fold easily. The thickness of the transparent plate may be, for example, 2 mm or more and 10 mm or less. The method of fixing the head tilt setting device 19 is not specifically limited, but may be adhesion, screwed down, clip-on, etc.

Figure 37:
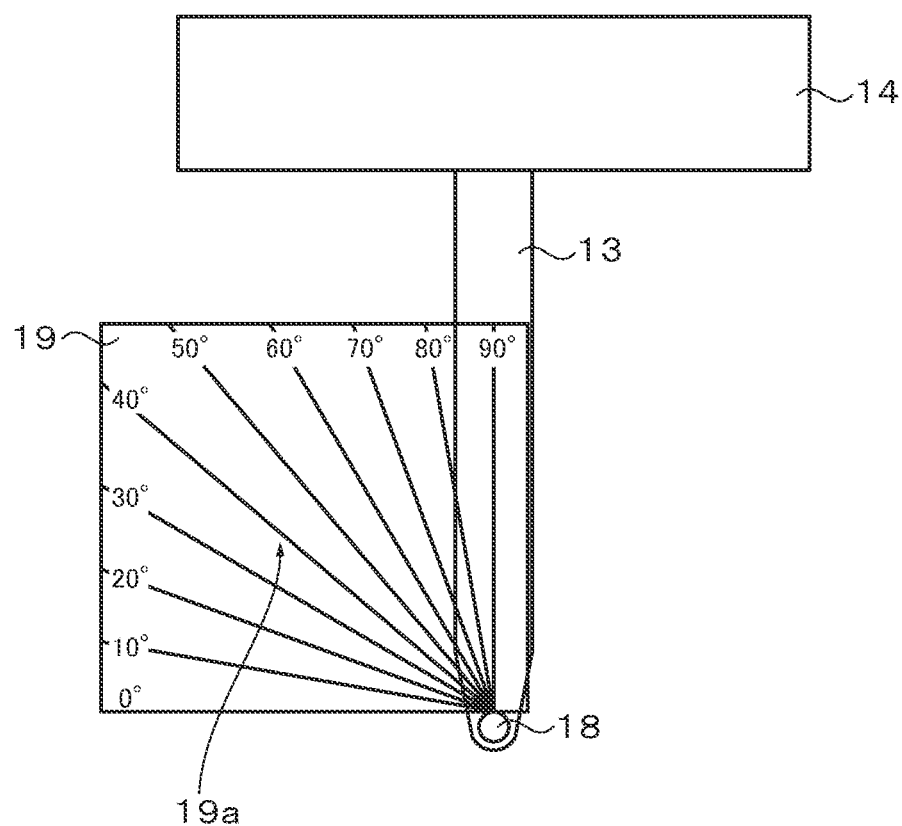
FIG. 37 A schematic drawing showing an arm of the cephalometric radiographic apparatus shown in FIG. 36 and a head tilt setting device provided on the arm.
Figure 38:
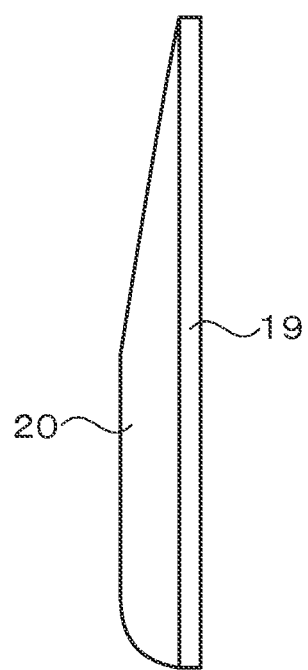
FIG. 38 A plan view showing a horizontal plate provided at the bottom edge of the head tilt setting device of the cephalometric radiographic apparatus shown in FIG. 36.

The details of the head tilt setting device 19 are shown in FIG. 37. FIG. 37 is a drawing looking at the head tilt setting device 19 from the vertical direction to the surface. As shown in FIG. 37, the bottom edge surface (the base) of the head tilt setting device 19 is parallel to the horizontal plane. The bottom edge surface of the head tilt setting device 19 coincides with the tangential direction drawn toward the vertical direction to the central axis of the ear rod 18 at the uppermost point of the ear rod 18. At the head tilt setting device 19, an angle scale 19a centered on the uppermost point of the ear rod 18 is formed, and has the function of a protractor. In FIG. 37, the angle scale 19a is formed from 0° to 90° marked every 10°, but a method of marking the angle scale 19a is not limited to this. For example, the angle scale 19a may be formed, marked every 5° or 1°. Or the angle scale 19a may be formed only within a specific angle range, for example, from 0° to 30°. The line at a 0° of the angle scale 19a coincides with the bottom edge surface of the head tilt setting device 19. The angle scale 19a is typically formed with a black colored line as the same as a general protractor, for example, but is not limited to this. The angle scale 19a except for the 0° may be provided on one surface of the head tilt setting device 19 and is preferably provided respectively on the corresponding position each other to both surfaces. Like this, by providing the angle scale 19a at the corresponding position each other to the both surfaces of the head tilt setting device 19, when looking at the angle scale 19a from the horizontal direction, the direction that the angle scales 19a of the both surfaces coincide is the horizontal direction, and in case not coinciding, it can be judged to go off from the horizontal direction. At the bottom edge surface of the head tilt setting device 19, a horizontal plate 20 protruding inward vertically to the head tilt setting device 19 is provided. FIG. 38 shows a plan view of the head tilt setting device 19 and the horizontal plate 20. As shown in FIG. 38, the horizontal plate 20 has a wide part at the part distant from the ear rod 18. In order to make the visual confirmation easy when confirming the horizontal plane, the horizontal plate 20 is preferably colored, specifically, for example, is colored in black. Materials, thickness, width in the horizontal direction, etc. of the horizontal plate 20 are selected, preferably so as to come out to the X-ray transmission images. The materials of the horizontal plate 20 are, for example, transparent plastics such as acryl, etc., opaque plastics, metal, etc. The thickness of the horizontal plate 20 is, for example, 0.2 mm or more and 2 mm or less, but is not limited to this. The width in the horizontal direction of the horizontal plate 20 is, for example, 1 mm or more and 30 mm or less, but not limited to this.

Next, a method of taking a head and neck radiograph of a subject using the cephalometric radiographic apparatus will be explained.

(1) A Method of Taking a Lateral Head and Neck Radiograph

Figure 39:
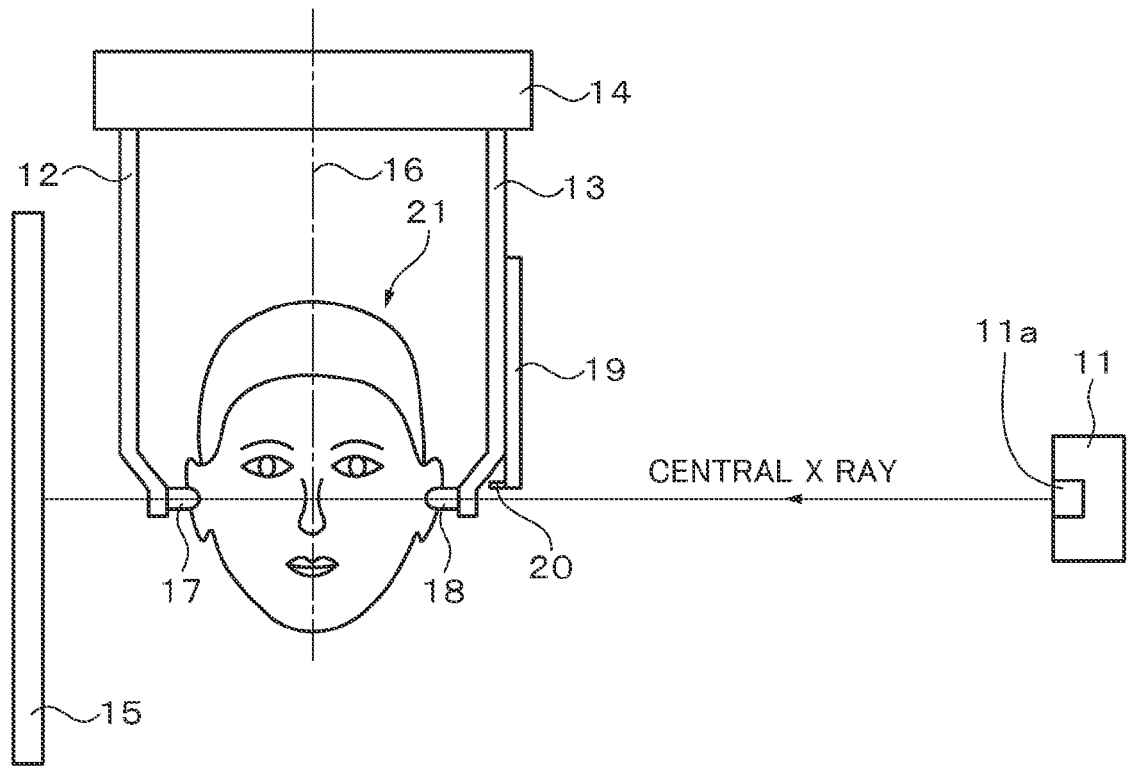
FIG. 39 A schematic drawing for explaining a method of taking a lateral head and neck radiograph using the cephalometric radiographic apparatus shown in FIG. 36.
Figure 40:
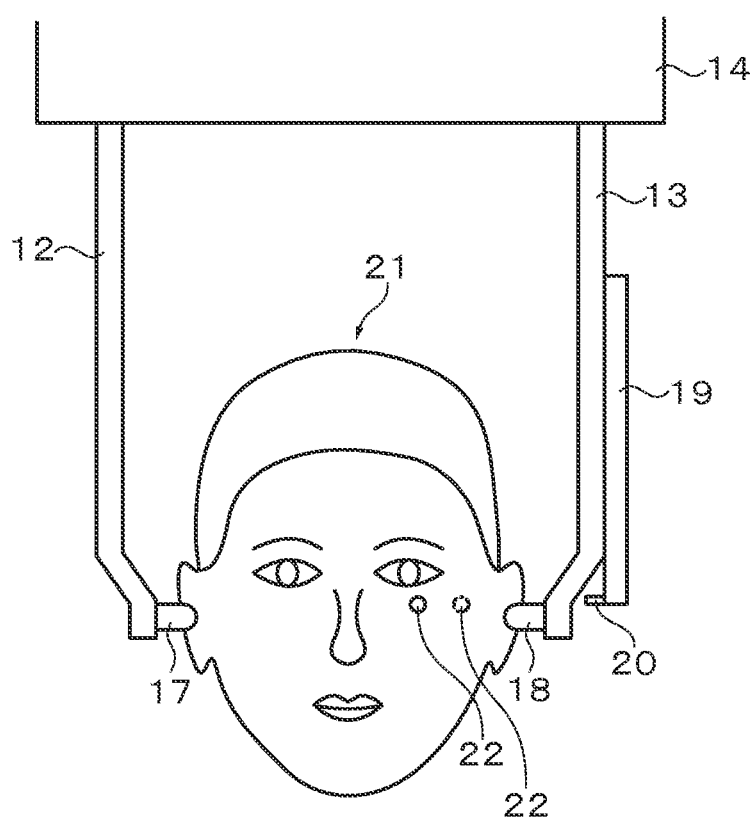
FIG. 40 A schematic drawing for explaining a method of taking a lateral head and neck radiograph using the cephalometric radiographic apparatus shown in FIG. 36.
Figure 41:
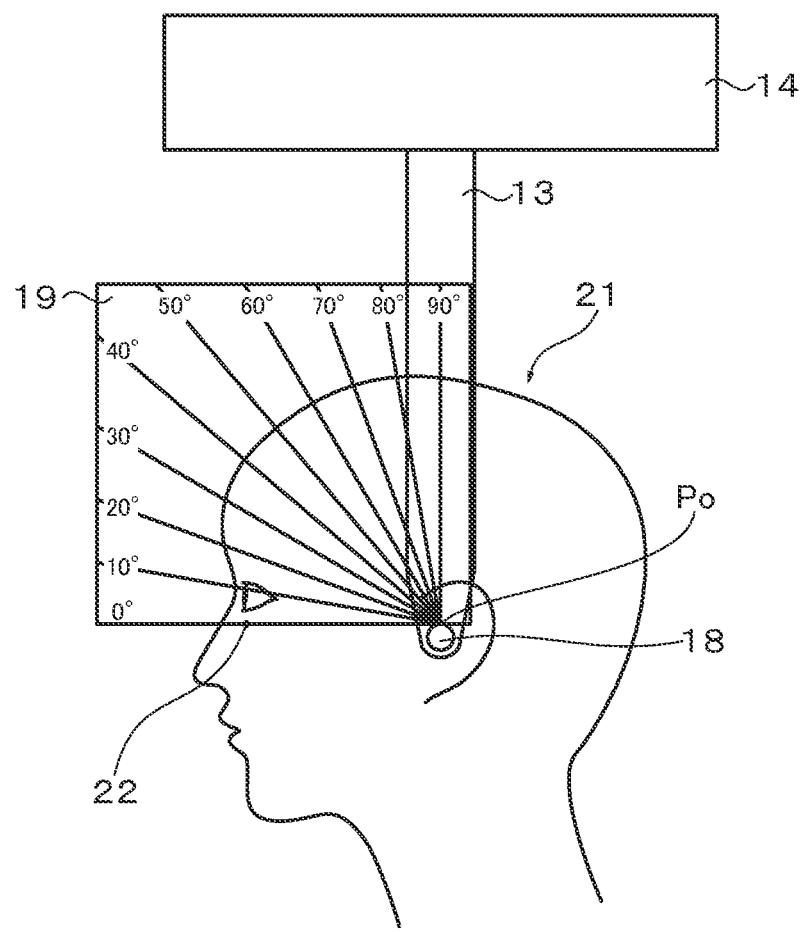
FIG. 41 A schematic drawing for explaining a method of taking a lateral head and neck radiograph using the cephalometric radiographic apparatus shown in FIG. 36.

In FIG. 36, the arms 12 and 13 are made to move translatory to the outside in the horizontal direction, well away from each other, and to move to a high enough position. Under the state, as shown in FIG. 39, the head 21 of a subject is positioned between the arms 12 and 13 so that its median sagittal plane becomes vertical to the central X ray from the X-ray tube 11a. The subject may be in a sitting position, sitting on a chair or in a standing position, standing up. Next, by descending the arms 12 and 13, the ear rods 17 and 18 are made to come to the position of the height of the right and left external acoustic openings of the head 21 of the subject. Next, the arms 12 and 13 are made to move translatory inward in the horizontal direction, and the ear rods 17 and 18 are inserted in the right and left external acoustic openings of the head 21 of the subject. And by making the uppermost points of the ear rods 17 and 18 contact with the portions, the head 21 is fixed so that the irradiation direction of the central X-ray coincides with the central axis of the ear rods 17 and 18. Next, an inspector searches for a predetermined reference point (the second reference point) of the face of the head 21, for example, the orbitale (Or), the orbital margin just under the center of the pupil, the center of the palpebral fissure, etc. For example, when making the orbitale as a reference point, the inspector can search by touching the vicinity of the infraorbital margin with a fingertip. And as shown in FIG. 40, a circular small colored seal 22 is put on the reference point that is searched for like this. The color of the seal 22 may be basically any color, but, for example, may be red, yellow, green, blue, white, black, etc. In case that it is difficult to look the seal 22 put on the reference point from the lateral direction of the head 21, another seal 22 is also put on the outside of the horizontal direction from the seal 22 on the face, for example, at the position apart from 5 to 20 mm. Next, as shown in FIG. 41, the inspector looks at the head tilt setting device 19 in the horizontal direction from the outside. At this time, the seal 22 can be seen through the head tilt setting device 19 made of the transparent plate. And, using the angle scale 19a of the head tilt setting device 19, a straight line connecting the portion (that coincides with the uppermost point of the ear rod 18) with the orbitale is set at an intended angle. In FIG. 41, as an example, a case where a plane connecting the portion with the orbitale, that is, the Frankfort plane is set horizontally. In case the Frankfort plane is set horizontally like this, the horizontal plate 20 that coincides with a 0° of the angle scale 19a is observed from the outside. In case the horizontal plate 20 is seen like a line, the observation is made from the horizontal direction, and the tilt in the front-rear direction of the head 21 is set so that the straight line connecting the portion with the orbitale coincides with the horizontal plate 20. Thus, the Frankfort plane of the head 21 is set to parallel to the horizontal plane (floor surface).

By taking a radiograph under the state that the tilt of the head 21 is set at an intended tilt as mentioned above, a lateral head and neck radiograph is taken.

Figure 42:
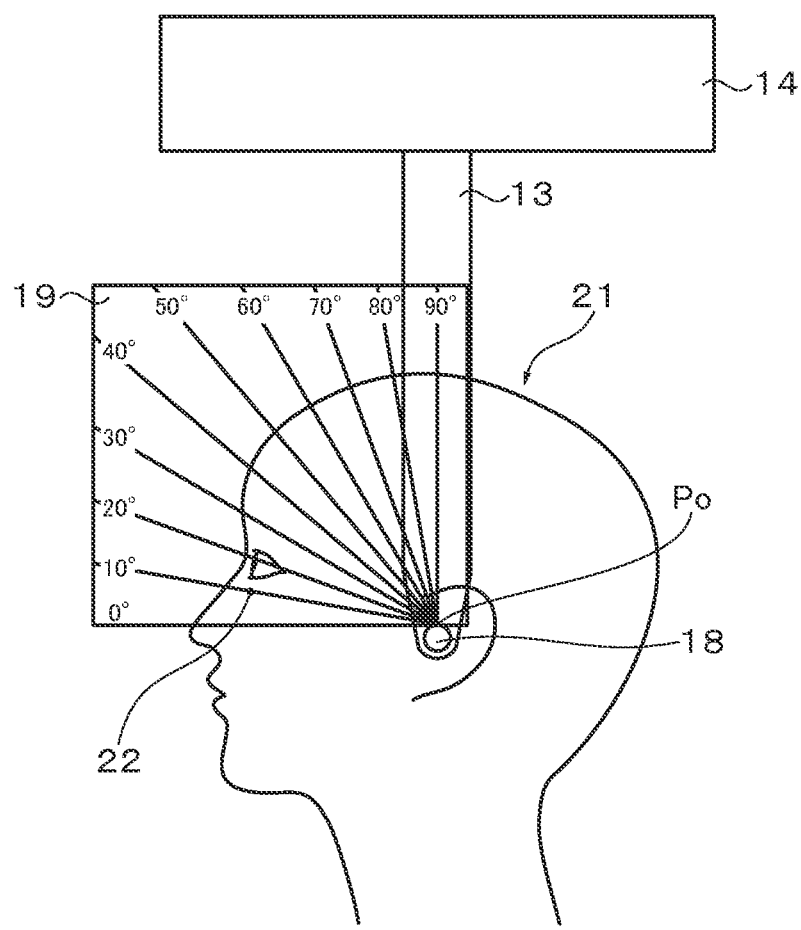
FIG. 42 A schematic drawing for explaining a method of taking a lateral head and neck radiograph, facing the face upward and tilting the head at a 10° in the front-rear direction using the cephalometric radiographic apparatus shown in FIG. 36.

As an example of taking a lateral head and neck radiograph at the position that the Frankfort plane of the head 21 is tilted at positive or negative angle to the horizontal plane, a case of taking a lateral head and neck radiograph under the state that the Frankfort plane of the head 21 is tilted at a 10° (the face faces upward) to the horizontal plane is shown in FIG. 42. As shown in FIG. 42, in this case, using the angle scale 19a of the head tilt setting device 19, adjusting the tilt in the front-rear direction of the head 21, the straight line connecting the portion with the orbitale is set at an angle of 10°.

(2) A Method of Taking a Posteroanterior Head and Neck Radiograph

Figure 43:
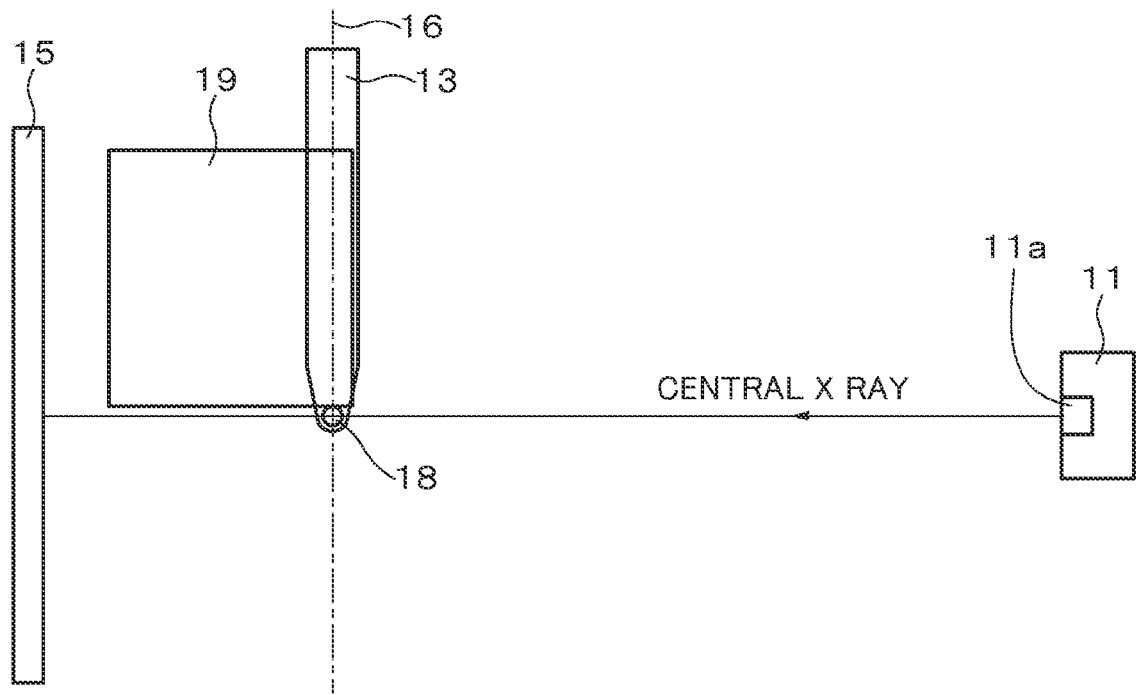
FIG. 43 A schematic drawing for explaining a method of taking a posteroanterior head and neck radiograph using the cephalometric radiographic apparatus shown in FIG. 36.
Figure 44:
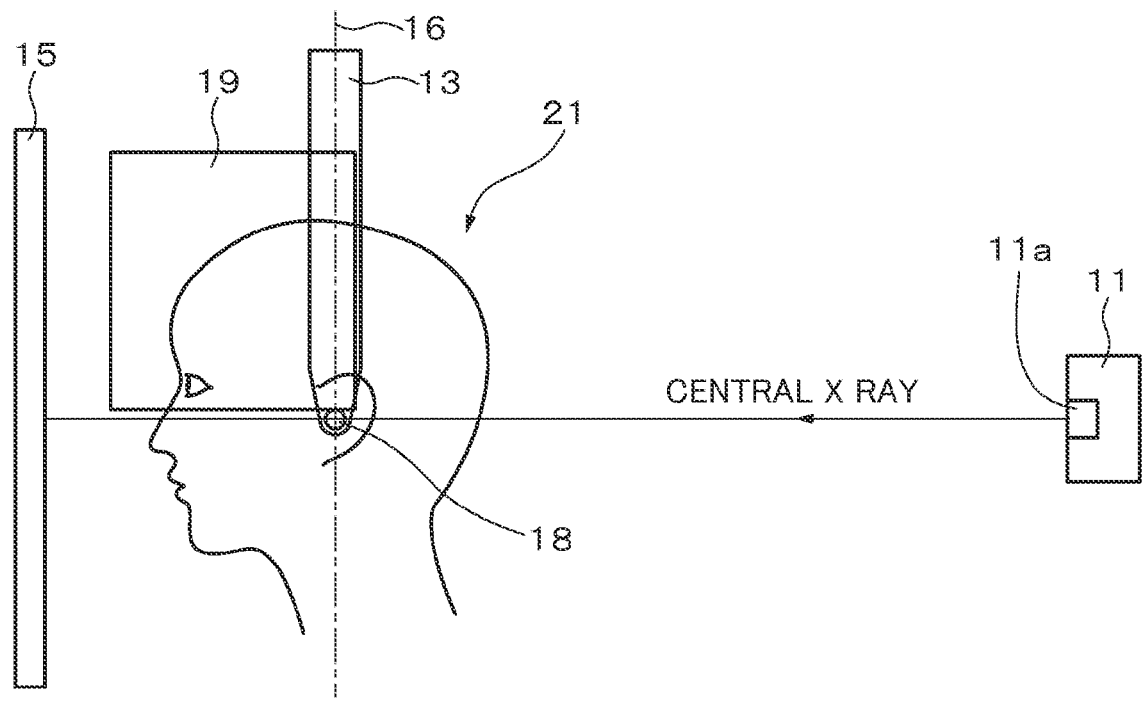
FIG. 44 A schematic drawing for explaining a method of taking a posteroanterior head and neck radiograph using the cephalometric radiographic apparatus shown in FIG. 36.

As shown in FIG. 43, the arms 12 and 13 are rotated 90° around the reference line 16 from the position shown in FIG. 36. And as shown in FIG. 44, as the same as the case of taking a lateral head and neck radiograph, inserting the ear rods 17 and 18 in the right and left external acoustic openings of the head 21 of a subject, and by contacting the uppermost point of the ear rods 17 and 18 with the portion, the head 21 is fixed. In this case, the face of the head 21 faces the X-ray detector 15. Also, the irradiation direction of the central X ray intersects at right angles with the central axis of the ear rods 17 and 18. On the predetermined reference point of the face of the head 21, specifically, for example, on the orbitale, the seal 22 is kept putting. Next, the inspector looks at the head tilt setting device 19 from the outside in the horizontal direction. At this time, the seal 22 can be seen through the head tilt setting device 19. And, as the same as the case of taking a lateral head and neck radiograph, using the angle scale 19a of the head tilt setting device 19, the straight line connecting the portion with the orbitale is set at the same angle as in the case of taking the lateral head and neck radiograph. And, by taking a radiograph at the position, the posteroanterior head and neck radiograph can be taken under the state that the tilt in the front-rear direction of the head 21 is the same as when taking the lateral head and neck radiograph. For example, a lateral head and neck radiograph and also a posteroanterior head and neck radiograph can be taken at the position that the Frankfort plane of the head 21 becomes parallel to the horizontal plane (floor surface).

(3) A Method of Taking an Anteroposterior Head and Neck Radiograph

A method of taking an anteroposterior head and neck radiograph is the same as the method of taking a posteroanterior head and neck radiograph, except that the head 21 is positioned so that the face of the head 21 faces to the X-ray generator 11.

By the cephalometric radiographic apparatus according to the ninth embodiment, the following various advantages can be obtained. That is, using the head tilt setting device 19, the tilt in the front-rear direction of the head 21 at the time of taking a radiograph can be set at the intended tilt. By this, a lateral head and neck radiograph, a posteroanterior head and neck radiograph, an anteroposterior head and neck radiograph, a head and neck radiograph in any direction between the posteroanterior direction and anteroposterior direction, etc. can be taken easily and with high reproducibility under the same state of the tilt in the front-rear direction of the head 21 of a subject. For this, it is possible to improve reliability of detection of the positions of the center of the body of the hyoid bone, S, Go, Me and Cd based on lateral head and neck radiography, posteroanterior head and neck radiography and anteroposterior head and neck radiography in the methods of deciding the risk of obstructive sleep apnea syndrome or the methods of deciding sinking of the hyoid bone according to the first to the second embodiments, resulting improvement of reliability of the decision of the risk of obstructive sleep apnea syndrome or the decision of sinking of the hyoid bone. Furthermore, for example, when taking a lateral head and neck radiograph or a posteroanterior head and neck radiograph at different time, for example, when taking a radiograph one year after from a certain time taking a radiograph, a radiograph can be taken under the same state of the tilt in the front-rear direction of the head 21. Like this, because of being able to take a radiograph any time under the same tilt in the front-rear direction of the head 21, the superposition of a lateral head and neck radiograph or an anteroposterior head and neck radiograph can be made easily. By this, the aging of the hyoid bone or the maxilla and mandible of the head 21 can be investigated correctly, and the growth and development or change of the position of the hyoid bone or the growth and development of the maxilla and mandible can be investigated correctly.

Example 3

Figure 45:
FIG. 45 A substitute picture for a drawing showing a lateral head and neck radiograph of a subject 23 taken by using the cephalometric radiographic apparatus shown in FIG. 36.
Figure 46:
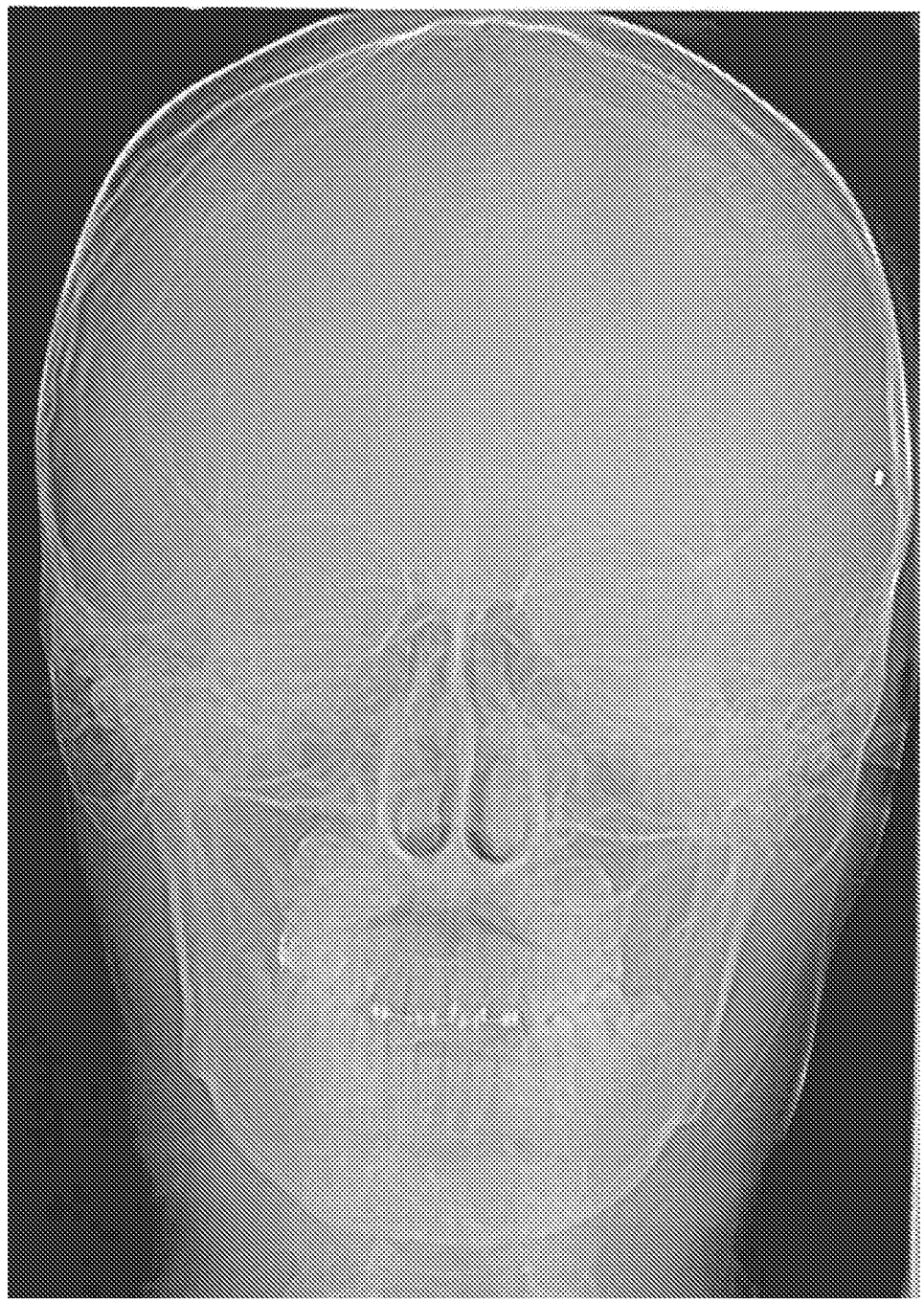
FIG. 46 A substitute picture for a drawing showing a posteroanterior head and neck radiograph of the subject 23 taken by using the cephalometric radiographic apparatus shown in FIG. 36.
Figure 47:
FIG. 47 A substitute picture for a drawing showing a lateral head and neck radiograph of a subject 24 taken by using the cephalometric radiographic apparatus shown in FIG. 36.
Figure 48:
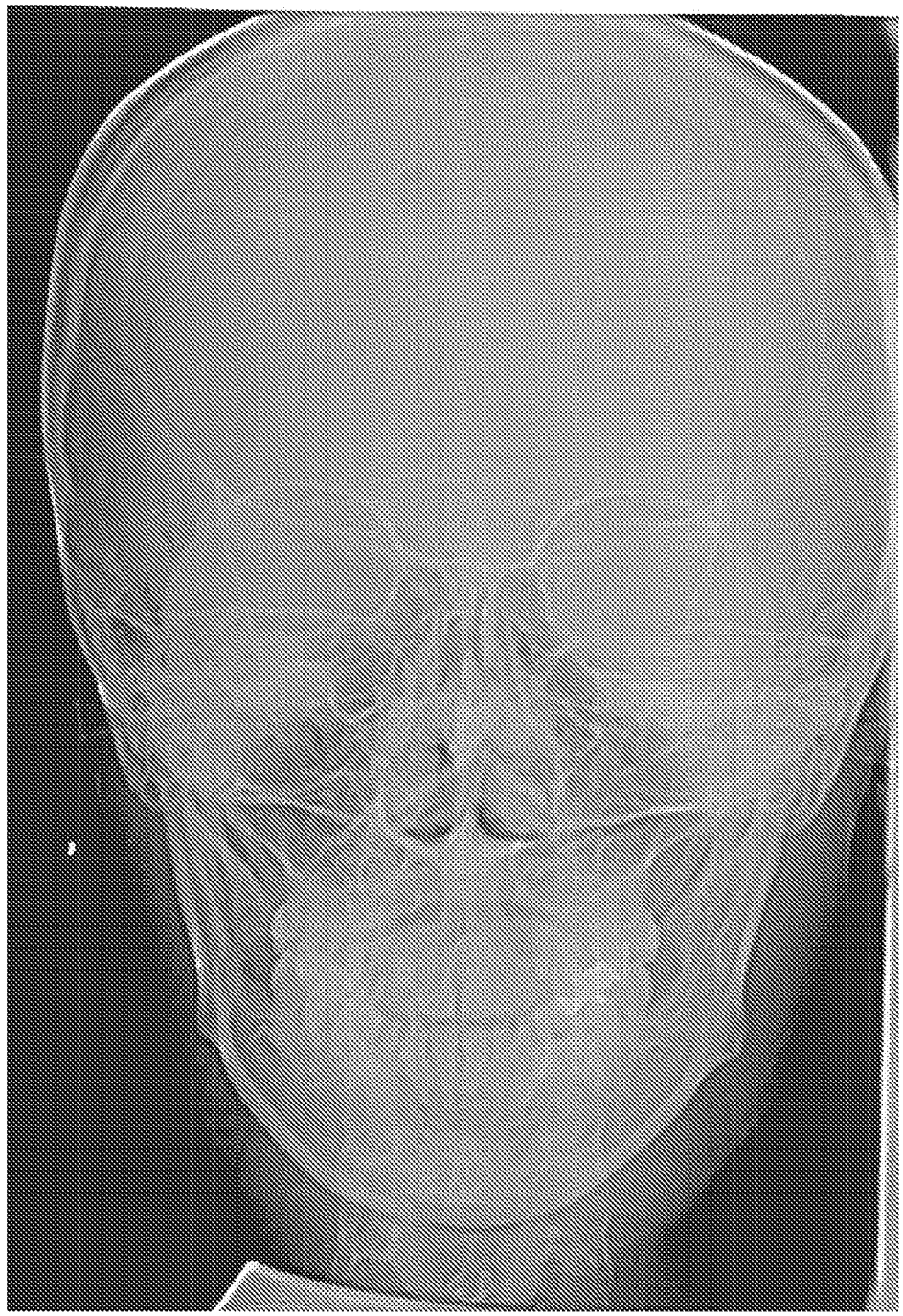
FIG. 48 A substitute picture for a drawing showing a posteroanterior head and neck radiograph of the subject 24 taken by using the cephalometric radiographic apparatus shown in FIG. 36.

By using the head tilt setting device 19, the lateral head and neck radiographs and the posteroanterior head and neck radiographs of the subjects 23 and 24 were taken at the position that the Frankfort plane of the head 21 is parallel to the floor surface. The radiographs were taken at centric occlusion or a position near to it. FIG. 45 and FIG. 47 show the lateral head and neck radiograph of the subjects 23 and 24, respectively. Here, the lateral white lines seen in FIG. 45 and FIG. 47 are the images of the horizontal plate 20 provided at the bottom edge of the head tilt setting device 19, and show the Frankfort plane. Also, FIG. 46 and FIG. 48 show the posteroanterior head and neck radiographs of the subjects 23 and 24, respectively.

From FIG. 45 to FIG. 48, of all of these subjects 23 and 24, it is known that the lateral head and neck radiographs and the anteroposterior head and neck radiographs can be taken at the position that the Frankfort plane of the head is parallel to the floor surface.

10. The Tenth Embodiment

The methods of deciding the risk of obstructive sleep apnea syndrome according to the first to the fourth embodiments are methods of deciding the risk of becoming OSAS in view of the position of the hyoid bone. It is more effective to combine the methods with a method of deciding the risk of obstructive sleep apnea syndrome which decides the risk of becoming OSAS in view of skeletal pattern of the jaw. Described now is the method of deciding the risk of obstructive sleep apnea syndrome which decides the risk of becoming OSAS in view of skeletal pattern of the jaw.

In the process of earnest study, the inventor of the present invention measured the distances between the specific measured points in a cephalometric radiogram for patients who were diagnosed as obstructive sleep apnea syndrome and subjects without respiratory disorder and found that the distribution of the numerals obtained by calculation based on the special equations using the distances was definitely different between them.

More specifically, according to the method of deciding the risk of obstructive sleep apnea syndrome comprises steps of:

using distances selected from a group consisting of the distance (S-A) between S and A, the distance (S-B) between S and B, the distance (Go-A) between Go and A, the distance (Go-B) between Go and B, the distance (Go-Me) between Go and Me and the distance (Cd-Go) between Cd and Go which are measured by cephalometric radiography of a subject, calculating P by at least one equation among equations (1) to (6), or when calculating P by the equation (1) or (2), further omitting the figures of the fourth decimal place and under of P/4 and calculating $$Q=(P/4)\times 1000,$$

when calculating P by the equation (3), further omitting the figures of the fourth decimal place and under of P and calculating $$Q=(P-[P])\times 1000 \ ([ \ ] \text{ denotes Gauss's symbol})$$
$$(\text{where } 2.000 \leq P < 3.000)$$

or $$Q=(P-([P]+1))\times 1000 \ ([ \ ] \text{ denotes Gauss's symbol})$$
$$(\text{where } P < 2.000),$$

when calculating P by equation (5) or (6), further omitting the figures of the fourth decimal place and under of P and calculating $$Q=P\times 1000; \text{ and}$$

deciding the risk of obstructive sleep apnea syndrome of the subject by comparing the calculated P or Q with the predetermined value, respectively.

$$P=((S-B)+(Go-B)+(Cd-Go))/(S-A) \qquad (1)$$

$$P=((S-B)+(Go-Me)+(Cd-Go))/(S-A) \qquad (2)$$

$$P=((S-B)+(Go-Me))/(S-A) \qquad (3)$$

$$P=(Go-A)-(Go-B) \qquad (4)$$

$$P=((Go-A)-(Go-B))/(Go-A) \qquad (5)$$

$$P=((Go-A)-(Go-B))/(Go-B) \qquad (6)$$

With respect to processing of the decimal of P/4 or P, any method other than the method omitting the figures of the fourth decimal place and under may be used.

Figure 49:
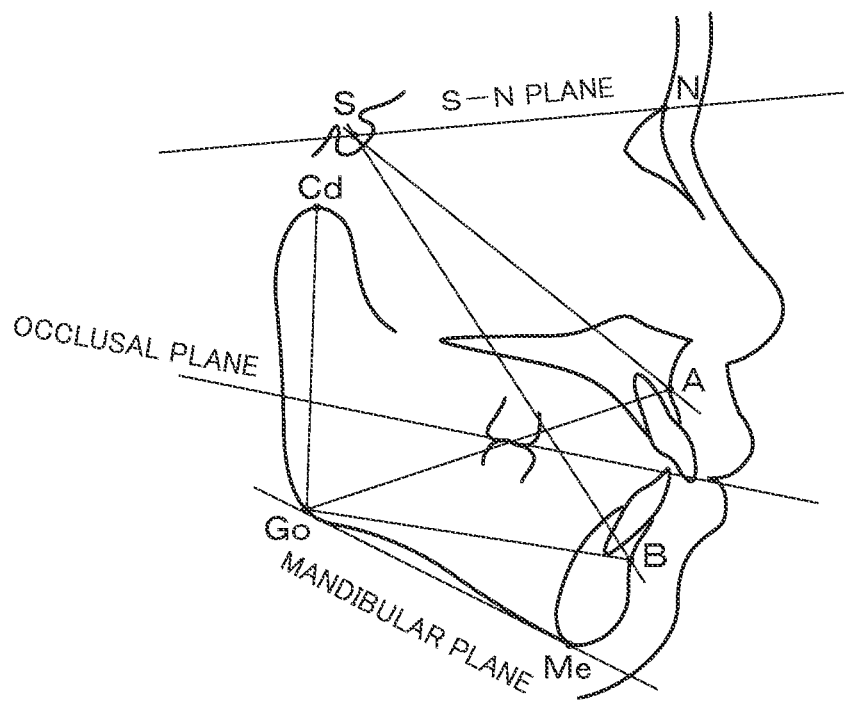
FIG. 49 A schematic drawing for explaining the measured points in a cephalometric radiogram.

Here, S, A, B, Go, Me and Cd are measured points to be obtained by cephalometric radiography. The positions of each measured point are shown in FIG. 49. S, Go, Me and Cd are described previously. "A" is an abbreviation of the point A, and is the deepest point on the median sagittal plane between ANS (the forefront of the anterior nasal spine, an abbreviation of an anterior nasal spine which is the forefront part of the palatine shelf of maxilla) and the Prosthion which is the most frontal point of an alveolar process between the upper central incisors. "B" is an abbreviation of the point B, and is the deepest point between the Infradentale, the most front point of an alveolar process between the lower central incisors and pogonion (the most protruding point of protuberantia mentalis of the mandible for the Frankfort plane). Although the details will be described later, the equation (3) can be more generally expressed by an equation $P=((S-X_i)+(Go-X_j))/(S-A)$ using the distance $(S-X_i)$ between S and $X_i$ (i is an integer from 1 to 4. $X_1$=B, $X_2$=Pog, $X_3$=Gn and $X_4$=Me.) and the distance $(Go-X_j)$ between Go and X (j is an integer from 1 to 4. j=i or j≠i.).

The inventor of the present invention measured the distances (S-A), (S-B), (Go-B) and (Cd-Go) in cephalometric radiograms of many patients of obstructive sleep apnea syndrome and calculated the equation (1). As a result, it was found that the majority of the patients of obstructive sleep apnea syndrome were to be in the range of 2.800≤P<3.200. This was the same for the case where the distances (S-A), (S-B), (Go-Me) and (Cd-Go) were measured and the equation (2) is calculated. As the index for deciding the risk of obstructive sleep apnea syndrome, P itself may be used, but the presentation of integers is easy to understand. For this, typically, for example, after calculating P, further omitting the figures of the fourth decimal place and under of P/4, $$Q=(P/4) \times 1000$$

is calculated. For example, when P=2.924, Q=(P/4)×1000= (2.924/4)×1000=0.731×1000=731.

On the other hand, the inventor of the present invention measured the distances (S-A), (S-B) and (Go-Me) in cephalometric radiograms of many patients of obstructive sleep apnea syndrome, and calculated the equation (3). As a result, it was found that for the patients of obstructive sleep apnea syndrome $$P=((S-B)+(Go-Me))/(S-A=2.XYZ$$

(X, Y and Z are integers of 0 to 9).
In other words, P of the majority of the patients is in the range of 2.000≤P<3.000, especially in the range of 2.000≤P<2.500. However, for a few patients it may become P<2.000. In this case, as the index for deciding the risk of obstructive sleep apnea syndrome, P itself may be used, but presentation of integers is easy to understand. For this, in case of 2.000≤P<3.000, typically, after calculating P, further omitting the figures of the fourth decimal place and under, Q=(P-[P])×1000 is calculated. [P] denotes omitting decimal places of P, therefore, P-[P] denotes taking out the decimal places of P. Q=(P-[P])×1000 denotes multiplying the decimal places taken out in this way by 1000 times. In this case, it becomes P-[P]=2.XYZ-[2.XYZ]=2.XYZ-2=0.XYZ. Therefore, it becomes Q=(P-[P])×1000=XYZ, and becomes integers equal to or larger than 0 and equal to or less than 999. For example, when P=2.212, it becomes P=(P-[P])× 1000=(2.212-[2.212])×1000=(2.212-2)×1000=0.212× 1000=212. P-[P] or numerals XYZ multiplied P-[P] by 1000 times can be considered numerals which evaluate the ratio of the size of the mandible for the maxilla in the profile of a head.

When P is calculated by the equation (4), as P has the unit of length, it is possible to use the length P directly as the index for deciding the risk of obstructive sleep apnea syndrome.

When P is calculated by the equation (5) or (6), for example, the figures of the fourth decimal place and under of P are further omitted and $$Q=P \times 1000$$

is calculated.

The method of deciding the risk of obstructive sleep apnea syndrome can be easily carried out by a computer having at least one of the predetermined programs including the equations of P and Q. Kinds of the computer are not limited and may be any one of a desk top type, a lap top type, various mobile terminals such as a tablet terminal etc. The programs can be stored in various computer-readable recording media such as a CD-ROM etc., or, can be provided through electrical communication line such as internet. In the computer, as the necessary data for calculation, for example, the distances selected from a group consisting of the distances (S-A), (S-B), (Go-A), (Go-B), (Go-Me) and (Cd-Go) in a cephalometric radiogram are entered. Or taking in the image data to be obtained by cephalometric radiography in the computer, and from the image data, measuring the coordinates of S, A, B, Go, Cd and Me, from the measured coordinates, the distances (S-A), (S-B), (Go-A), (Go-B), (Go-Me) and (Cd-Go) are obtained by calculations, then using the distances P and Q are calculated by the equations. Typically, for example, lateral cephalometric radiography of the subject is carried out using the X-ray diagnostic system with the computer having the program and the method of deciding the risk of obstructive sleep apnea syndrome is carried out based on the result. The computer and the X-ray diagnostic system may be connected by cable communications or radio communications.

More specifically, according to the method of deciding the risk of obstructive sleep apnea syndrome, decision of the risk is carried out based on the methods of deciding the risk of obstructive sleep apnea syndrome according to the first to the fourth embodiments and further, by using the distance selected from a group consisting of the distance (S-A) between S and A, the distance (S-B) between S and B, the distance (Go-A) between Go and A, the distance (Go-B) between Go and B, the distance (Go-Me) between Go and Me and the distance (Cd-Go) between Cd and Go which are measured by cephalometric radiography of a subject, P is calculated by at least one of the equations (1) to (6), or Q is calculated by using P, and by comparing the calculated P or Q with the predetermined value, decision of the risk of obstructive sleep apnea syndrome of the subject is carried out.

The method of deciding the risk of obstructive sleep apnea syndrome according to the tenth embodiment based on lateral cephmalometric radiography of a subject is specifically described.

Figure 50:
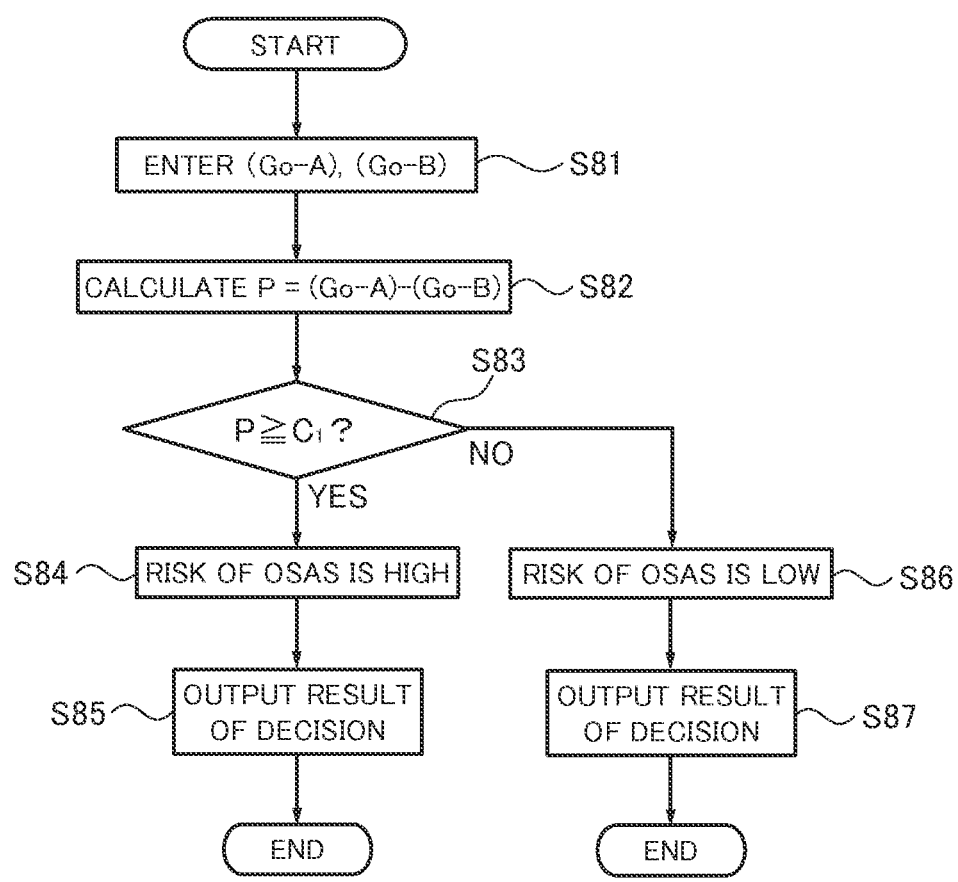
FIG. 50 A flow chart showing a method of deciding the risk of obstructive sleep apnea syndrome according to the tenth embodiment of the invention.

FIG. 50 shows a flow chart of the method of deciding the risk of obstructive sleep apnea syndrome. Programs are created according to the flow chart and are executed on a computer.

Before making the calculation, taking a cephalometric radiogram of a subject to be decided the risk of becoming OSAS, the distance (Go-A) between Go and A and the distance (Go-B) between Go and B are measured. The measurement of the distances can be easily carried out by using S, Go and Me which are detected by, for example, entering the coordinate data of measured points of A, B and Go on the cephalometric radiogram by using a pen tablet or a digitizer, or by displaying the image on the display connected with a computer, moving the cursor to S, Go and Me and clicking on the display by a mouse, or by touching S, Go and Me by fingers of the hand, a touch pen, etc. when the touch panel display is used. Or, by taking the image data to be obtained by cephalometric radiography in a computer and measuring the coordinates of A, B and Go from the image data, the distances (Go-A) and (Go-B) may be obtained by calculation from the measured coordinates.

As shown in FIG. 50, in step S81, the distances (Go-A) and (Go-B) which are measured as described above are entered.

In step S82, from the entered distances (Go-A) and (Go-B), P is calculated according to $$P=(Go-A)-(Go-B).$$

In step S83, from P which is obtained by the above calculation, it is decided whether $P \geq C_1$ or not.

When $P \geq C_1$, it is decided in step S84 that the risk of becoming OSAS is high. For example, when $P \geq 7$ mm, it is decided that the risk of becoming OSAS is high. In this case, further, when $P \geq 10$ mm, for example, it may be decided that the risk of becoming OSAS is especially high.

In step S85, the result of decision that the risk of becoming OSAS is high is output to, for example, the display.

When it is decided in step S83 that $P \geq C_1$ does not hold, in other words, $P < C_1$ holds, it is decided in step S86 that the risk of becoming OSAS is low.

In step S87, the result of decision that the risk of becoming OSAS is low is output to, for example, the display.

Example 4

Taken were cephalometric radiograms of twenty three patients who were diagnosed a serious illness, a medium illness or a slight illness by carrying out examination of OSAS by PSG. Radiography was carried out at centric occlusion or a position near to it (hereafter the same). Tracings were made based on the cephalometric radiograms, the distances (Go-A) and (Go-B) were measured and P=(Go-A)−(Go-B) was calculated.

Figure 51:
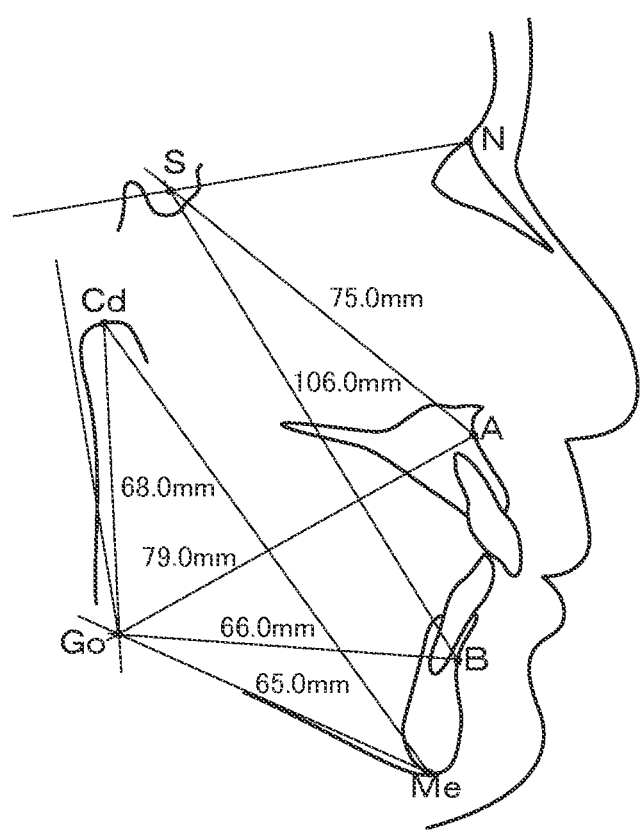
FIG. 51 A tracing made based on a cephalometric radiogram of a patient 31.
Figure 52:
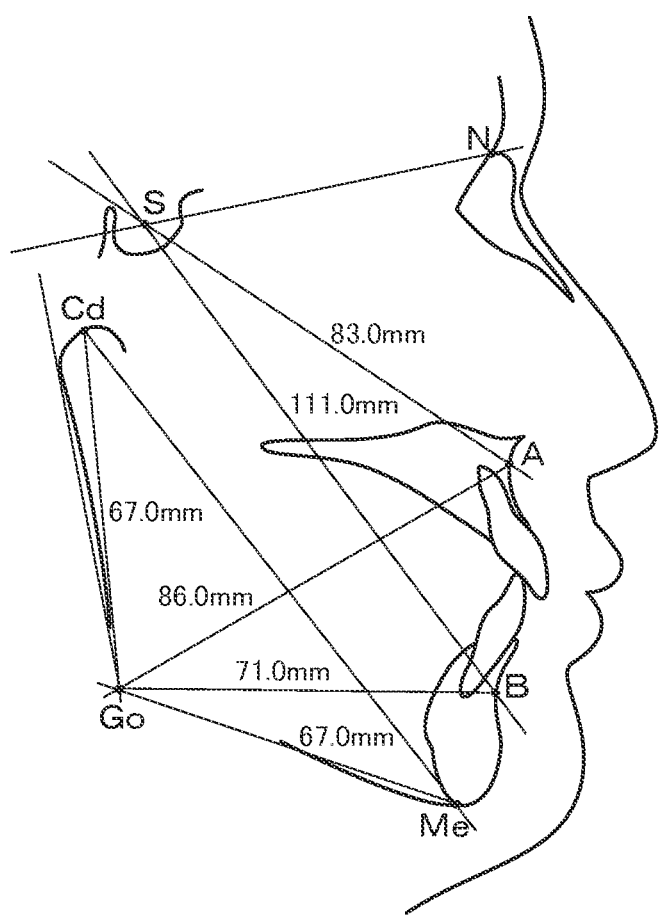
FIG. 52 A tracing made based on a cephalometric radiogram of a patient 32.
Figure 53:
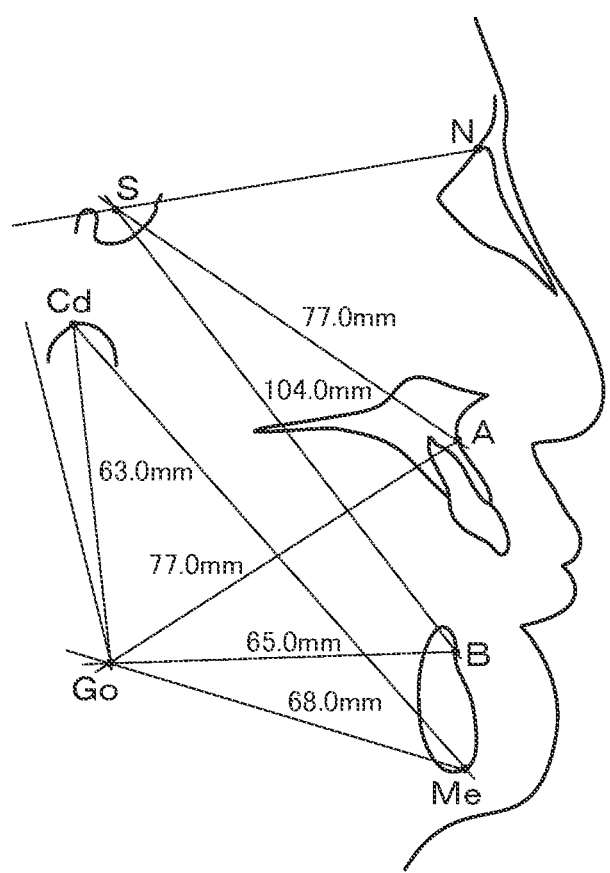
FIG. 53 A tracing made based on a cephalometric radiogram of a patient 33.
Figure 54:
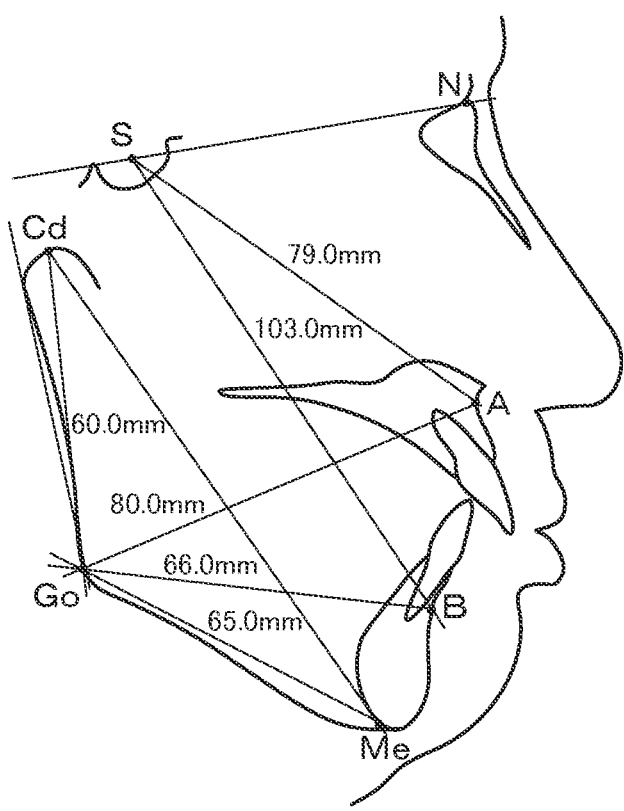
FIG. 54 A tracing made based on a cephalometric radiogram of a patient 34.
Figure 55:
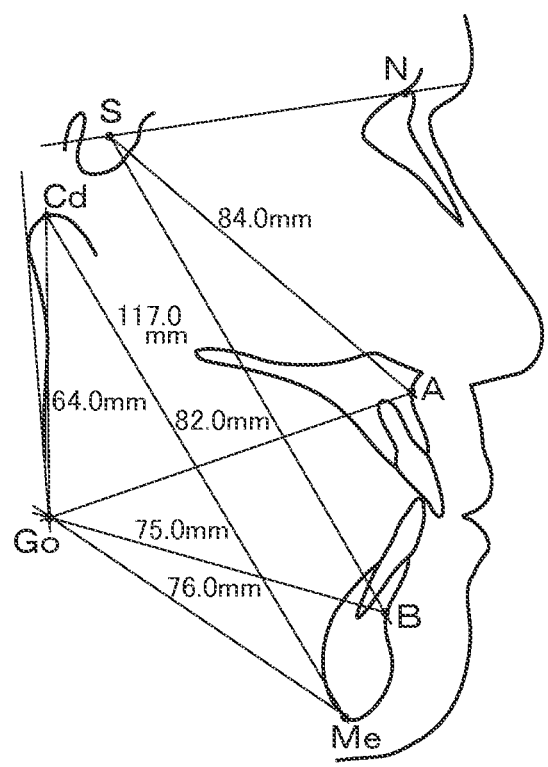
FIG. 55 A tracing made based on a cephalometric radiogram of a patient 35.
Figure 56:
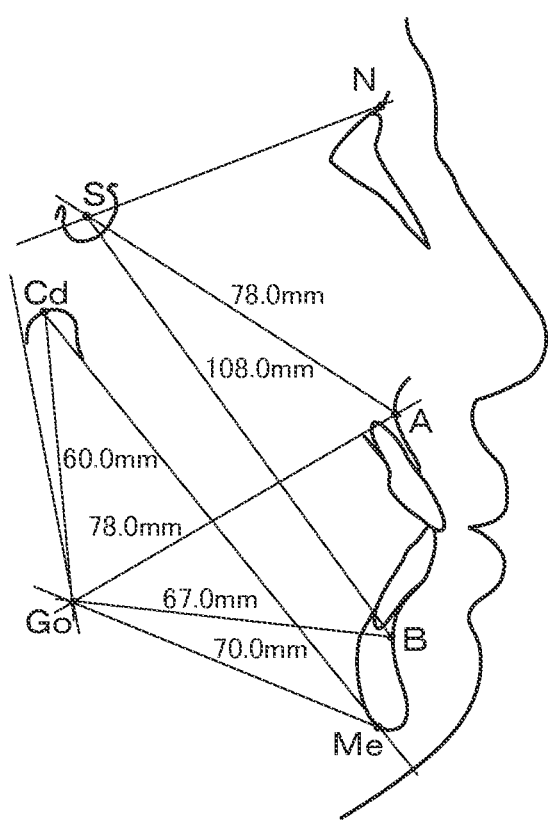
FIG. 56 A tracing made based on a cephalometric radiogram of a patient 36.
Figure 57:
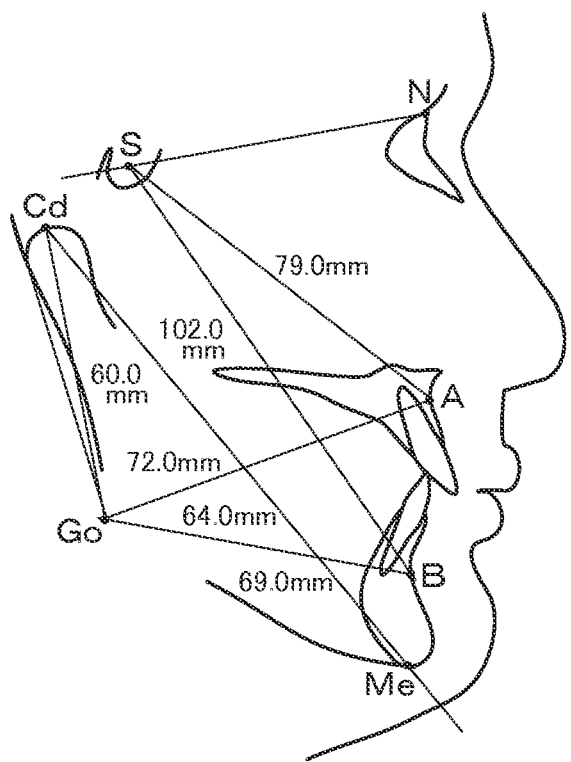
FIG. 57 A tracing made based on a cephalometric radiogram of a patient 37.
Figure 58:
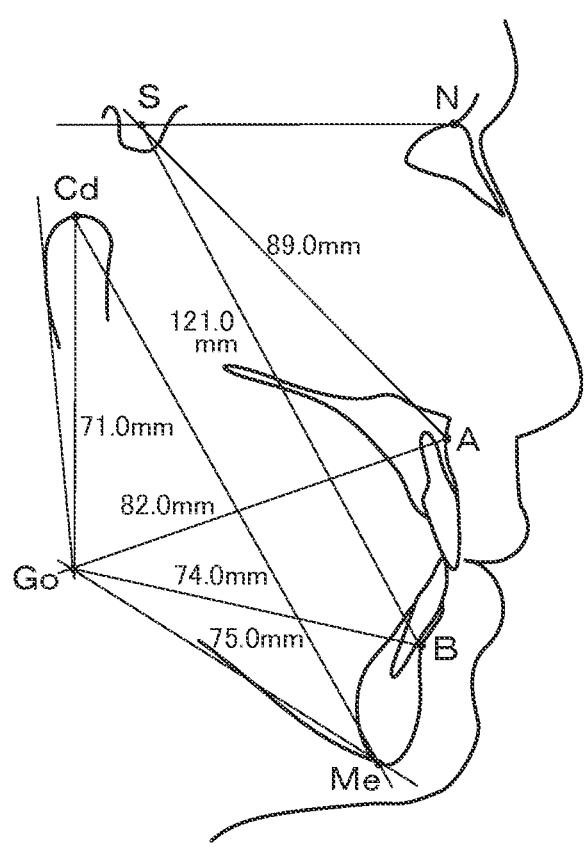
FIG. 58 A tracing made based on a cephalometric radiogram of a patient 38.
Figure 59:
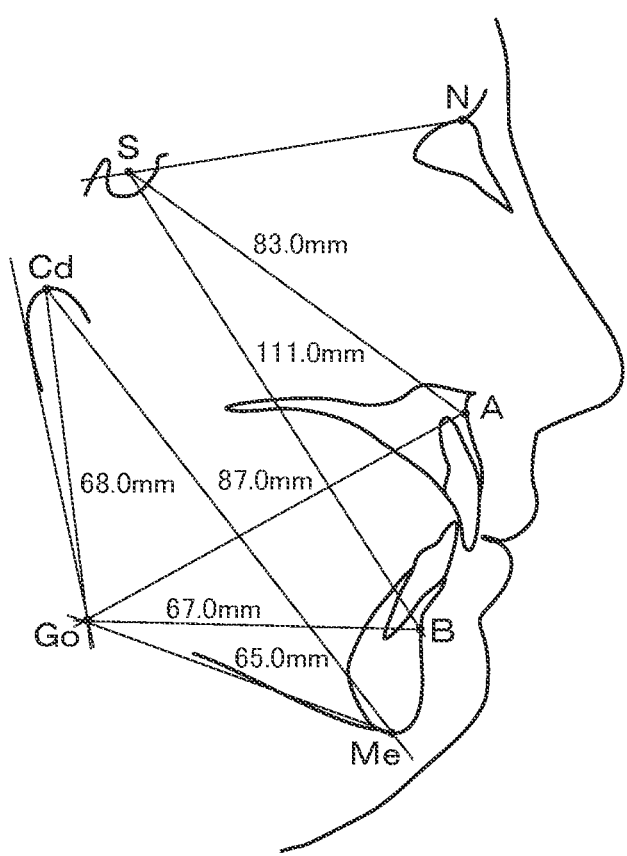
FIG. 59 A tracing made based on a cephalometric radiogram of a patient 39.
Figure 60:
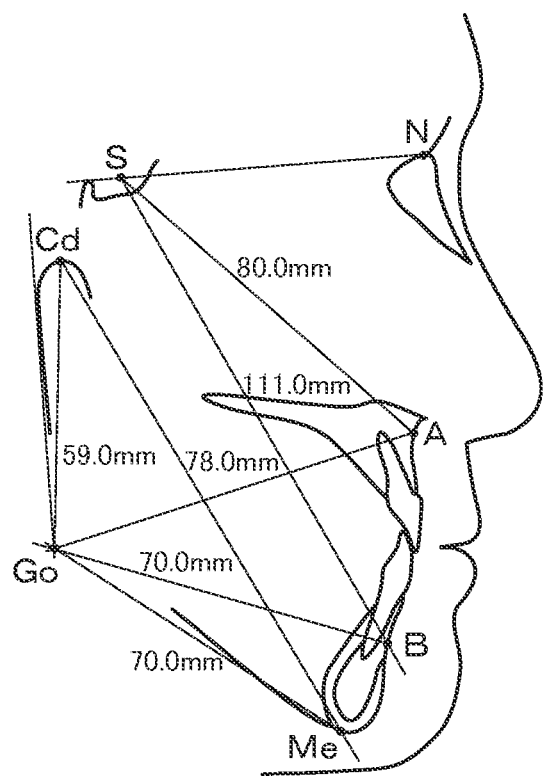
FIG. 60 A tracing made based on a cephalometric radiogram of a patient 40.
Figure 61:
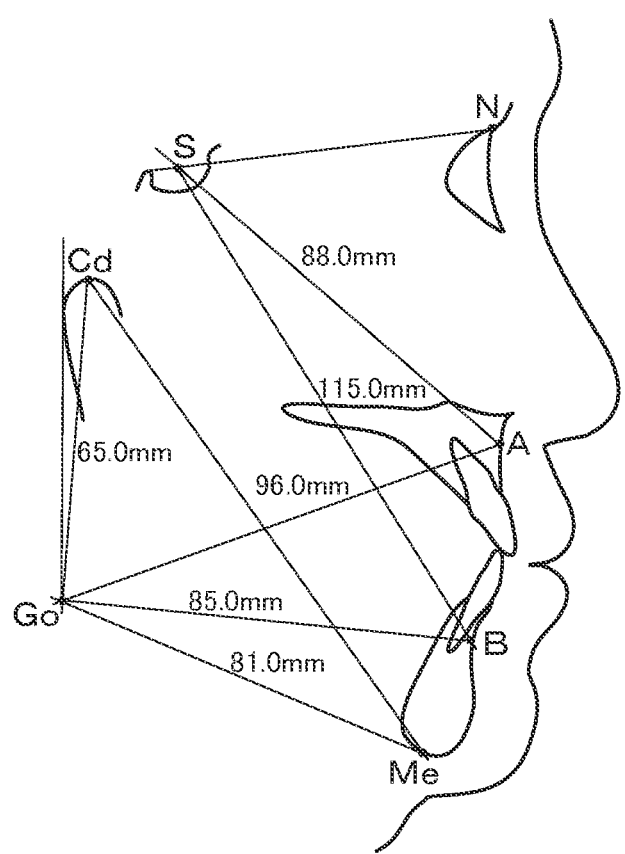
FIG. 61 A tracing made based on a cephalometric radiogram of a patient 41.
Figure 62:
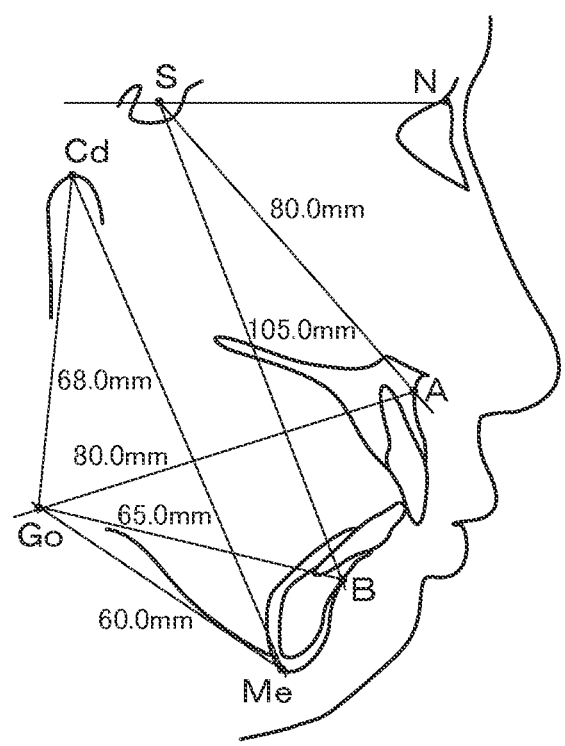
FIG. 62 A tracing made based on a cephalometric radiogram of a patient 42.
Figure 63:
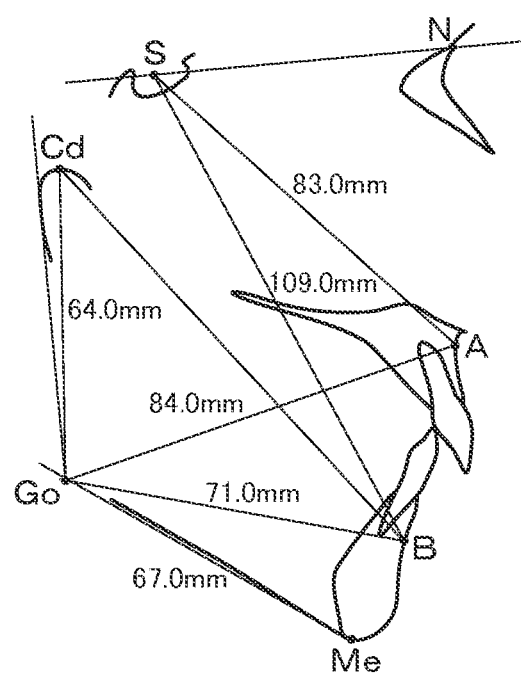
FIG. 63 A tracing made based on a cephalometric radiogram of a patient 43.
Figure 64:
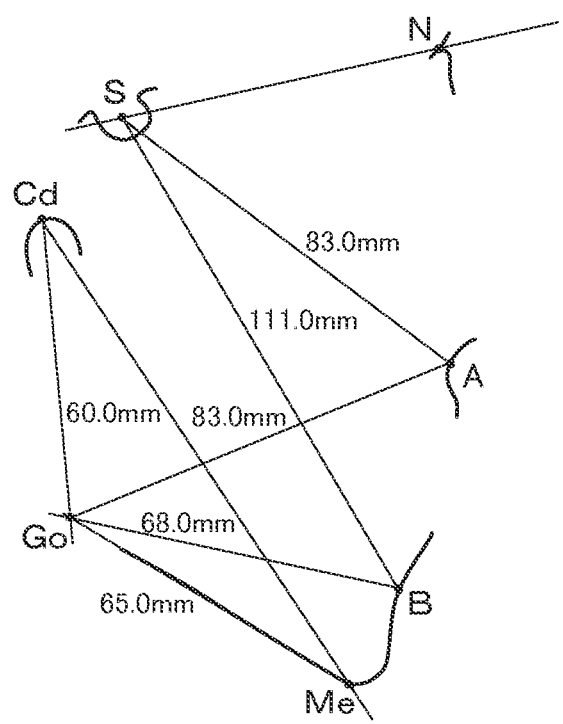
FIG. 64 A tracing made based on a cephalometric radiogram of a patient 44.
Figure 65:
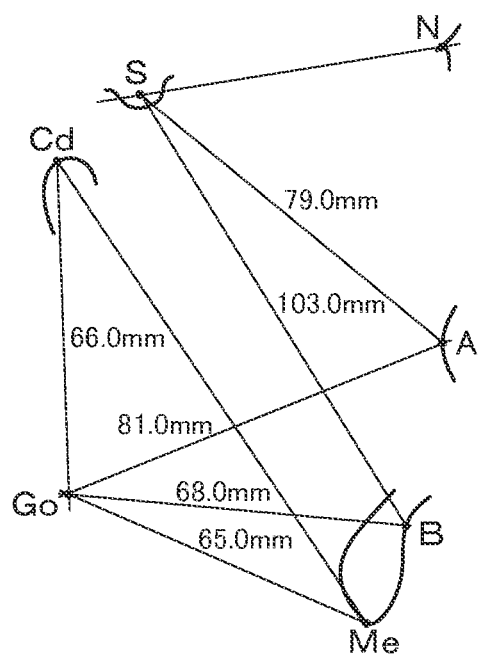
FIG. 65 A tracing made based on a cephalometric radiogram of a patient 45.
Figure 66:
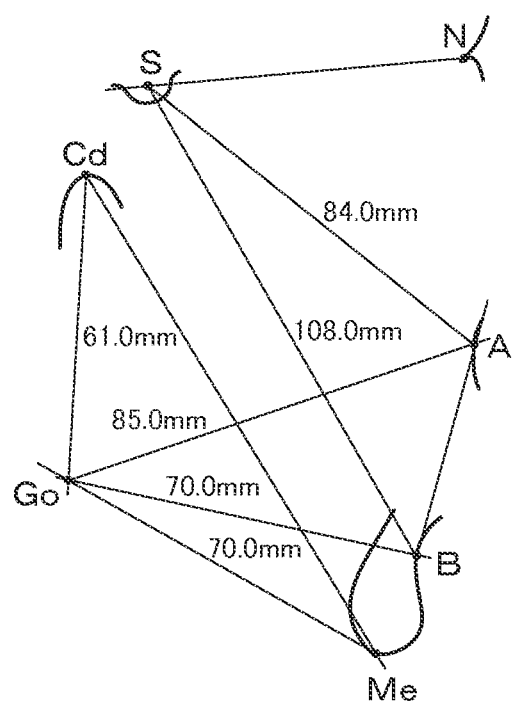
FIG. 66 A tracing made based on a cephalometric radiogram of a patient 46.
Figure 67:
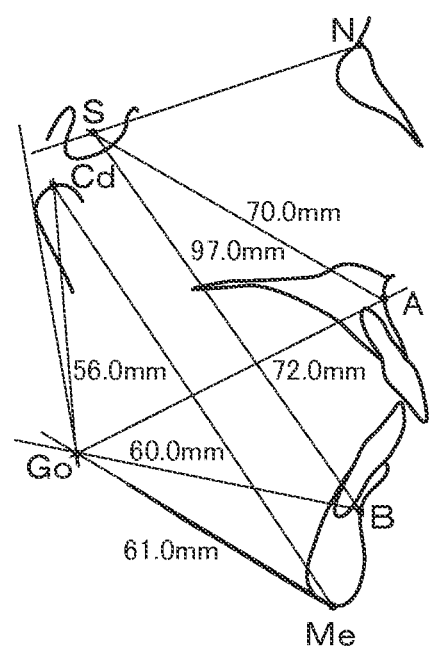
FIG. 67 A tracing made based on a cephalometric radiogram of a patient 47.
Figure 68:
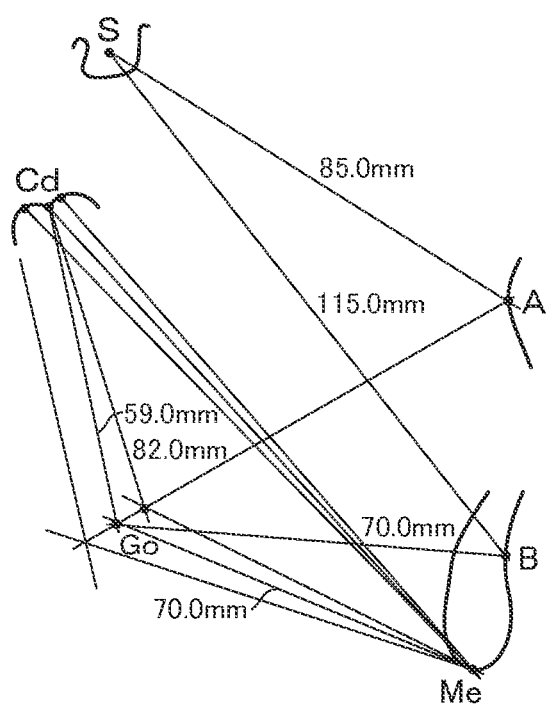
FIG. 68 A tracing made based on a cephalometric radiogram of a patient 48.
Figure 69:
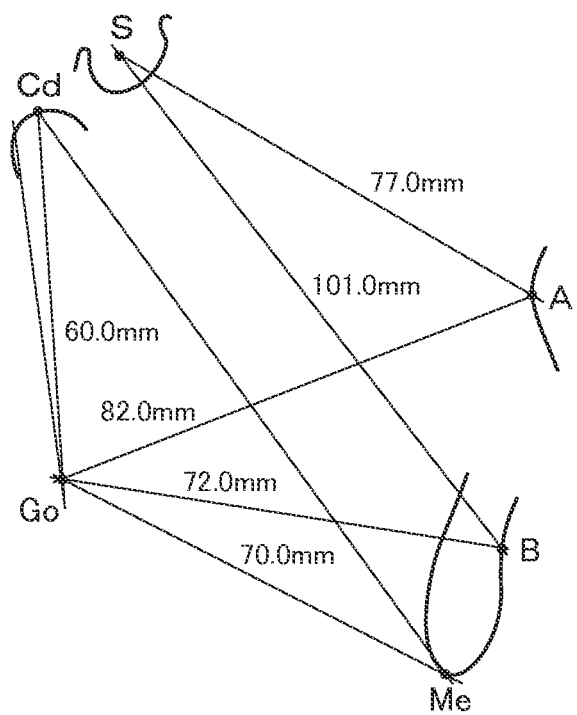
FIG. 69 A tracing made based on a cephalometric radiogram of a patient 49.
Figure 70:
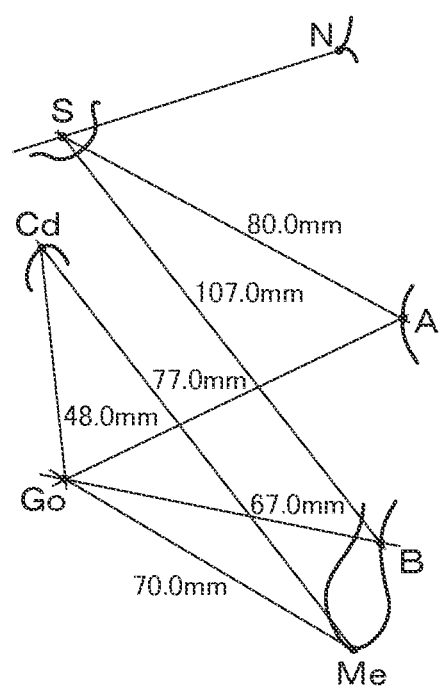
FIG. 70 A tracing made based on a cephalometric radiogram of a patient 50.
Figure 71:
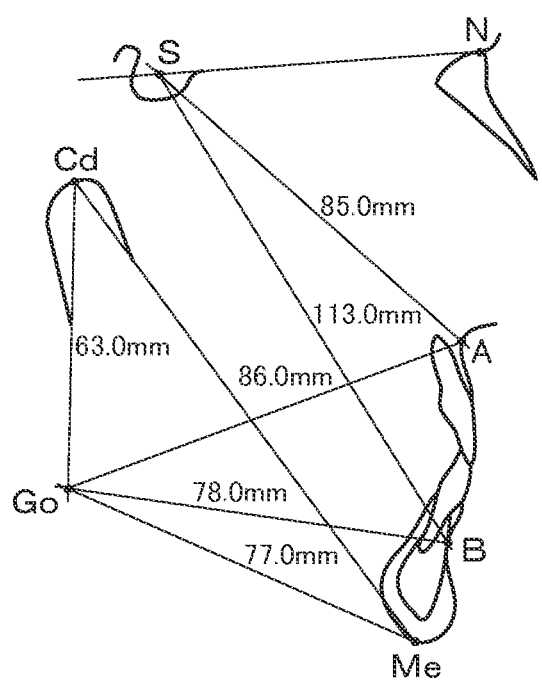
FIG. 71 A tracing made based on a cephalometric radiogram of a patient 51.
Figure 72:
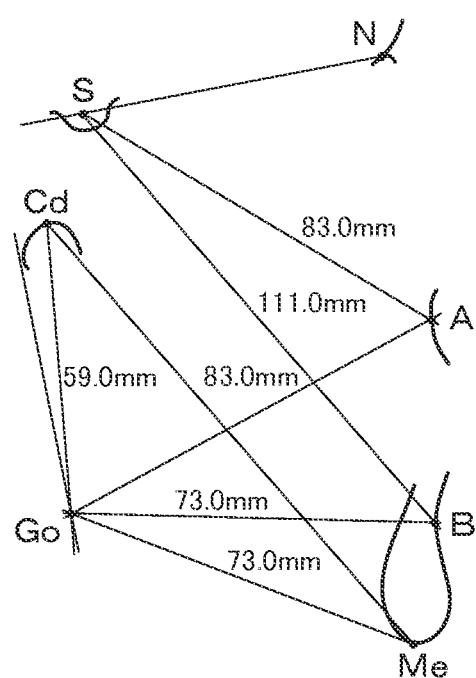
FIG. 72 A tracing made based on a cephalometric radiogram of a patient 52.
Figure 73:
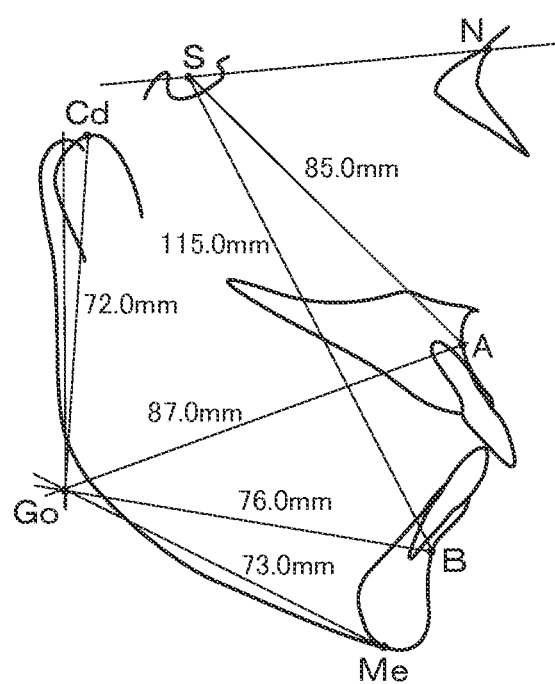
FIG. 73 A tracing made based on a cephalometric radiogram of a patient 53.
Figure 74:
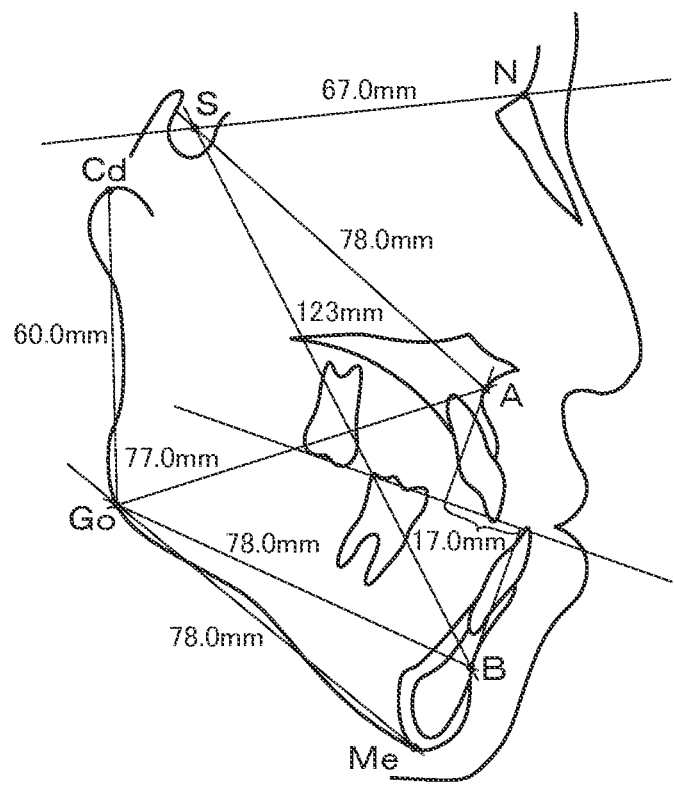
FIG. 74 A tracing made based on a cephalometric radiogram of a subject 54.
Figure 75:
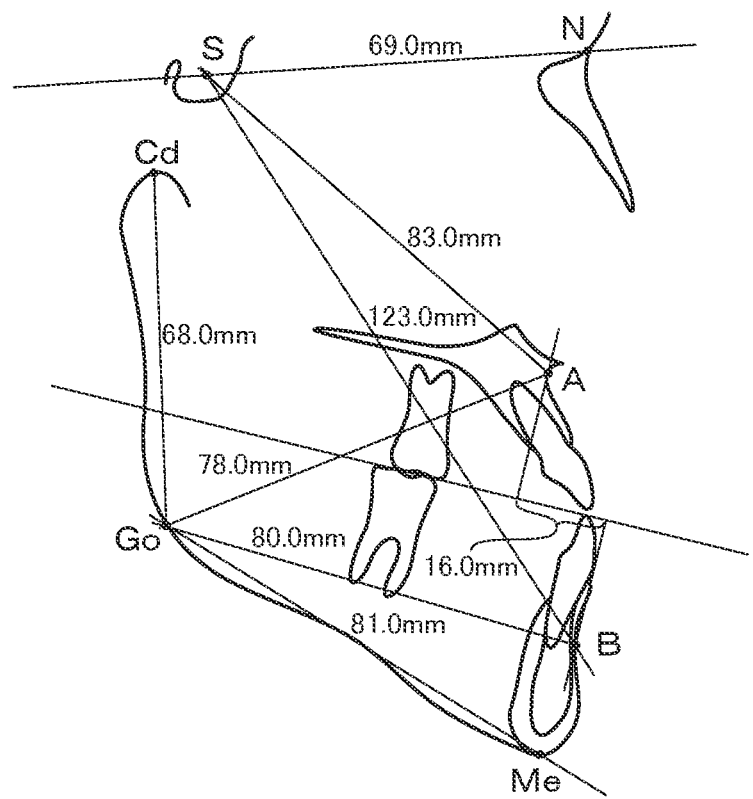
FIG. 75 A tracing made based on a cephalometric radiogram of a subject 55.
Figure 76:
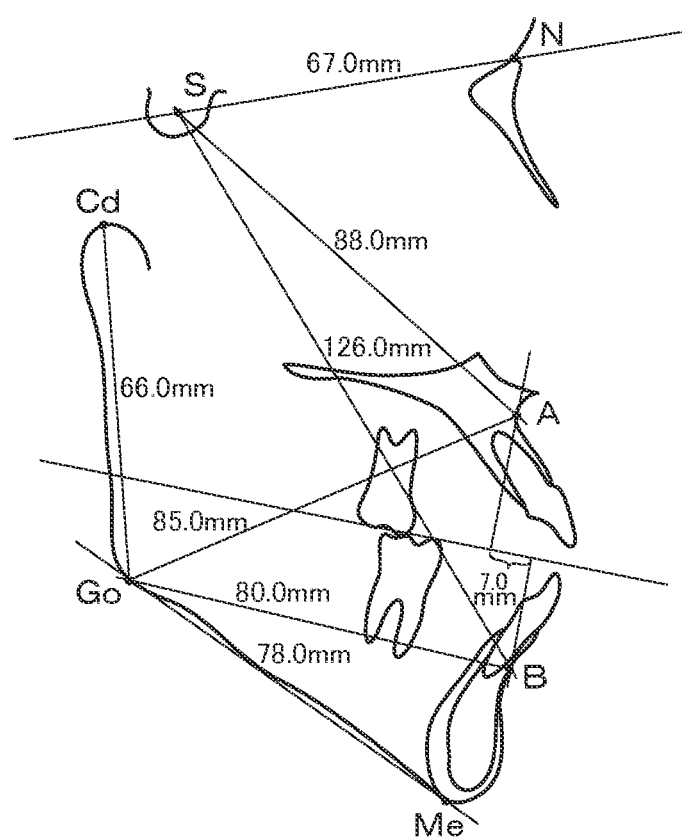
FIG. 76 A tracing made based on a cephalometric radiogram of a subject 56.
Figure 77:
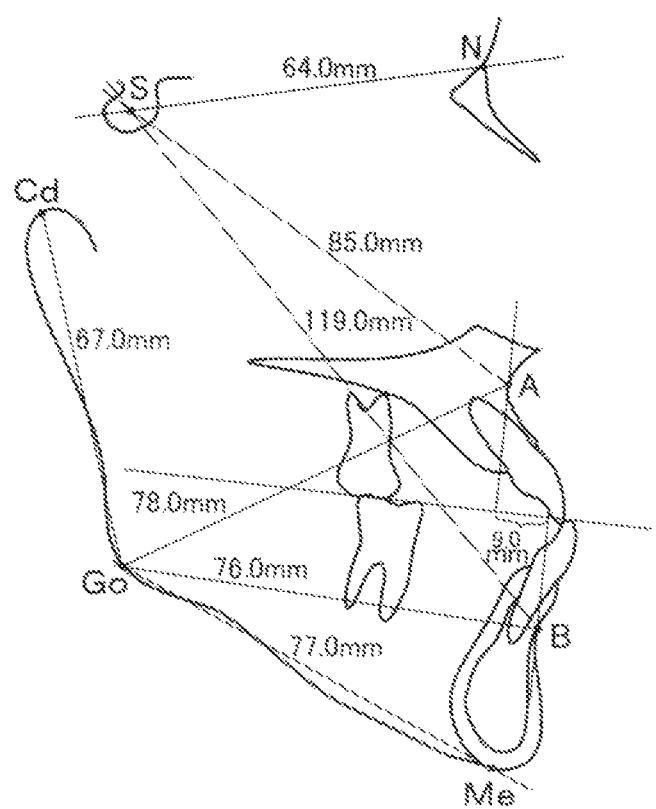
FIG. 77 A tracing made based on a cephalometric radiogram of a subject 57.
Figure 78:
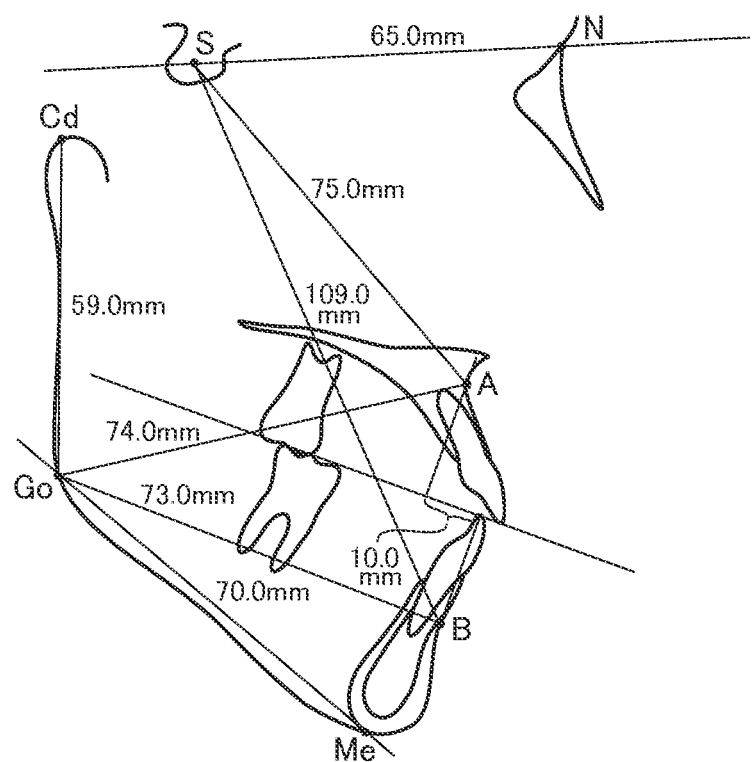
FIG. 78 A tracing made based on a cephalometric radiogram of a subject 58.
Figure 79:
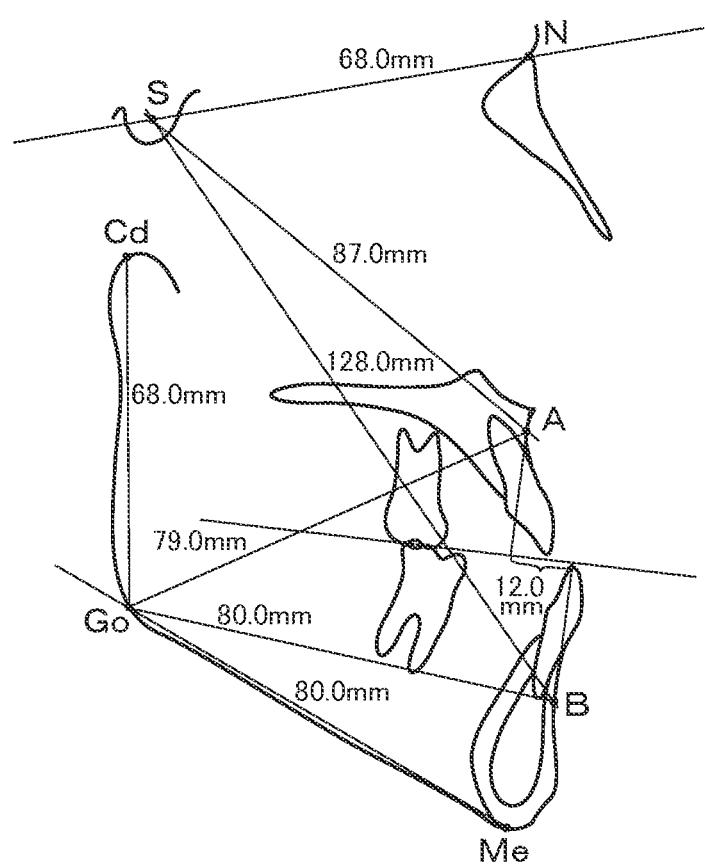
FIG. 79 A tracing made based on a cephalometric radiogram of a subject 59.
Figure 80:
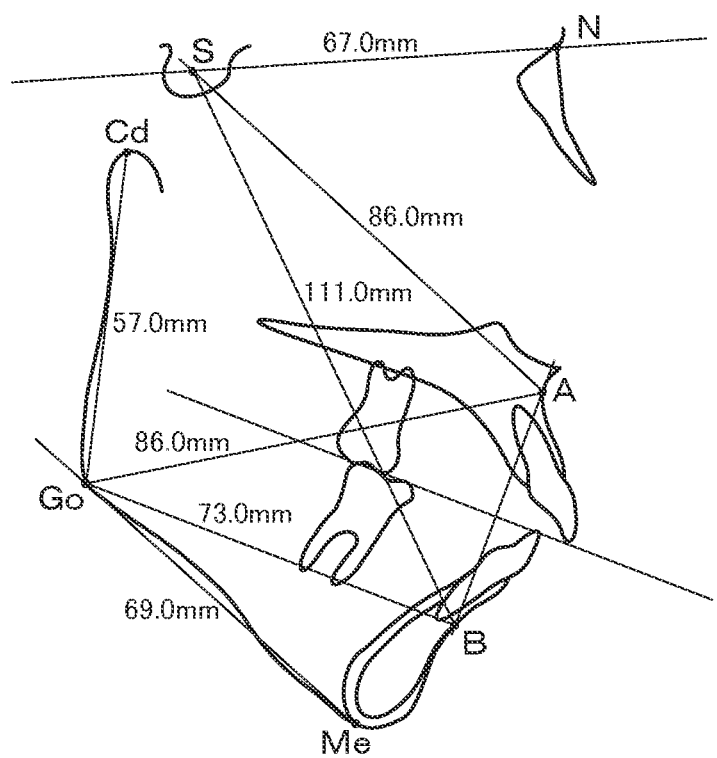
FIG. 80 A tracing made based on a cephalometric radiogram of a subject 60.
Figure 81:
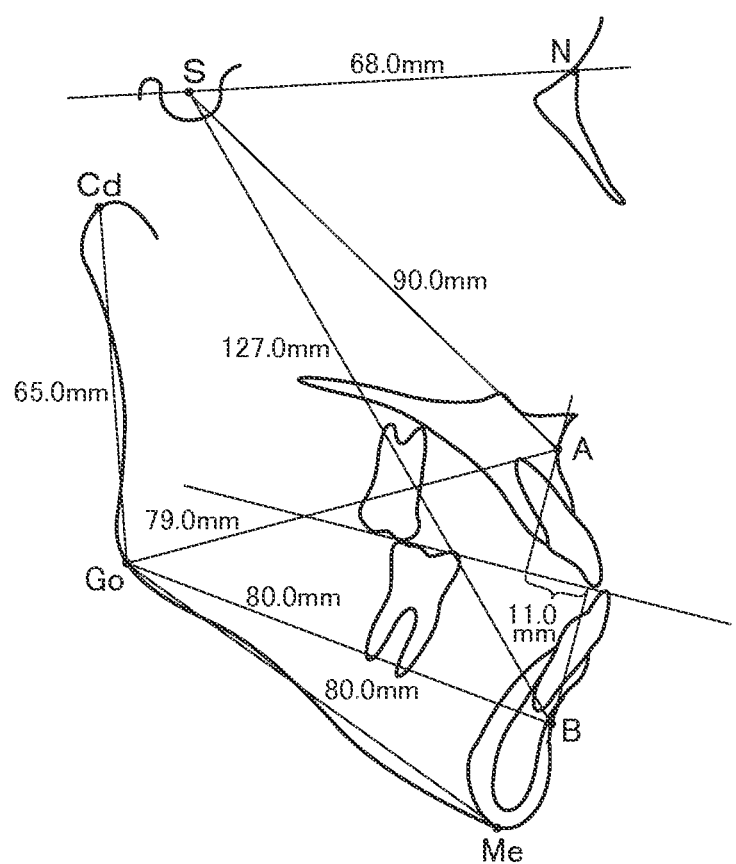
FIG. 81 A tracing made based on a cephalometric radiogram of a subject 61.
Figure 82:
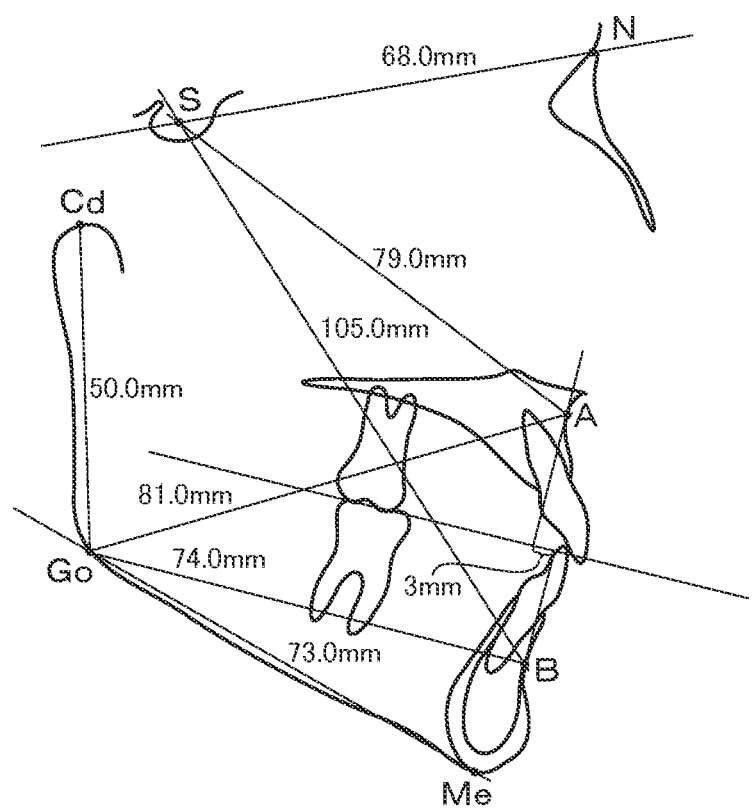
FIG. 82 A tracing made based on a cephalometric radiogram of a subject 62.
Figure 83:
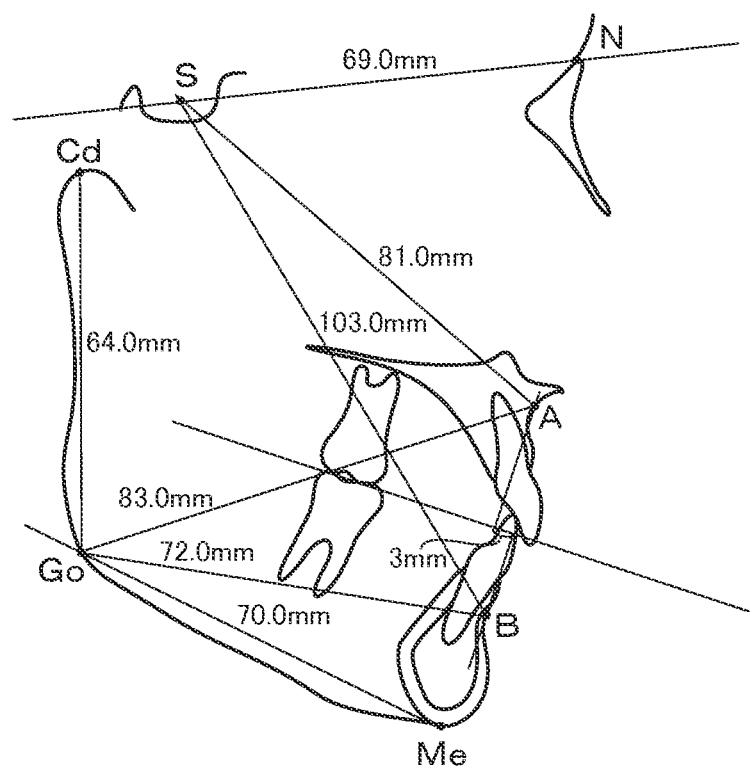
FIG. 83 A tracing made based on a cephalometric radiogram of a subject 63.
Figure 84:
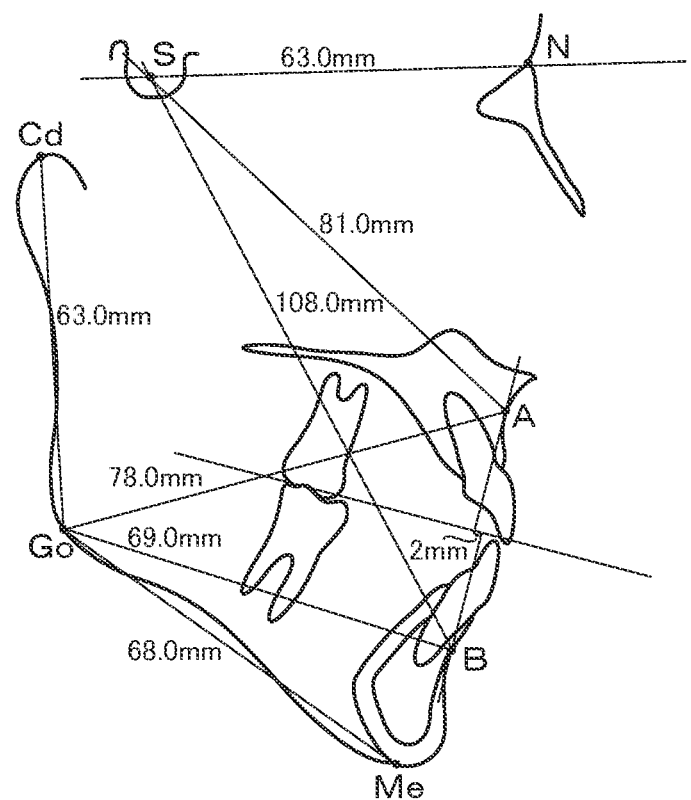
FIG. 84 A tracing made based on a cephalometric radiogram of a subject 64.
Figure 85:
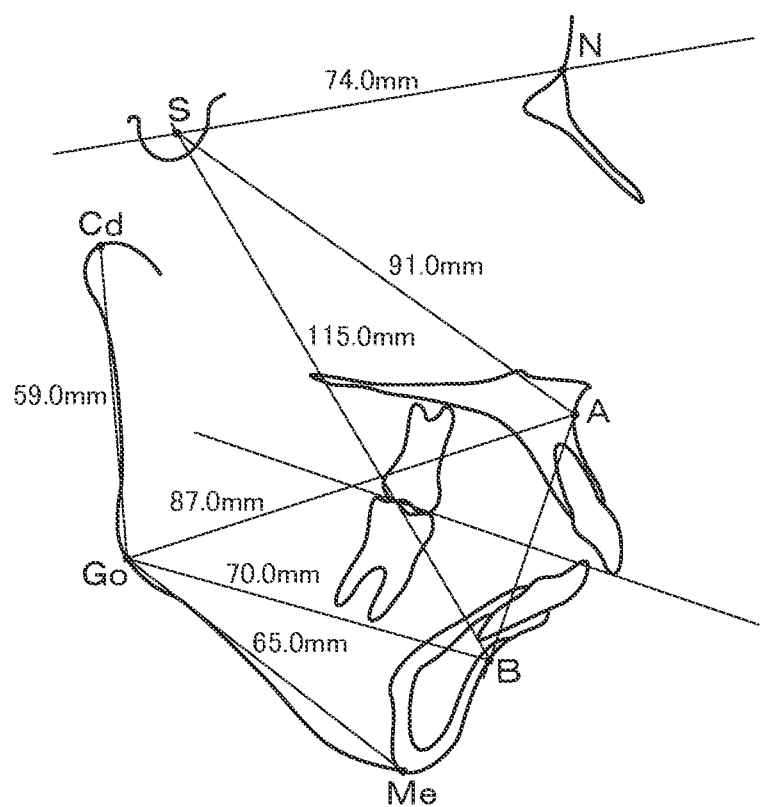
FIG. 85 A tracing made based on a cephalometric radiogram of a subject 65.

Tracings of the patients 31 to 53 are shown in FIG. 51 top FIG. 73. Distances measured from FIG. 51 to FIG. 73, (Go-A), (Go-B), P=(Go-A)−(Go-B) and AHI (supine position) and $SaO_2$ (the lowest value) obtained by PSG are as follows. With respect to the patient 33, $SpO_2$ (the lowest value) is shown instead of $SaO_2$ (the lowest value). It is to be noted that the patients 41, 36, 37, 48, 34, 42, 49, 51, 39, 45, 43, 44, 33, 52, 32, 53 are the same as the patients 1 to 16, respectively.

| Patient | (Go-A) (mm) | (Go-B) (mm) | P (mm) | AHI | $SaO_2$ (%) |
|---|---|---|---|---|---|
| 31 | 79 | 66 | 13 | 70.4 | 87 |
| 32 | 86 | 71 | 15 | 71.2 | 71 |
| 33 | 77 | 65 | 12 | 41.1 | 68($SpO_2$) |
| 34 | 80 | 66 | 14 | 53.5 | 71 |
| 35 | 82 | 75 | 7 | 58.4 | 78 |
| 36 | 78 | 67 | 11 | 36.8 | 87 |
| 37 | 72 | 64 | 8 | 30.2 | 83 |
| 38 | 82 | 74 | 8 | 36.4 | 90 |
| 39 | 87 | 67 | 20 | 35.5 | 80 |
| 40 | 78 | 70 | 8 | 23.2 | 73 |
| 41 | 96 | 85 | 11 | 43.1 | 70 |
| 42 | 80 | 65 | 15 | 25.7 | 79 |
| 43 | 84 | 71 | 13 | 24.8 | 92 |

-continued

| Patient | (Go-A) (mm) | (Go-B) (mm) | P (mm) | AHI | $SaO_2$ (%) |
|---|---|---|---|---|---|
| 44 | 83 | 68 | 15 | 9.6 | 90 |
| 45 | 81 | 68 | 13 | 66.0 | 76 |
| 46 | 85 | 70 | 15 | 6.2 | 90 |
| 47 | 72 | 60 | 12 | 37.9 | 78 |
| 48 | 82 | 70 | 12 | 62.9 | 73 |
| 49 | 82 | 72 | 10 | 112.5 | 85 |
| 50 | 77 | 67 | 10 | 29.1 | 87 |
| 51 | 86 | 78 | 8 | 11.9 | 93 |
| 52 | 83 | 73 | 10 | 59.7 | 80 |
| 53 | 87 | 76 | 11 | 43.9 | 85 |

As a control group, twelve subjects 54 to 65 without respiratory disorder were adopted. Cephalometric radiograms of the subjects 54 to 65 were taken. From the tracings made based on the cephalometric radiograms the distances (Go-A) and (Go-B) were measured and P=(Go-A)−(Go-B) was calculated.

The tracings of the subjects 54 to 65 are shown in FIG. 74 to FIG. 85. The distance (Go-A) and the distance (Go-B) which were measured from FIG. 74 to FIG. 85 and P=(Go-A)−(Go-B) are as follows.

| Subject | (Go-A) (mm) | (Go-B) (mm) | P (mm) |
|---|---|---|---|
| 54 | 77 | 78 | −1 |
| 55 | 78 | 80 | −2 |
| 56 | 85 | 80 | 5 |
| 57 | 78 | 76 | 2 |
| 58 | 74 | 73 | 1 |
| 59 | 79 | 80 | −1 |
| 60 | 86 | 73 | 13 |
| 61 | 79 | 80 | −1 |
| 62 | 81 | 74 | 7 |
| 63 | 83 | 72 | 11 |
| 64 | 78 | 69 | 9 |
| 65 | 87 | 70 | 17 |

Figure 86:
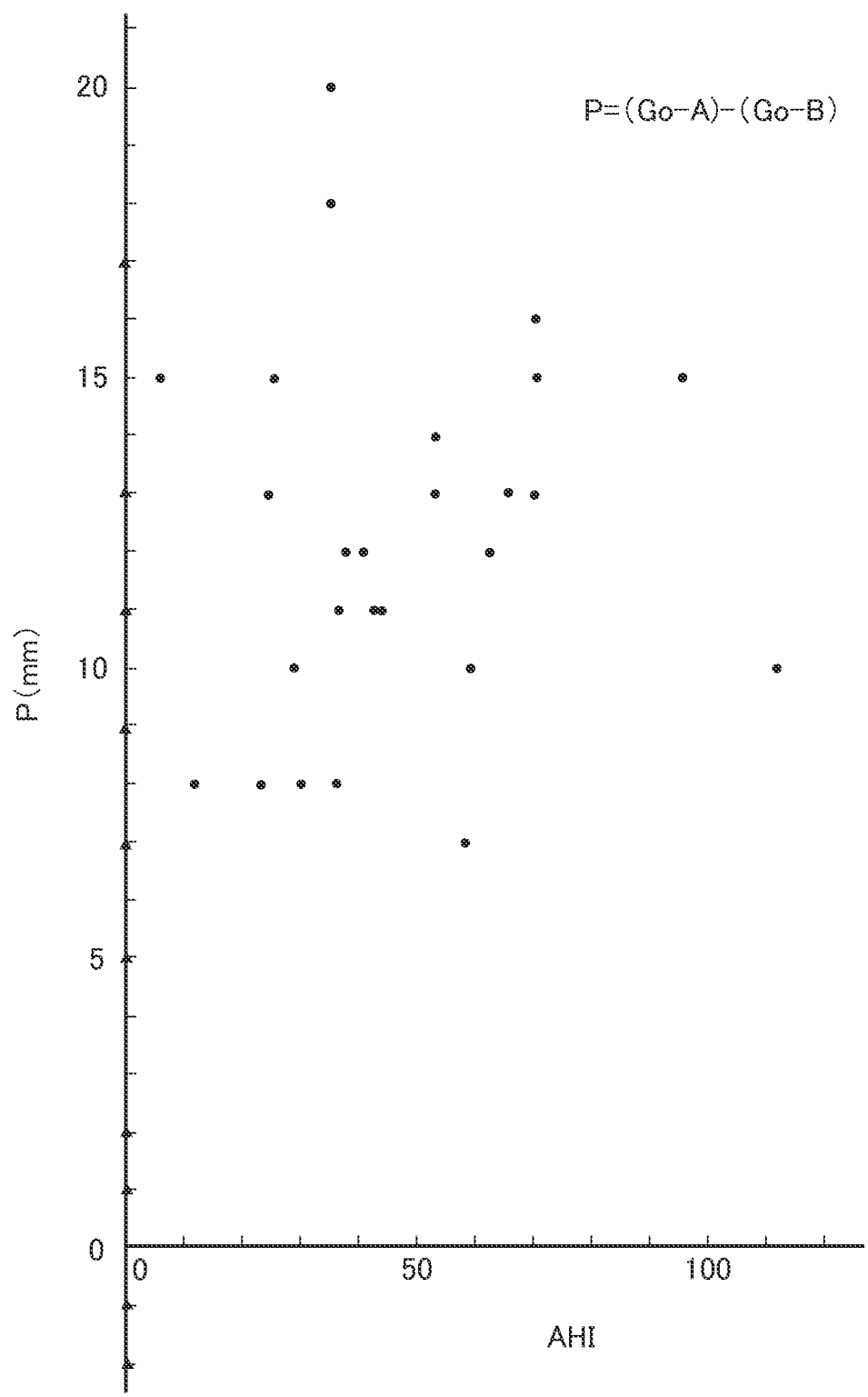
FIG. 86 A schematic drawing showing the result of calculation of the OSAS index P of the patients 31 to 53 and the subjects 54 to 65 in the tenth embodiment of the invention.

FIG. 86 shows the result of plotting the values of AHI and P of the patients 31 to 53. In FIG. 86, the values of P of the subjects 54 to 65 are plotted on the line of AHI=0. It is understood from FIG. 86 that P of the subjects 54 to 65 distribute in the wide range from −2 mm to 17 mm, whereas P of the patients 31 to 53 distribute in the range from 7 mm to 20 mm in a concentrated way, and both distributions are quite different. Therefore, by using the difference of distributions, it is possible to decide the risk of OSAS by the value of P.

According to the method of deciding the risk of obstructive sleep apnea syndrome according to the tenth embodiment, based on the distances (Go-A) and (Go-B) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

11. The Eleventh Embodiment

In the eleventh embodiment, the method of deciding the risk of obstructive sleep apnea syndrome is described.

Figure 87:
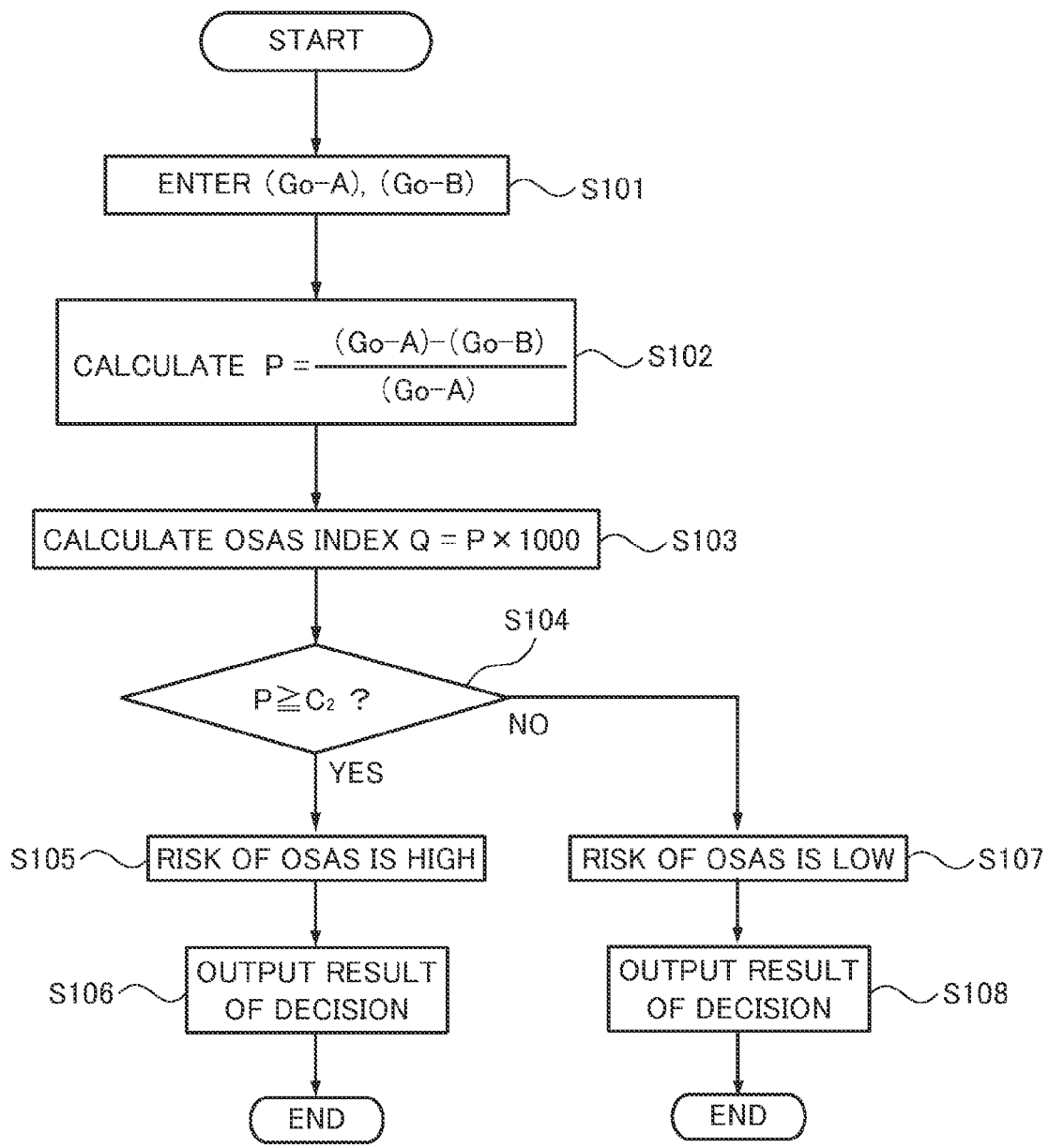
FIG. 87 A flow chart showing a method of deciding the risk of obstructive sleep apnea syndrome according to the eleventh embodiment of the invention.

FIG. 87 shows a flow chart of the method of deciding the risk of obstructive sleep apnea syndrome. Programs are created according to the flow chart and are executed on a computer.

As the same as the tenth embodiment, before carrying out the method of deciding the risk of obstructive sleep apnea syndrome, the distances (Go-A) and (Go-B) are measured.

As shown in FIG. 87, in step S101, the distances (Go-A) and (Go-B) measured as described above are entered.

In step S102, from the entered distances (Go-A) and (Go-B), P is calculated according to $P=((Go\text{-}A)-(Go\text{-}B))/(Go\text{-}A)$.

In step S103, after the figures of the fourth decimal place and under of P calculated as described above are omitted and $Q=P\times 1000$ is calculated.

In step S104, from Q obtained by the above calculation, it is decided whether $Q \geq C_2$ or not.

When $Q \geq C_2$, it is decided in step S105 that the risk of becoming OSAS is high. For example, when $Q \geq 85$, it is decided that the risk of becoming OSAS is high. In this case, further, when $Q \geq 110$, for example, it may be decided that the risk of becoming OSAS is especially high.

In step S106, the result of decision that the risk of becoming OSAS is high is output to, for example, the display.

When it is decided in step S104 that $Q \geq C_2$ does not hold, in other words, $Q < C_2$ holds, it is decided in step S107 that the risk of becoming OSAS is low.

In step S108, the result of decision that the risk of becoming OSAS is low is output to, for example, the display.

Example 5

From FIG. 51 to FIG. 73 which show the tracings made based on the cephalometric radiograms of the patients 31 to 53 the distances (Go-A) and (Go-B) were measured, P=((Go-A)−(Go-B))/(Go-A) was calculated and Q=P×1000 was calculated.

The distance (Go-A) and the distance (Go-B) which were measured from FIG. 51 to FIG. 73 and Q are as follows. AHI and Sao$_2$ or SpO$_2$ of the patients 31 to 53 obtained by PSG were the same as the Example 4.

| Patient | (Go-A) (mm) | (Go-B) (mm) | Q |
|---|---|---|---|
| 31 | 79 | 66 | 164 |
| 32 | 86 | 71 | 174 |
| 33 | 77 | 65 | 155 |
| 34 | 80 | 66 | 175 |
| 35 | 82 | 75 | 85 |
| 36 | 78 | 67 | 141 |
| 37 | 72 | 64 | 111 |
| 38 | 82 | 74 | 98 |
| 39 | 87 | 67 | 229 |
| 40 | 78 | 70 | 102 |
| 41 | 96 | 85 | 114 |
| 42 | 80 | 65 | 187 |
| 43 | 84 | 71 | 154 |
| 44 | 83 | 68 | 180 |
| 45 | 81 | 68 | 160 |
| 46 | 85 | 70 | 176 |
| 47 | 72 | 60 | 166 |
| 48 | 82 | 70 | 146 |
| 49 | 82 | 72 | 121 |
| 50 | 77 | 67 | 129 |

-continued

| Patient | (Go-A) (mm) | (Go-B) (mm) | Q |
|---|---|---|---|
| 51 | 86 | 78 | 93 |
| 52 | 83 | 73 | 120 |
| 53 | 87 | 76 | 126 |

As a control group, the subjects 54 to 65 were adopted. From FIG. 74 to FIG. 85 which show the tracings made based on the cephalometric radiograms of the subjects 54 to 65 the distances (Go-A) and (Go-B) were measured, P=((Go-A)−(Go-B))/(Go-A) was calculated and Q=P×1000 was calculated.

The distance (Go-A) and the distance (Go-B) which were measured from FIG. 74 to FIG. 85 and Q are as follows.

| Subject | (Go-A) (mm) | (Go-B) (mm) | Q |
|---|---|---|---|
| 54 | 77 | 78 | −12 |
| 55 | 78 | 80 | −25 |
| 56 | 85 | 80 | 58 |
| 57 | 78 | 76 | 25 |
| 58 | 74 | 73 | 13 |
| 59 | 79 | 80 | −12 |
| 60 | 86 | 73 | 151 |
| 61 | 79 | 80 | −12 |
| 62 | 81 | 74 | 86 |
| 63 | 83 | 72 | 132 |
| 64 | 78 | 69 | 115 |
| 65 | 87 | 70 | 195 |

Figure 88:
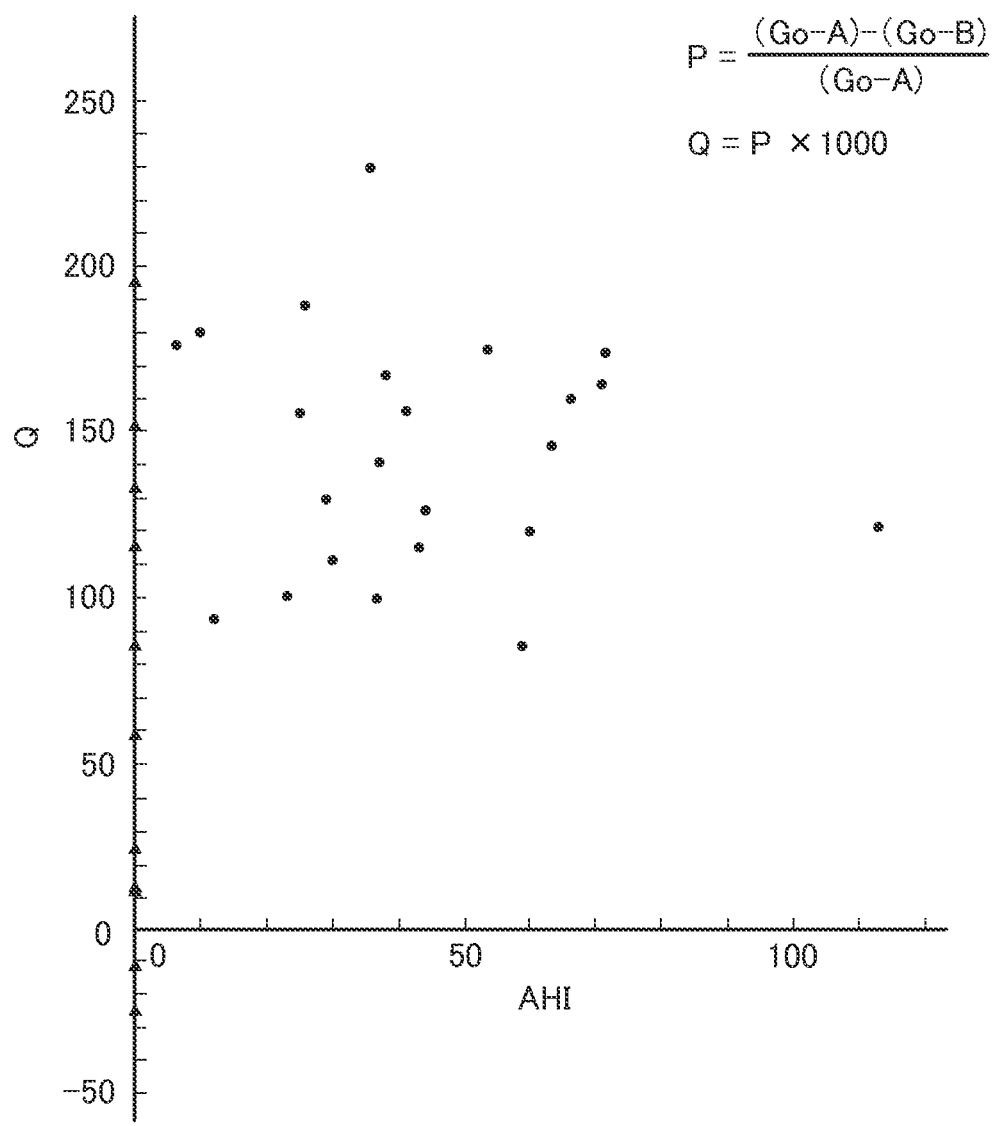
FIG. 88 A schematic drawing showing the result of calculation of the OSAS index Q of the patients 31 to 53 and the subjects 54 to 65 in the eleventh embodiment of the invention.

FIG. 88 shows the result of plotting the values of AHI and Q of the patients 31 to 53. In FIG. 88, the values of Q of the subjects 54 to 65 are plotted on the line of AHI=0. It is understood from FIG. 88 that Q of the subjects 54 to 65 distribute in the wide range from −25 to 195, whereas Q of the patients 31 to 53 distribute in the range from 85 to 229 in a concentrated manner, and both distributions are quite different. Therefore, by using the difference of distributions, it is possible to decide the risk of OSAS by the value of Q.

According to the method of deciding the risk of obstructive sleep apnea syndrome according to the eleventh embodiment, based on the distances (Go-A) and (Go-B) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

12. The Twelfth Embodiment

In the twelfth embodiment, the method of deciding the risk of obstructive sleep apnea syndrome is described.

Figure 89:
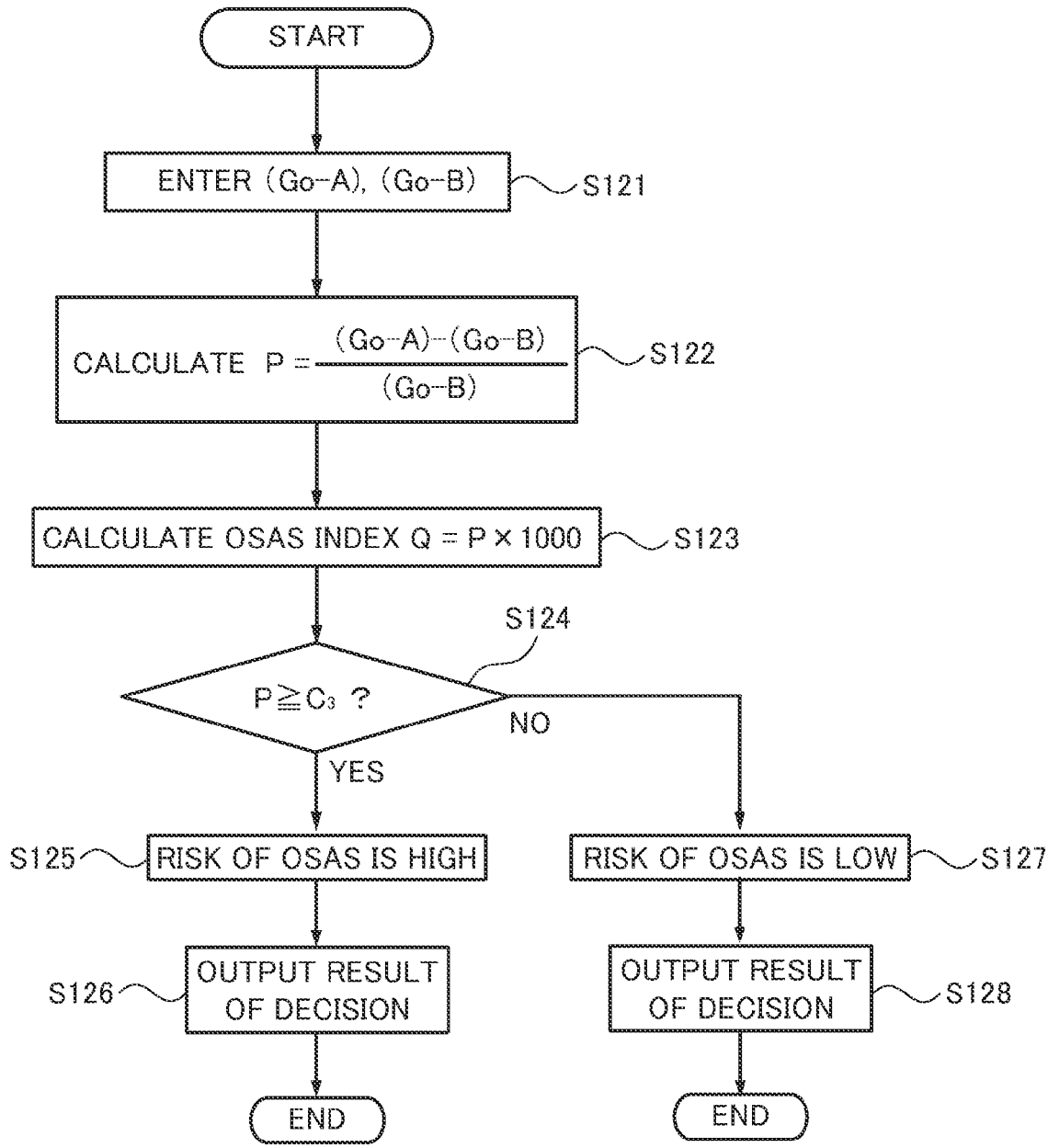
FIG. 89 A flow chart showing a method of deciding the risk of obstructive sleep apnea syndrome according to the twelfth embodiment of the invention.

FIG. 89 shows a flow chart of the method of deciding the risk of obstructive sleep apnea syndrome. Programs are aerated according to the flow chart and are executed on a computer.

As the same as the tenth embodiment, before carrying out the method of deciding the risk of obstructive sleep apnea syndrome, the distances (Go-A) and (Go-B) are measured.

As shown in FIG. 89, in step S121, the distances (Go-A) and (Go-B) measured as described above are entered.

In step S122, from the entered distances (Go-A) and (Go-B), P is calculated according to $$P=((Go\text{-}A)-(Go\text{-}B))/(Go\text{-}B).$$

In step S123, after the figures of the fourth decimal place and under of P calculated as described above are omitted and $$Q=P\times 1000$$

is calculated.

In step S124, from P obtained by the above calculation, it is decided whether $Q \geq C_3$ or not.

When $Q \geq C_3$, it is decided in step S125 that the risk of becoming OSAS is high. For example, when $Q \geq 93$, it is decided that the risk of becoming OSAS is high. In this case, further, when $Q \geq 110$, for example, it may be decided that the risk of becoming OSAS is especially high.

In step S126, the result of decision that the risk of becoming OSAS is high is output to, for example, the display.

When it is decided in step S124 that $Q \geq C_3$ does not hold, in other words, $Q < C_3$ holds, it is decided in step S127 that the risk of becoming OSAS is low.

In step S128, the result of decision that the risk of becoming OSAS is low is output to, for example, the display.

Example 6

From FIG. 51 to FIG. 73 which show the tracings made based on the cephalometric radiograms of the patients 31 to 53 the distances (Go-A) and (Go-B) were measured, $P=((Go\text{-}A)-(Go\text{-}B))/(Go\text{-}B)$ was calculated and $Q=P\times 1000$ was calculated.

The distance (Go-A) and the distance (Go-B) which were measured from FIG. 51 to FIG. 73 and Q are as follows. AHI and $Sao_2$ or $SpO_2$ of the patients 31 to 53 obtained by PSG were the same as the Example 4.

| Patient | (Go-A) (mm) | (Go-B) (mm) | Q |
|---|---|---|---|
| 31 | 79 | 66 | 196 |
| 32 | 86 | 71 | 211 |
| 33 | 77 | 65 | 184 |
| 34 | 80 | 66 | 212 |
| 35 | 82 | 75 | 93 |
| 36 | 78 | 67 | 164 |
| 37 | 72 | 64 | 125 |
| 38 | 82 | 74 | 108 |
| 39 | 87 | 67 | 298 |
| 40 | 78 | 70 | 114 |
| 41 | 96 | 85 | 129 |
| 42 | 80 | 65 | 230 |
| 43 | 84 | 71 | 183 |
| 44 | 83 | 68 | 220 |
| 45 | 81 | 68 | 191 |
| 46 | 85 | 70 | 214 |
| 47 | 72 | 60 | 200 |
| 48 | 82 | 70 | 171 |
| 49 | 82 | 72 | 138 |
| 50 | 77 | 67 | 149 |
| 51 | 86 | 78 | 102 |
| 52 | 83 | 73 | 136 |
| 53 | 87 | 76 | 144 |

As a control group, the subjects 54 to 65 were adopted. From FIG. 74 to FIG. 85 which show the tracings made based on the cephalometric radiograms of the subjects 54 to 65 the distances (Go-A) and (Go-B) were measured, $P=((Go\text{-}A)-(Go\text{-}B))/(Go\text{-}B)$ was calculated and $Q=P\times 1000$ was calculated.

The distance (Go-A) and the distance (Go-B) which were measured from FIG. 74 to FIG. 85 and Q are as follows.

| Subject | (Go-A) (mm) | (Go-B) (mm) | Q |
|---|---|---|---|
| 54 | 77 | 78 | −12 |
| 55 | 78 | 80 | −25 |
| 56 | 85 | 80 | 62 |
| 57 | 78 | 76 | 26 |
| 58 | 74 | 73 | 13 |
| 59 | 79 | 80 | −12 |
| 60 | 86 | 73 | 178 |
| 61 | 79 | 80 | −12 |
| 62 | 81 | 74 | 94 |
| 63 | 83 | 72 | 152 |
| 64 | 78 | 69 | 130 |
| 65 | 87 | 70 | 242 |

Figure 90:
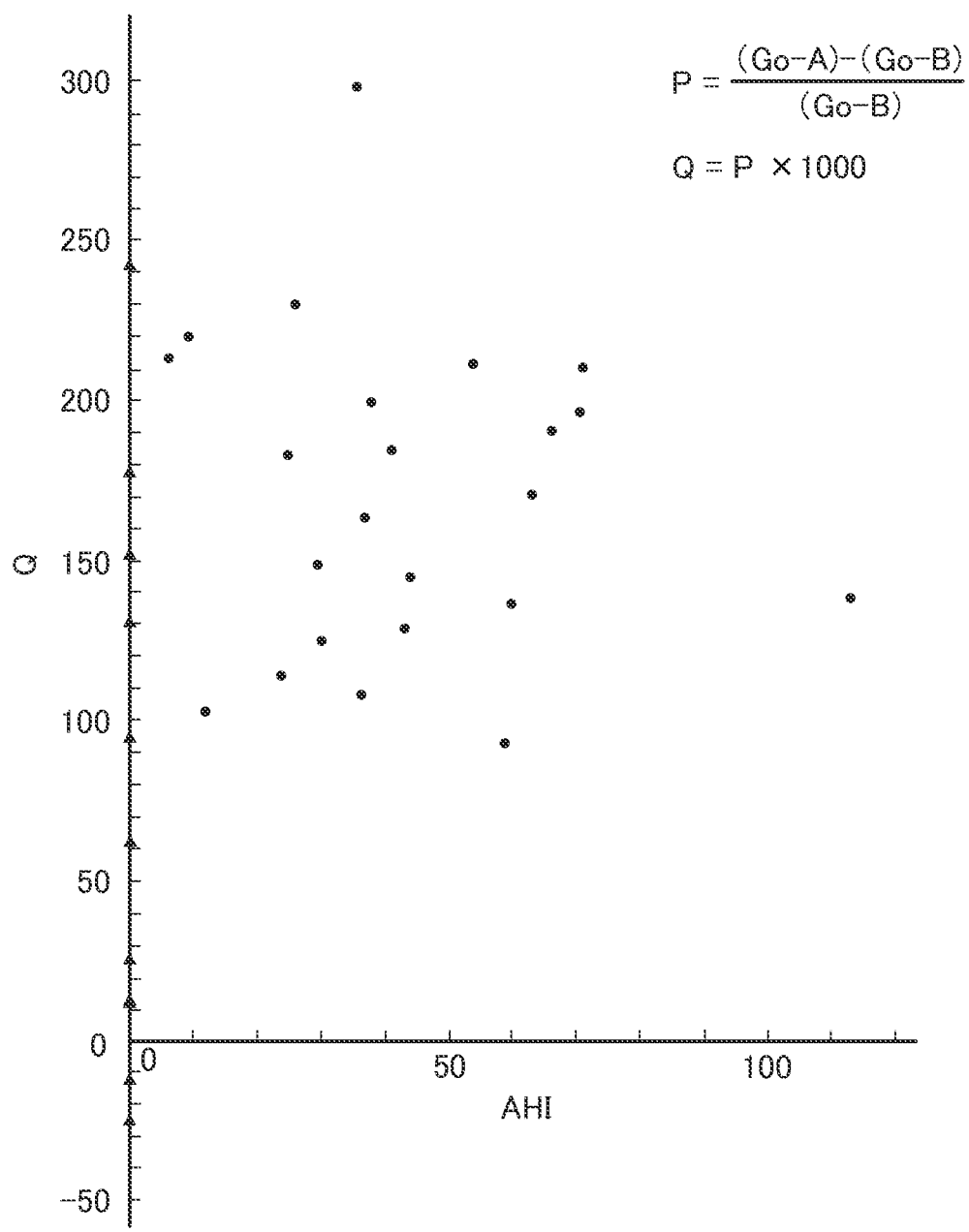
FIG. 90 A schematic drawing showing the result of calculation of the OSAS index Q of the patients 31 to 53 and the subjects 54 to 65 in the twelfth embodiment of the invention.

FIG. 90 shows the result of plotting the values of AHI and Q of the patients 31 to 53. In FIG. 90, the values of Q of the subjects 54 to 65 are plotted on the line of AHI=0. It is understood from FIG. 90 that Q of the subjects 54 to 65 distribute in the wide range from −25 to 195, whereas Q of the patients 31 to 53 distribute in the range from 93 to 298 in a concentrated way, and both distributions are quite different. Therefore, by using the difference of distributions, it is possible to decide the risk of OSAS by the value of Q.

According to the method of deciding the risk of obstructive sleep apnea syndrome according to the twelfth embodiment, based on the distances (Go-A) and (Go-B) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

13. The Thirteenth Embodiment

In the thirteenth embodiment, the method of deciding the risk of obstructive sleep apnea syndrome is described.

Figure 91:
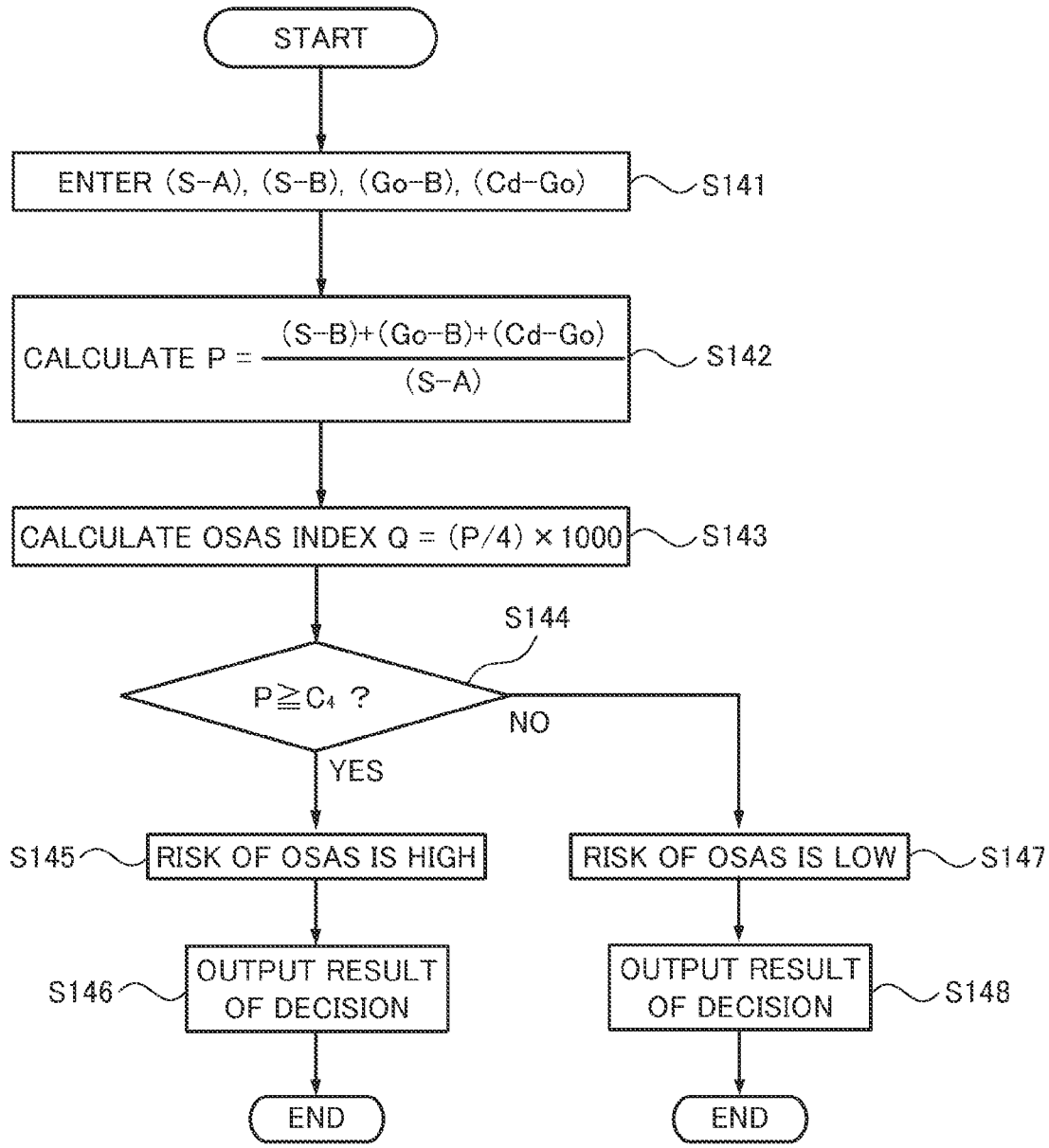
FIG. 91 A flow chart showing a method of deciding the risk of obstructive sleep apnea syndrome according to the thirteenth embodiment of the invention.

FIG. 91 shows a flow chart of the method of deciding the risk of obstructive sleep apnea syndrome. Programs are created according to the flow chart and are executed on a computer.

As the same as the tenth embodiment, before carrying out the method of deciding the risk of obstructive sleep apnea syndrome, the distances (S-A), (S-B), (Go-B) and (Cd-Go) are measured.

As shown in FIG. 91, in step S141, the distances (S-A), (S-B), (Go-B) and (Cd-Go) which are measured as described above are entered.

In step S142, from the entered distances (S-A), (S-B), (Go-B) and (Cd-Go), P is calculated according to $$P=((S\text{-}B)+(Go\text{-}B)+(Cd\text{-}Go))/(S\text{-}A).$$

In step S143, after P/4 is calculated from P calculated as described above and the figures of the fourth decimal place and under of P/4 are omitted and $$Q=(P/4)-1000$$

is calculated.

In step S144, from Q obtained by the above calculation, it is decided whether $Q \geq C_4$ or not.

When $Q \geq C_4$, it is decided in step S145 that the risk of becoming OSAS is high. For example, when $Q \geq 693$, it is decided that the risk of becoming OSAS is high. In this case, further, when Q≥720, for example, it may be decided that the risk of becoming OSAS is especially high.

In step S146, the result of decision that the risk of becoming OSAS is high is output to, for example, the display.

When it is decided in step S144 that Q≥$C_4$ does not hold, in other words, Q<$C_4$, it is decided in step S147 that the risk of becoming OSAS is low.

In step S148, the result of decision that the risk of becoming OSAS is low is output to, for example, the display.

Example 7

From FIG. 51 to FIG. 73 which show the tracings made based on the cephalometric radiograms of the patients 31 to 53 the distances (S-A), (S-B), (Go-B) and (Cd-Go) were measured, P=((S-B)+(Go-B)+(Cd-Go))/(S-A) was calculated and Q=(P/4)×1000 was calculated.

The distances (S-A), (S-B), (Go-B) and (Cd-Go) which were measured from FIG. 51 to FIG. 73 and Q were as follows. AHI and $Sao_2$ or $SpO_2$ of the patients 31 to 53 were the same as the Example 4.

| Patient | (S-A) (mm) | (S-B) (mm) | (Go-B) (mm) | (Cd-Go) (mm) | Q |
|---|---|---|---|---|---|
| 31 | 75 | 106 | 66 | 68 | 800 |
| 32 | 83 | 111 | 71 | 67 | 750 |
| 33 | 77 | 104 | 65 | 63 | 753 |
| 34 | 79 | 103 | 66 | 60 | 724 |
| 35 | 84 | 117 | 75 | 64 | 761 |
| 36 | 78 | 108 | 67 | 60 | 753 |
| 37 | 79 | 102 | 64 | 60 | 715 |
| 38 | 89 | 121 | 74 | 71 | 747 |
| 39 | 83 | 111 | 67 | 68 | 740 |
| 40 | 80 | 111 | 70 | 59 | 750 |
| 41 | 88 | 115 | 85 | 65 | 752 |
| 42 | 80 | 105 | 65 | 68 | 743 |
| 43 | 83 | 109 | 71 | 64 | 734 |
| 44 | 83 | 111 | 68 | 60 | 719 |
| 45 | 79 | 103 | 68 | 66 | 750 |
| 46 | 84 | 108 | 70 | 61 | 711 |
| 47 | 70 | 108 | 60 | 61 | 760 |
| 48 | 70 | 97 | 70 | 56 | 717 |
| 49 | 85 | 115 | 72 | 59 | 756 |
| 50 | 77 | 101 | 67 | 60 | 693 |
| 51 | 80 | 107 | 78 | 48 | 747 |
| 52 | 85 | 113 | 73 | 63 | 731 |
| 53 | 83 | 111 | 76 | 59 | 773 |

As a control group, the subjects 54 to 65 were adopted. From FIG. 74 to FIG. 85 which show the tracings made based on the cephalometric radiograms of the subjects 54 to 65 the distances (S-A), (S-B), (Go-B) and (Cd-Go) were measured, P=((S-B)+(Go-B)+(Cd-Go))/(S-A) were calculated and Q=(P/4)×1000 was calculated.

The distances (S-A), (S-B), (Go-B) and (Cd-Go) which were measured from FIG. 74 to FIG. 85 and Q were as follows.

| Subject | (S-A) (mm) | (S-B) (mm) | (Go-B) (mm) | (Cd-Go) (mm) | Q |
|---|---|---|---|---|---|
| 54 | 78 | 123 | 78 | 60 | 836 |
| 55 | 83 | 123 | 80 | 68 | 816 |
| 56 | 88 | 126 | 80 | 66 | 772 |
| 57 | 85 | 119 | 76 | 67 | 770 |
| 58 | 75 | 109 | 73 | 59 | 803 |
| 59 | 87 | 128 | 80 | 68 | 793 |
| 60 | 86 | 111 | 73 | 57 | 700 |
| 61 | 90 | 127 | 80 | 65 | 755 |
| 62 | 79 | 105 | 74 | 50 | 724 |
| 63 | 81 | 103 | 72 | 64 | 737 |
| 64 | 81 | 108 | 69 | 63 | 740 |
| 65 | 91 | 115 | 70 | 70 | 670 |

Figure 92:
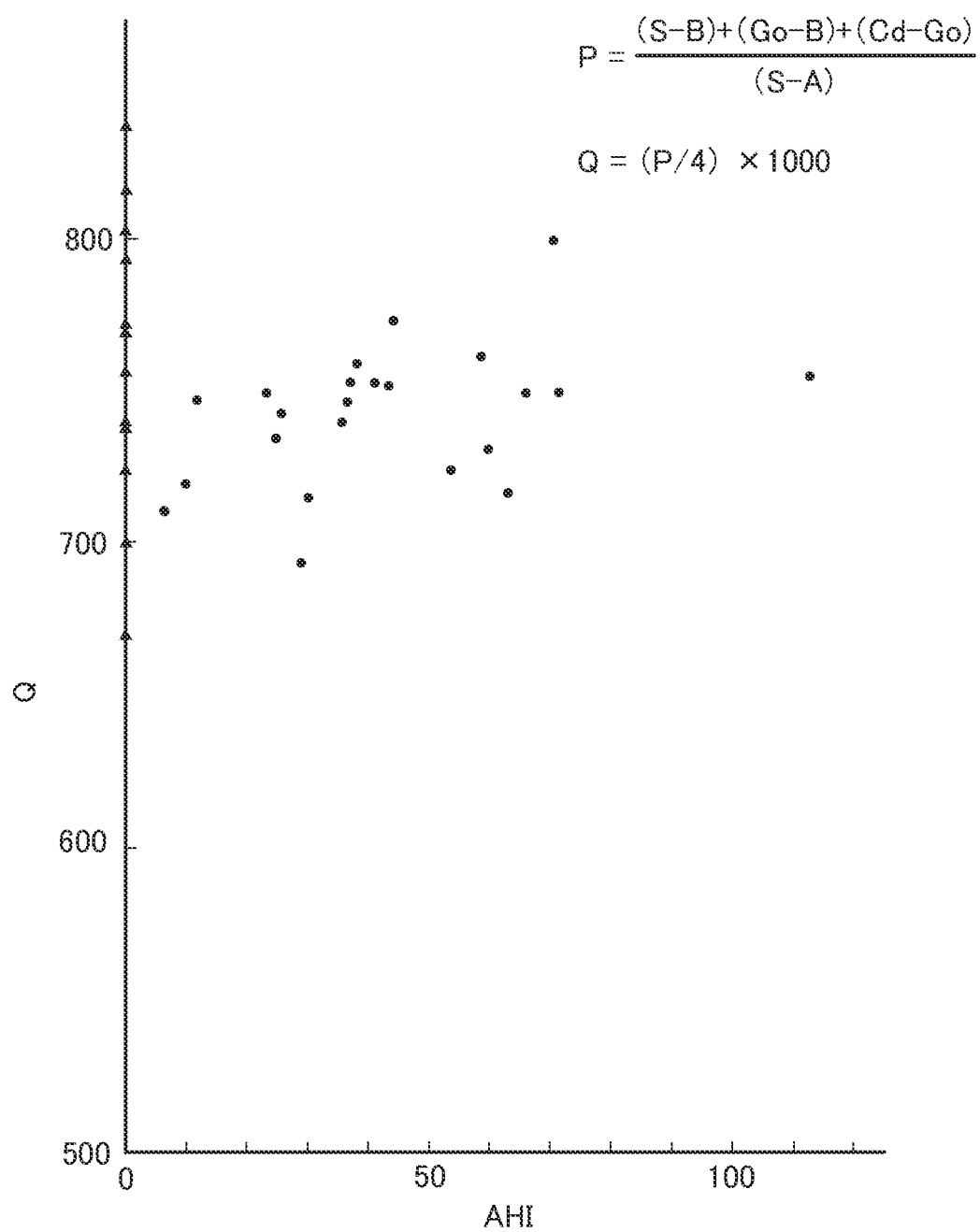
FIG. 92 A schematic drawing showing the result of calculation of the OSAS index Q of the patients 31 to 53 and the subjects 54 to 65 in the thirteenth embodiment of the invention.

FIG. 92 shows the result of plotting the values of AHI and Q of the patients 31 to 53. In FIG. 92, the values of Q of the subjects 54 to 65 are plotted on the line of AHI=0. It is understood from FIG. 92 that Q of the subjects 54 to 65 distribute in the wide range from 670 to 836, whereas Q of the patients 31 to 53 distribute in the range from 693 to 800 in a concentrated way, and both distributions are quite different. Therefore, by using the difference of distributions, it is possible to decide the risk of OSAS by the value of Q.

According to the method of deciding the risk of obstructive sleep apnea syndrome according to the thirteenth embodiment, based on the distances (S-A), (S-B), (Go-B) and (Cd-Go) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

14. The Fourteenth Embodiment

In the fourteenth embodiment, the method of deciding the risk of obstructive sleep apnea syndrome is described.

Figure 93:
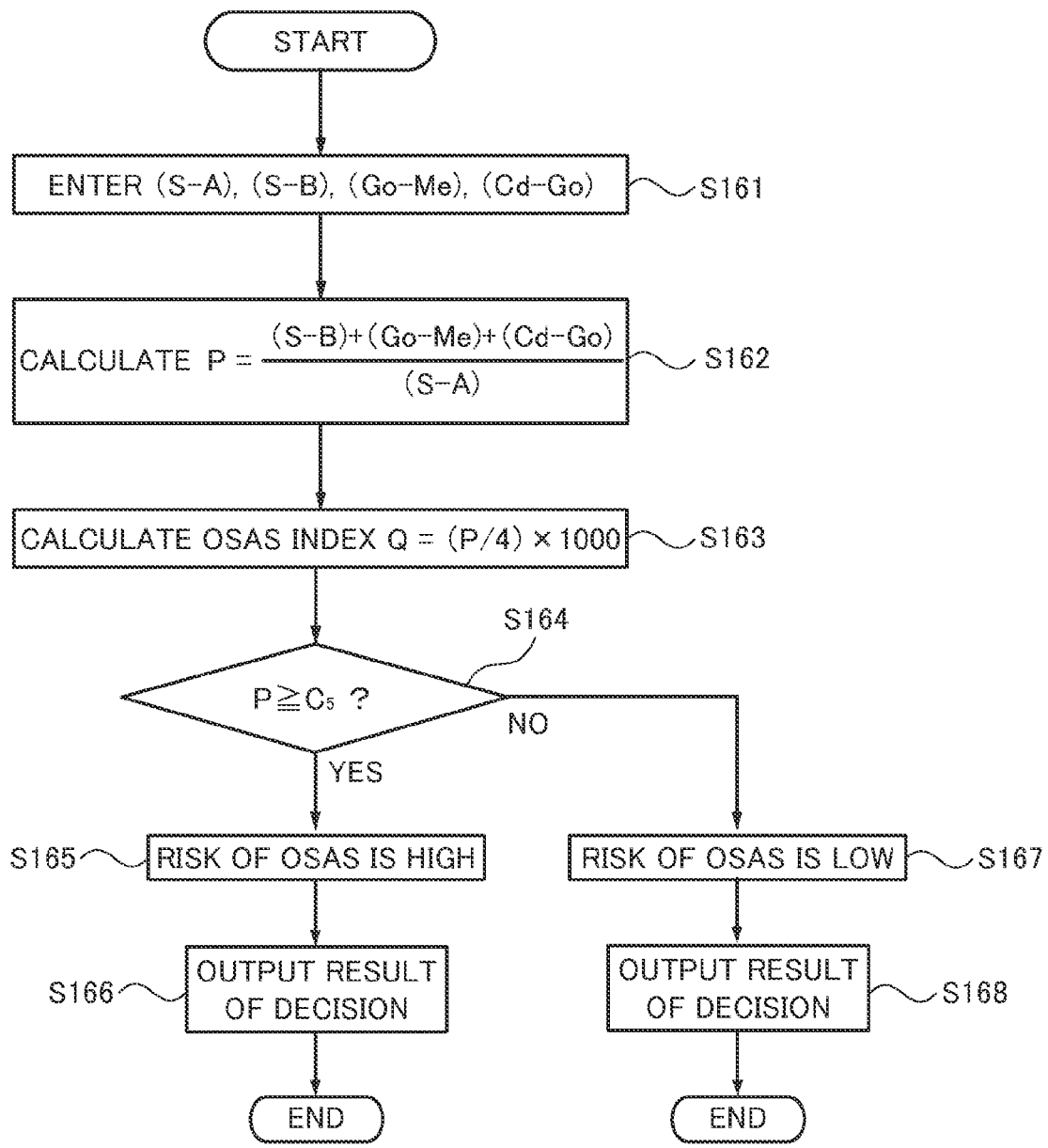
FIG. 93 A flow chart showing a method of deciding the risk of obstructive sleep apnea syndrome according to the fourteenth embodiment of the invention.

FIG. 93 shows a flow chart of the method of deciding the risk of obstructive sleep apnea syndrome. Programs are created according to the flow chart and are executed on a computer.

As the same as the tenth embodiment, before carrying out the method of deciding the risk of obstructive sleep apnea syndrome, the distances (S-A), (S-B), (Go-Me) and (Cd-Go) are measured.

As shown in FIG. 93, in step S161, the distances (S-A), (S-B), (Go-Me) and (Cd-Go) which are measured as described above are entered.

In step S162, from the entered distances (S-A), (S-B), (Go-Me) and (Cd-Go), P is calculated according to $$P=((S\text{-}B)+(Go\text{-}Me)+(Cd\text{-}Go))/(S\text{-}A).$$

In step S163, after P/4 is calculated from P calculated as described above and the figures of the fourth decimal place and under of P/4 are omitted and $$Q=(P/4)\times 1000$$

is calculated.

In step S164, from Q obtained by the above calculation, it is decided whether Q≥$C_5$ or not.

When Q<$C_5$, it is decided in step S165 that the risk of becoming OSAS is high. For example, when Q≥703, it is decided that the risk of becoming OSAS is high. In this case, further, when Q≥720, for example, it may be decided that the risk of becoming OSAS is especially high.

In step S166, the result of decision that the risk of becoming OSAS is high is output to, for example, the display.

When it is decided in step S164 that $Q \geq C_5$ does not hold, in other words, $Q < C_5$, it is decided in step S167 that the risk of becoming OSAS is low.

In step S168, the result of decision that the risk of becoming OSAS is low is output to, for example, the display.

Example 8

From FIG. 51 to FIG. 73 which show the tracings made based on the cephalometric radiograms of the patients 31 to 53 the distances (S-A), (S-B), (Go-Me) and (Cd-Go) were measured, P=((S-B)+(Go-Me)+(Cd-Go))/(S-A) was calculated and Q=(P/4)×1000 was calculated.

The distances (S-A), (S-B), (Go-Me) and (Cd-Go) which were measured from FIG. 51 to FIG. 73 and Q were as follows. AHI and $SaO_2$ or $SpO_2$ of the patients 31 to 53 obtained by PSG were the same as the Example 4.

| Patient | (S-A) (mm) | (S-B) (mm) | (Go-Me) (mm) | (Cd-Go) (mm) | Q |
|---|---|---|---|---|---|
| 31 | 75 | 106 | 65 | 68 | 796 |
| 32 | 83 | 111 | 67 | 67 | 737 |
| 33 | 77 | 104 | 68 | 63 | 762 |
| 34 | 79 | 103 | 65 | 60 | 721 |
| 35 | 84 | 117 | 76 | 64 | 764 |
| 36 | 78 | 108 | 70 | 60 | 762 |
| 37 | 79 | 102 | 69 | 60 | 731 |
| 38 | 89 | 121 | 75 | 71 | 750 |
| 39 | 83 | 111 | 65 | 68 | 734 |
| 40 | 80 | 111 | 70 | 59 | 750 |
| 41 | 88 | 115 | 81 | 65 | 741 |
| 42 | 80 | 105 | 60 | 68 | 728 |
| 43 | 83 | 109 | 67 | 64 | 722 |
| 44 | 83 | 111 | 65 | 60 | 710 |
| 45 | 79 | 103 | 65 | 66 | 740 |
| 46 | 84 | 108 | 70 | 61 | 711 |
| 47 | 70 | 108 | 61 | 61 | 764 |
| 48 | 70 | 97 | 70 | 56 | 717 |
| 49 | 85 | 115 | 70 | 59 | 750 |
| 50 | 77 | 101 | 70 | 60 | 703 |
| 51 | 80 | 107 | 77 | 48 | 744 |
| 52 | 85 | 113 | 73 | 63 | 731 |
| 53 | 83 | 111 | 73 | 59 | 764 |

As a control group, the subjects 54 to 65 were adopted. From FIG. 74 to FIG. 85 which show the tracings made based on the cephalometric radiograms of the subjects 54 to 65 the distances (S-A), (S-B), (Go-Me) and (Cd-Go) were measured, P=((S-B)+(Go-Me)+(Cd-Go))/(S-A) was calculated and Q=(P/4)×1000 was calculated.

The distances (S-A), (S-B), (Go-Me) and (Cd-Go) which were measured from FIG. 74 to FIG. 85 and Q are as follows.

| Subject | (S-A) (mm) | (S-B) (mm) | (Go-Me) (mm) | (Cd-Go) (mm) | Q |
|---|---|---|---|---|---|
| 54 | 78 | 123 | 78 | 60 | 836 |
| 55 | 83 | 123 | 81 | 68 | 819 |
| 56 | 88 | 126 | 78 | 66 | 767 |
| 57 | 85 | 119 | 77 | 67 | 773 |
| 58 | 75 | 109 | 70 | 59 | 793 |
| 59 | 87 | 128 | 80 | 68 | 793 |
| 60 | 86 | 111 | 69 | 57 | 688 |
| 61 | 90 | 127 | 80 | 65 | 755 |
| 62 | 79 | 105 | 73 | 50 | 721 |
| 63 | 81 | 103 | 70 | 64 | 731 |
| 64 | 81 | 108 | 68 | 63 | 737 |
| 65 | 91 | 115 | 65 | 70 | 656 |

Figure 94:
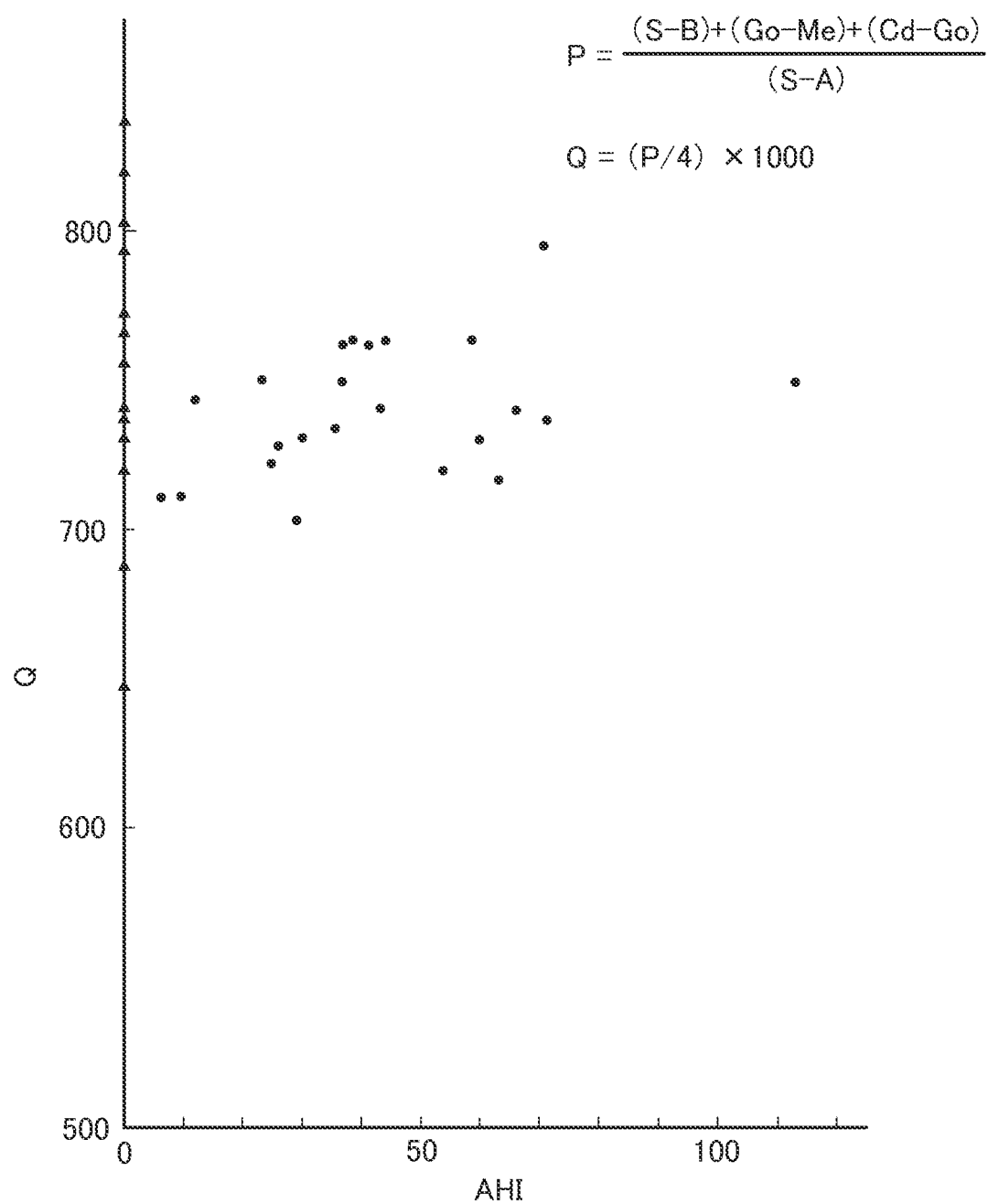
FIG. 94 A schematic drawing showing the result of calculation of the OSAS index Q of the patients 31 to 53 and the subjects 54 to 55 in the fourteenth embodiment of the invention.

FIG. 94 shows the result of plotting the values of AHI and P of the patients 31 to 53. In FIG. 94, the values of Q of the subjects 54 to 65 are plotted as the line of AHI=0. It is understood from FIG. 94 that Q of the subjects 54 to 65 distribute in the wide range from 656 to 836, whereas Q of the patients 31 to 53 distribute in the range from 710 to 796 in a concentrated way, and both distributions are quite different. Therefore, by using the difference of distributions, it is possible to decide the risk of OSAS by the value of Q.

According to the method of deciding the risk of obstructive sleep apnea syndrome according to the fourteenth embodiment, based on the distances (S-A), (S-B), (Go-Me) and (Cd-Go) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

15. The Fifteenth Embodiment

In the fifteenth embodiment, the method of deciding the risk of obstructive sleep apnea syndrome is described.

Figure 95:
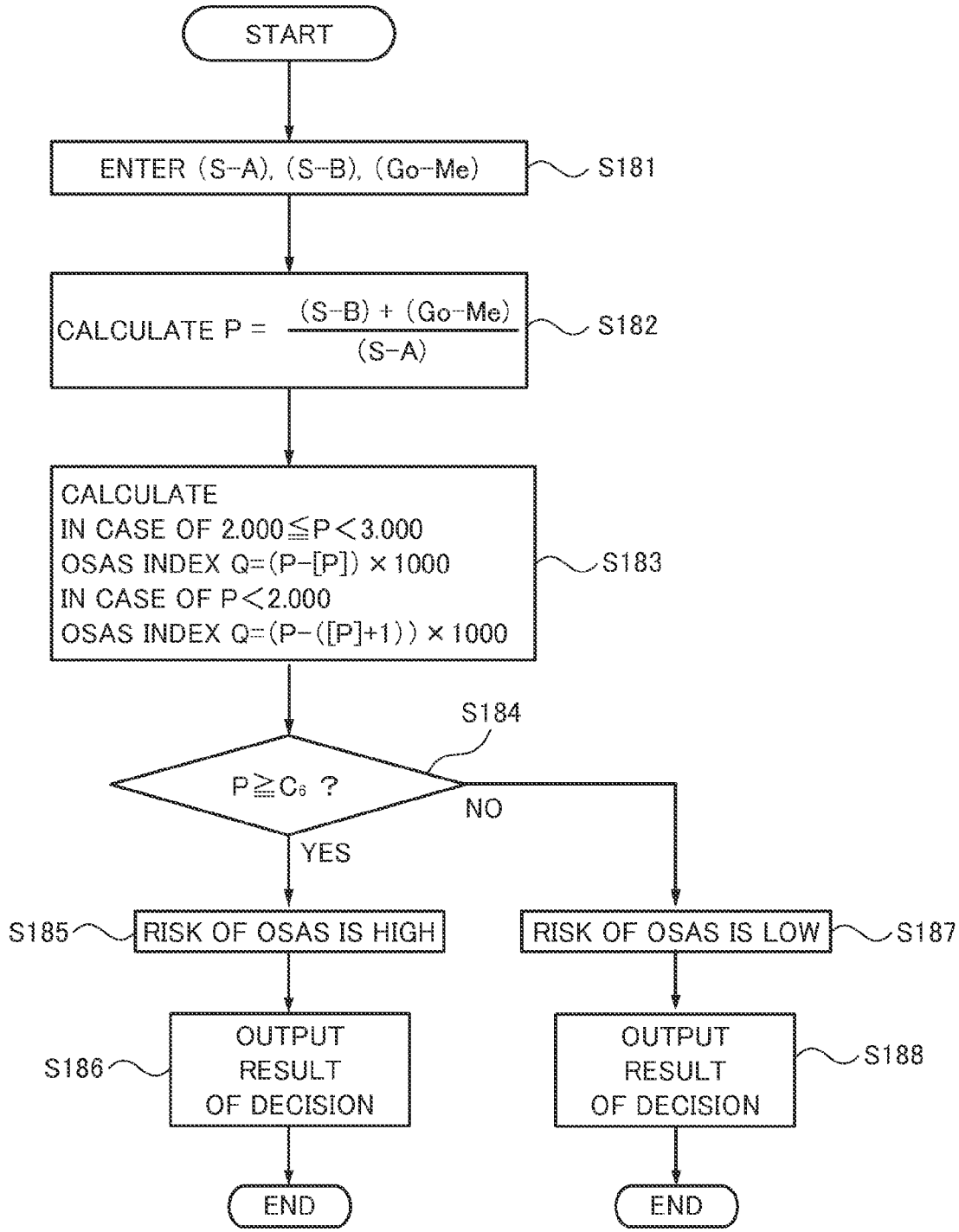
FIG. 95 A flow chart showing a method of deciding the risk of obstructive sleep apnea syndrome according to the fifteenth embodiment of the invention.

FIG. 95 shows a flow chart of the method of deciding the risk of obstructive sleep apnea syndrome. Programs are created according to the flow chart and are executed on a computer.

As the same as the tenth embodiment, before carrying out the method of deciding the risk of obstructive sleep apnea syndrome, the distances (S-A), (S-B) and (Go-Me) are measured.

As shown in FIG. 95, in step S181, the distances (S-A), (S-B) and (Go-Me) which are measured as described above are entered.

In step S182, from the entered distances (S-A), (S-B) and (Go-Me), P is calculated according to $$P=((S\text{-}B)+(Go\text{-}Me))/(S\text{-}A).$$

In step S183, after the figures of the fourth decimal place and under of P calculated as described above are omitted and $$Q=(P-[P])\times 1000 \text{ (where } 2.000 \leq P < 3.000)$$

or $$Q=(P-([P]+1))\times 1000 \text{ (where } P < 2.000)$$

is calculated.

In step S184, from Q obtained by the above calculation, it is decided whether $Q \geq C_6$ or not.

When $Q \geq C_6$, it is decided in step S186 that the risk of becoming OSAS is high. For example, when $Q \geq 62$, it is decided that the risk of becoming OSAS is high. In this case, further, when $Q \geq 120$, it may be decided that the risk of becoming OSAS is especially high.

In step S186, the result of decision that the risk of becoming OSAS is high is output to, for example, the display.

When it is decided in step S184 that $Q \geq C_6$ does not hold, in other words, $Q < C_6$, it is decided in step S187 that the risk of becoming OSAS is low.

In step S188, the result of decision that the risk of becoming OSAS is low is output to, for example, the display.

Example 9

From FIG. 51 to FIG. 73 which show the tracings made based on the cephalometric radiograms of the patients 31 to 53 the distances (S-A), (S-B) and (Go-Me) were measured, P=((S-B)+(Go-Me)/(S-A) was calculated and Q=(P−[P])×1000 or Q=(P−([P]+1))×1000 was calculated.

The distances (S-A), (S-B) and (Go-Me) which were measured from FIG. 51 to FIG. 73 and Q were as follows. AHI and SaO$_2$ or SpO$_2$ of the patients 31 to 53 obtained by PSG were the same as the Example 4.

| Patient | (S-A) (mm) | (S-B) (mm) | (Go-Me) (mm) | Q |
|---|---|---|---|---|
| 31 | 75 | 106 | 65 | 280 |
| 32 | 83 | 111 | 67 | 144 |
| 33 | 77 | 104 | 68 | 233 |
| 34 | 79 | 103 | 65 | 126 |
| 35 | 84 | 117 | 76 | 297 |
| 36 | 78 | 108 | 70 | 282 |
| 37 | 79 | 102 | 69 | 164 |
| 38 | 89 | 121 | 75 | 202 |
| 39 | 83 | 111 | 65 | 120 |
| 40 | 80 | 111 | 70 | 262 |
| 41 | 88 | 115 | 81 | 227 |
| 42 | 80 | 105 | 60 | 62 |
| 43 | 83 | 109 | 67 | 120 |
| 44 | 83 | 111 | 65 | 120 |
| 45 | 79 | 103 | 65 | 126 |
| 46 | 84 | 108 | 70 | 119 |
| 47 | 70 | 108 | 61 | 257 |
| 48 | 70 | 97 | 70 | 176 |
| 49 | 85 | 115 | 70 | 220 |
| 50 | 77 | 101 | 70 | 212 |
| 51 | 80 | 107 | 77 | 235 |
| 52 | 85 | 113 | 73 | 216 |
| 53 | 83 | 111 | 73 | 211 |

As a control group the subjects 54 to 65 were adopted. From FIG. 73 which show the tracings made based on the cephalometric radiograms of the subjects 54 to 65 the distances (S-A), (S-B) and (Go-Me) were measured, P=((S-B)+(Go-Me))/(S-A) was calculated and Q=(P−[P])×1000 or Q=(P−([P]+1))×1000 was calculated.

The distances (S-A), (S-B) and (Go-Me) which were measured from FIG. 51 to FIG. 73 and Q were as follows.

| Subject | (S-A) (mm) | (S-B) (mm) | (Go-Me) (mm) | Q |
|---|---|---|---|---|
| 54 | 78 | 123 | 78 | 576 |
| 55 | 83 | 123 | 81 | 457 |
| 56 | 88 | 126 | 78 | 318 |
| 57 | 85 | 119 | 77 | 305 |
| 58 | 75 | 109 | 70 | 386 |
| 59 | 87 | 128 | 80 | 390 |
| 60 | 86 | 111 | 69 | 93 |
| 61 | 90 | 127 | 80 | 300 |
| 62 | 79 | 105 | 73 | 253 |
| 63 | 81 | 103 | 70 | 135 |
| 64 | 81 | 108 | 68 | 172 |
| 65 | 91 | 115 | 65 | −22 |

Figure 96:
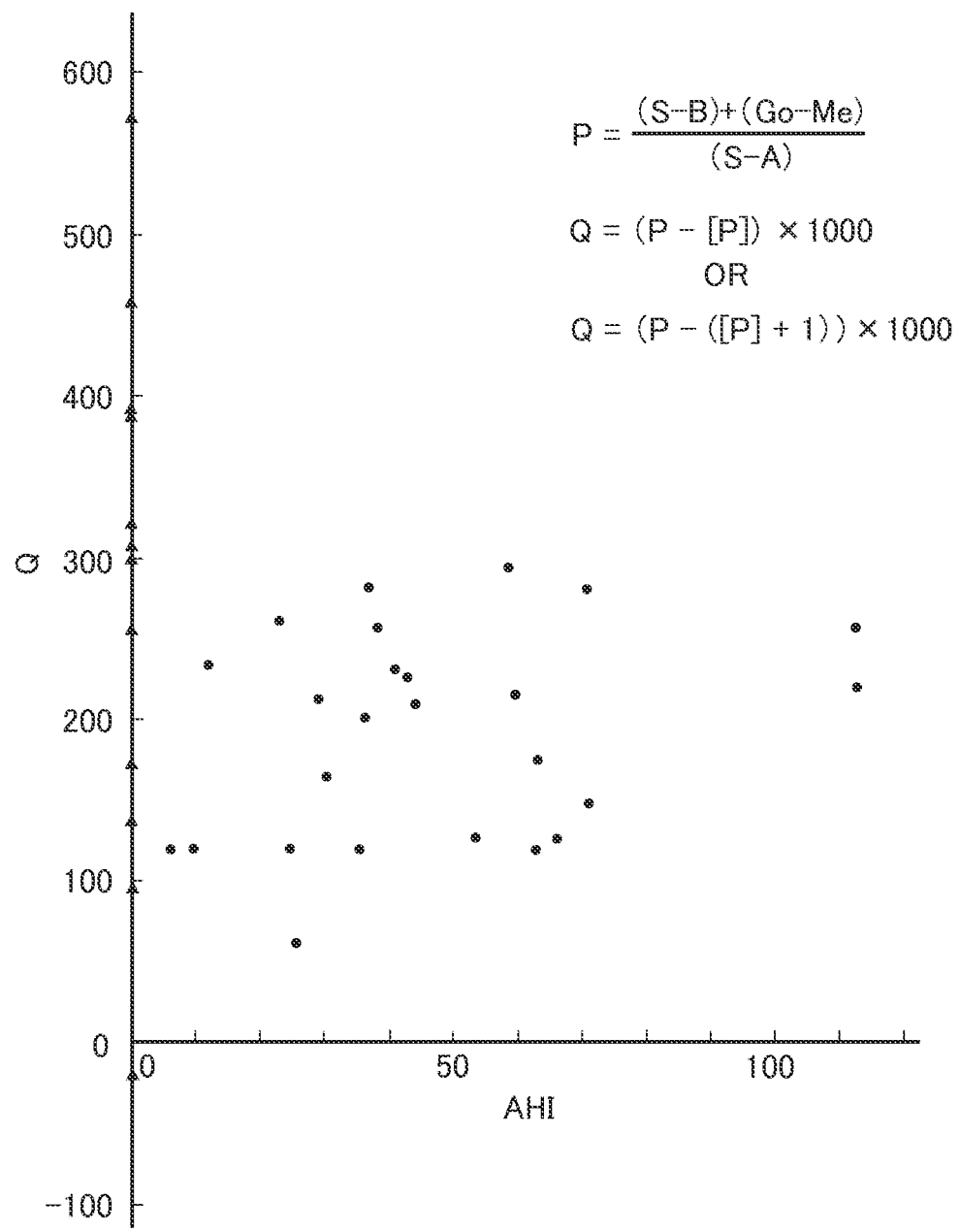
FIG. 96 A schematic drawing showing the result of calculation of the OSAS index Q of the patients 31 to 53 and the subjects 54 to 65 in the fifteenth embodiment of the invention.

FIG. 96 shows the result of plotting the values of AHI and Q of the patients 31 to 53. In FIG. 96, the values of Q of the subjects 54 to 65 are plotted on the line of AHI=0. It is understood from FIG. 96 that Q of the subjects 54 to 65 distribute in the wide range from −22 to 576, whereas Q of the patients 31 to 53 distribute in the range from 62 to 297 in a concentrated way, and both distributions are quite different. Therefore, by using the difference of distributions, it is possible to decide the risk of OSAS by the value of Q.

Here, Q can be used as an index for deciding disharmony of the maxilla and mandible and the degree of disharmony of the maxilla and mandible can be classified according to the values of Q. For example, the degree of disharmony of the maxilla and mandible is classified into below 0 (class 1), 1 to 150 (class 2), 151 to 250 (class 3), 251 to 300 (class 4), 301 to 350 (class 5), 351 to 400 (class 6) and above 401 (class 7) according to the value of Q. The class 1 corresponds to serious disharmony of the maxilla and mandible and shows dentofacial deformity. The class 2 shows medium to slight disharmony of the maxilla and mandible. The class 3 corresponds to the range that does not show disharmony of the maxilla and mandible and is considered that the skeletal patter is normal. The class 4 corresponds to slight disharmony of the maxilla and mandible. The class 5 corresponds to slight to medium disharmony of the maxilla and mandible. The class 6 corresponds to above medium disharmony of the maxilla and mandible. The class 7 corresponds to serious disharmony of the maxilla and mandible and shows dentofacial deformity. With respect to the patients 1 to 23, eight patients belong to the class 2, ten patients belong to the class 3, five patients belong to the class 4 and no patient belongs to the classes 1, 5 to 7. On the other hand, with respect to the subjects 24 to 35, one subject belongs to the class 1, two subjects belong to the class 2, one subject belongs to the class 3, two subjects belong to the class 4, two subjects belong to the class 5, two subjects belong to the class 6 and two subjects belong to the class 7. It should be noted that Q of the subjects 24 to 35 evenly distribute over the classes 1 to 7, whereas Q of the patients 1 to 23 concentrate in the classes 2 to 4.

According to the method of deciding the risk of obstructive sleep apnea syndrome according to the fifteenth embodiment, based on the distances (S-A), (S-B) and (Go-Me) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

16. The Sixteenth Embodiment

In the sixteenth embodiment, described is the method of deciding the risk of obstructive sleep apnea syndrome in which the distance (S-A) between S and A, the distance (S-$X_i$) between S and $X_i$ (i is an integer from 1 to 4. $X_1$=B, $X_2$=Pog, $X_3$=Gn and $X_4$=Me.) and the distance (Go-$X_j$) between Go and $X_j$ (j is an integer from 1 to 4. j=i or j≠i.) which are measured by cephalometric radiography of a subject are used and Q=(P−[P])×1000 or Q=(P−([P]+1))×1000 calculated by P=((S-$X_i$)+(Go-$X_j$))/(S-A)(where the case of $X_i$=B and $X_j$=Me is excluded) is used as an OSAS index.

Figure 97:
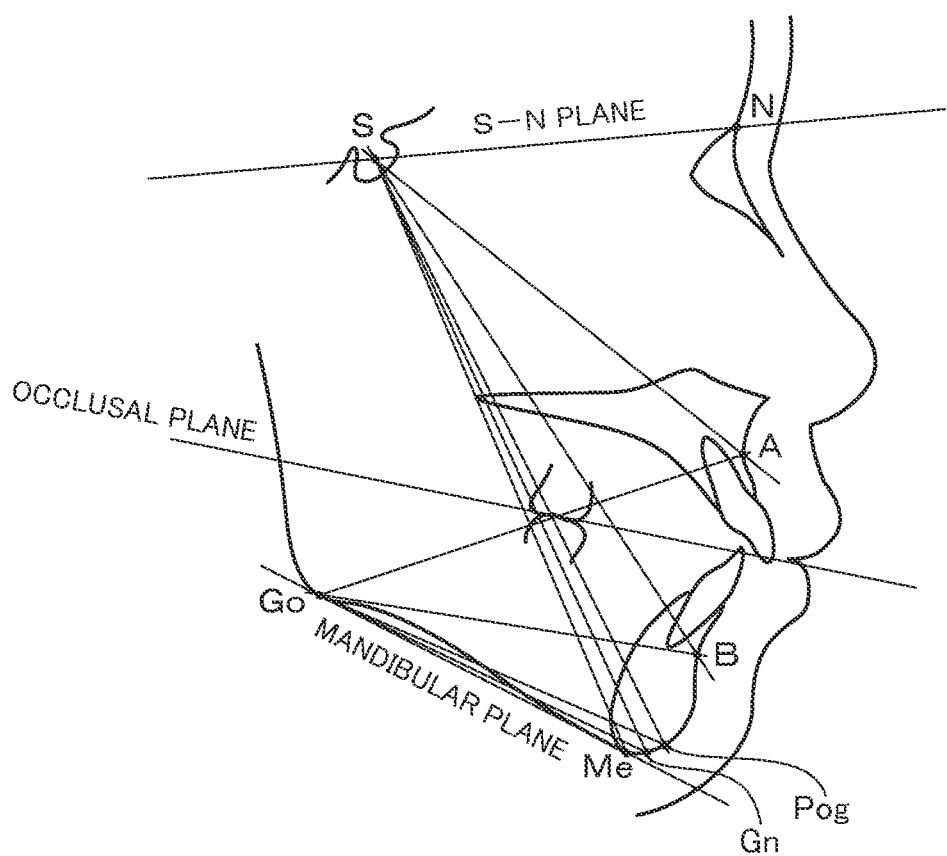
FIG. 97 A schematic drawing for explaining the measured points in the cephalometric radiogram that is used in a method of deciding the risk of obstructive sleep apnea syndrome according to the sixteenth embodiment of the invention.

Here, S, A, B, Go, Pog, Gn and Me are measured points to be obtained by cephalometric radiography. The positions of each measured point are shown in FIG. 97. "Pog" is an abbreviation of Pogonion, and is the most protruding point of protuberantia mentalis of the mandible for the Frankfort plane. "Gn" is an abbreviation of Gnathion, and is a cross point of the bone edge image of protuberantia mentalis and the bisector of the angle between the facial plane (the line connecting N (abbreviation of Nasion, and the front point of the frontal suture of the nasal bone) and Pog) and the mandibular plane.

Figure 98:
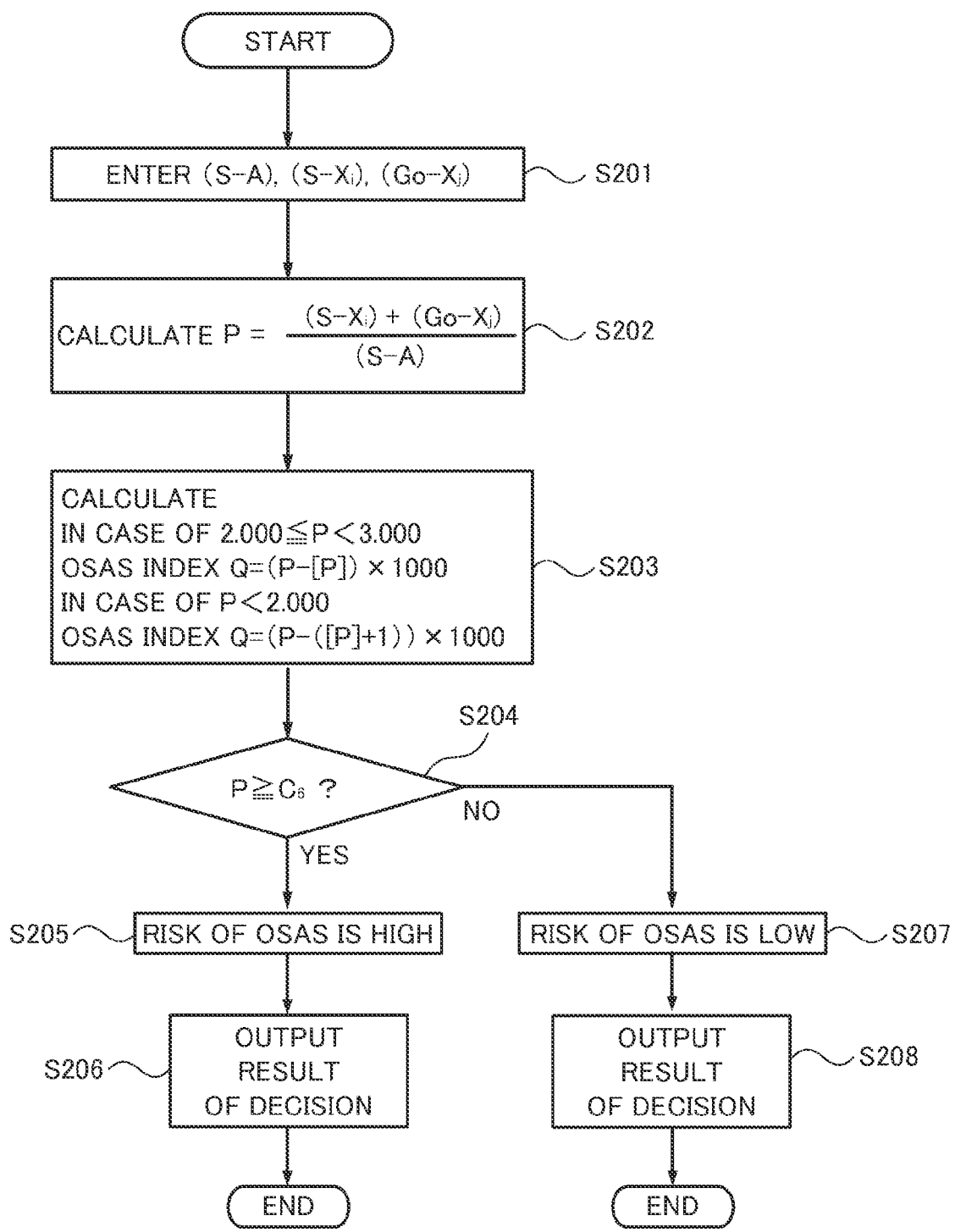
FIG. 98 A flow chart showing a method of deciding the risk of obstructive sleep apnea syndrome according to the sixteenth embodiment of the invention.

FIG. 98 shows a flow chart of the method of deciding the risk of obstructive sleep apnea syndrome. Programs are created according to the flow chart and are executed on a computer.

Before making the calculation, taking a cephalometric radiogram of a subject to be decided the risk of becoming OSAS, the distance (S-A) between S and A, the distance (S-$X_i$) between S and $X_i$ and the distance (Go-$X_j$) between Go and $X_j$ are measured. The measurement of the distances can be carried out as the same as the tenth embodiment.

As shown in FIG. 98, in step S201, the distances (S-A), (S-$X_i$) and (Go-X) which are measured as described above are entered.

In step S202, from the entered distances (S-A), (S-$X_i$) and (Go-$X_j$), P is calculated according to $$P=((S\text{-}X_i)+(Go\text{-}X_j))/(S\text{-}A).$$

In step S203, after the figures of the fourth decimal place and under of P calculated as described above are omitted and $$Q=(P-[P])\times1000 \text{ (where } 2.000 \leq P<3.000)$$

or $$Q=(P-([P]+1))\times1000 \text{ (where } P<2.000)$$

is calculated.

In step S204, the OSAS index Q calculated as described above is output to, for example, the display.

When the OSAS index Q calculated as described above is equal to or larger than the predetermined value $C_6$, it can be decided in view of skeletal pattern of the jaw that the risk of becoming OSAS is high. $C_6$ can be determined as needed, and is 62, for example.

When the OSAS index Q is smaller than $C_6$, it can be decided in view of skeletal pattern of the jaw that the risk of becoming OSAS is low.

Generally, a doctor finally decides the risk of becoming OSAS by using the result of other examinations conventionally used to examine OSAS etc. in addition to the OSAS index Q.

According to the method of deciding the risk of obstructive sleep apnea syndrome according to the sixteenth embodiment, based on the distances (S-A), (S-$X_i$) and (Go-$X_j$) which are measured by cephalometric radiography, it is possible to decide the risk of becoming OSAS objectively and in a short time with certain accuracy without depending on experiences of a doctor, and by combining the result of decision with the result of decision by the methods of deciding the risk of obstructive sleep apnea syndrome according to the first to the fourth embodiments, it is possible to decide the risk of becoming OSAS with higher accuracy.

17. The Seventeenth Embodiment

In the seventeenth embodiment, when the whole of the body of the hyoid bone detected by lateral head and neck radiography of the subject, not the center of the body of the hyoid bone as in the first to the third embodiments, is included in the area above the perpendicular drawn toward the extended line of the segment S-Go from Me, it is decided that there is no risk of obstructive sleep apnea syndrome, when the whole of the body of the hyoid bone is included in the area below the perpendicular drawn toward the extended line of the segment S-Go from Me, but not included in the area below the perpendicular drawn toward the extended line of the segment Cd-Go from Me, it is decided that there is the risk of obstructive sleep apnea syndrome, and when the whole of the body of the hyoid bone is included in the area below the perpendicular drawn toward the extended line of the segment Cd-Go from Me, it is decided that the risk of obstructive sleep apnea syndrome is higher. The case where the whole of the body of the hyoid bone extends over the areas above and below the perpendicular drawn toward the extended line of the segments S-Go from Me is a borderline case and it is decided that the risk of becoming obstructive sleep apnea syndrome is high. Furthermore, the case where the whole of the body of the hyoid bone extends over the areas above and below the perpendicular drawn toward the extended line of the segment Cd-Go from Me is also a borderline case and it is decided that the risk of becoming obstructive sleep apnea syndrome is higher.

Decision that which area the whole of the body of the hyoid bone belongs to can be carried out as the same as the first to the third embodiments.

According to the seventeenth embodiment, based on the whole of the body of the hyoid bone, S, Go, Me and Cd which are detected by lateral head and neck radiography, it is possible not only to decide the risk of becoming OSAS objectively and in a short time with certain accuracy without depending on experiences of a doctor but also to decide the degree of the risk of becoming OSAS.

Example 10

From FIG. 9 to FIG. 24 which show the tracings of the patients 1 to 16 in the Example 1 the whole of the body of the hyoid bone of the patients 1 to 16 were detected. As a result, areas in which the whole of the body of the hyoid bone locates were as follows.

| Patient | Area in which the whole of the body of the hyoid bone locates | Risk of becoming OSAS |
| --- | --- | --- |
| 1 | area 3 | yes(high) |
| 2 | area 3 | yes(high) |
| 3 | area 2, 3 | yes(high) |
| 4 | area 1, 2 | probable |
| 5 | area 3 | yes(high) |
| 6 | area 1, 2 | probable |
| 7 | area 2, 3 | yes(high) |
| 8 | area 2, 3 | yes(high) |
| 9 | area 2, 3 | yes(high) |
| 10 | area 3 | yes(high) |
| 11 | area 2, 3 | yes(high) |
| 12 | area 1, 2 | probable |
| 13 | area 1, 2, 3 | probable |
| 14 | area 3 | yes(high) |
| 15 | area 2, 3 | yes(high) |
| 16 | area 2, 3 | yes(high) |

From FIG. 25 to FIG. 29 which show the tracings of the subjects 17 to 21 the body of the hyoid bone of the subjects 17 to 21 was detected. As a result, areas in which the whole of the body of the hyoid bone were as follows.

| Subject | Area in which the center of the body of the hyoid bone locates | Risk of becoming OSAS |
|---|---|---|
| 17 | area 1 | no |
| 18 | area 1 | no |
| 19 | area 1 | no |
| 20 | area 1 | no |
| 21 | area 1 | no |

As understood from the above result, by taking a head and neck radiograph and detecting which of the areas 1, 2 and 3 the whole of the body of the hyoid bone locates from the image or the radiograph, the risk of becoming OSAS can be decided as the same the first to the third embodiments.

18. The Eighteenth Embodiment

In the eighteenth embodiment, instead of Me in the first to the third embodiments Gn near to Me is used. That is, in the eighteenth embodiment, when the center of the body of the hyoid bone is included in the area above the perpendicular drawn toward the extended line of the segment S-Go from Gn, it is decided that there is no risk of obstructive sleep apnea syndrome, when it is included in the area between the perpendicular drawn toward the extended line of the segment S-Go from Gn and the perpendicular drawn toward the extended line of the segment Cd-Go from Me, it is decided that there is the risk of obstructive sleep apnea syndrome and when it is included in the area below the perpendicular drawn toward the extended line of the segment Cd-Go from Me, it is decided that the risk of obstructive sleep apnea syndrome is higher.

According to the eighteenth embodiment, the same advantages as the first to the third embodiments can be obtained.

19. The Nineteenth Embodiment

In the nineteenth embodiment, it is not decided which area the center of the body of the hyoid bone belongs to as in the eighteenth embodiment, but it is decided which area the whole of the body of the hyoid bone belongs to. That is, in the nineteenth embodiment, when the whole of the body of the hyoid bone is included in the area above the perpendicular drawn toward the extended line of the segment S-Go from Gn, it is decided that there is no risk of obstructive sleep apnea syndrome, when it is included in the area below the perpendicular drawn toward the extended line of the segment S-Go from Gn, but it is not included in the area below the perpendicular drawn toward the extended line of the segment Cd-Go from Gn, it is decided that there is the risk of obstructive sleep apnea syndrome, and when it is included in the area below the perpendicular drawn toward the extended line of the segment Cd-Go from Gn, it is decided that the risk of obstructive sleep apnea syndrome is higher.

According to the nineteenth embodiment, the same advantage as the seventeenth embodiment can be obtained.

20. The Twentieth Embodiment

In the twentieth embodiment, instead of Me in the first to the third embodiments, Pog near to Me is used. That is, in the twentieth embodiment, when the center of the body of the hyoid bone is included in the area above the perpendicular drawn toward the extended line of the segment S-Go from Pog, it is decided that there is no risk of obstructive sleep apnea syndrome, when it is included in the area between the perpendicular drawn toward the extended line of the segment S-Go from Pog and the perpendicular drawn toward the extended line of the segment Cd-Go from Pog, it is decided that there is the risk of obstructive sleep apnea syndrome, and when it is included in the area below the perpendicular drawn toward the extended line of the segment Cd-Go from Pog, it is decided that the risk of obstructive sleep apnea syndrome is higher.

According to the twentieth embodiment, the same advantage as the seventeenth embodiment can be obtained.

21. The Twenty-First Embodiment

It the twenty-first embodiment, it is not decided which area the center of the body of the hyoid bone belongs to as in the twentieth embodiment, but it is decided which area the whole of the body of the hyoid bone belongs to. That is, in the twenty-first embodiment, when the whole of the body of the hyoid bone is included in the area above the perpendicular drawn toward the extended line of the segment S-Go from Pog, it is decided that there is no risk of obstructive sleep apnea syndrome, when it is included in the area below the perpendicular drawn toward the extended line of the segment S-Go from Pog, but it is not included in the area below the perpendicular drawn toward the extended line of the segment Cd-Go from Pog, it is decided that there is the risk of obstructive sleep apnea syndrome, and when it is included in the area below the perpendicular drawn toward the extended line of the segment Cd-Go from Pog, it is decided that the risk of obstructive sleep apnea syndrome is higher.

According to the twenty-first embodiment, the same advantage as the seventeenth embodiment can be obtained.

22. The Twenty-Second Embodiment

In the twenty-second embodiment, a method of making an oral appliance is described.

According to the method of making an oral appliance, using at least the hyoid bone, S, Go and Me which are detected by lateral head and neck radiography of a subject, it is decided whether the detected center of the body of the hyoid bone is included in the area above the perpendicular drawn toward the extended line of the segment S-Go from Me or not. Or, by further using Cd detected by lateral head and neck radiography of the subject, it is decided which area of the area above the perpendicular drawn toward the extended line of the segment S-Go from Me, the area between the perpendicular drawn toward the extended line of the segment S-Go from Me and the perpendicular drawn toward the extended line of the segment Cd-Go from Me and the area below the perpendicular drawn toward the extended line of the segment Cd-Go from Me the center of the body of the hyoid bone is included in.

Then, an oral appliance is made according to the result of decision. More specifically, when it is decided that the detected center of the body of the hyoid bone is not included in the area above the perpendicular drawn toward the extended line of the segment S-Go from Me, the oral appliance is made so that when the oral appliance is attached in the oral cavity of the subject, the hyoid bone is pulled up by forward movement of the mandible for the maxilla and as a result, the center of the body of the hyoid bone is included in the area above the perpendicular drawn toward the extended line of the segment S-Go from Me. Or, when it is decided that the detected center of the body of the hyoid bone is included in the area between the perpendicular drawn toward the extended line of the segment S-Go from Me and the perpendicular drawn toward the extended line of the segment Cd-Go from Me, the oral appliance is made so that when the oral appliance is attached in the oral cavity of the subject, by forward movement of the mandible for the maxilla, the center of body of the hyoid bone is included in the area above the perpendicular drawn toward the extended line of the segment S-Go from Me. Furthermore, when it is decided that the detected center of the body of the hyoid bone is included in the area below the perpendicular drawn toward the extended line of the segment Cd-Go from Me, the oral appliance is made so that when the oral appliance is attached in the oral cavity of the subject, by forward movement of the mandible for the maxilla, the center of the body of the hyoid bone is included in the area between the perpendicular drawn toward the extended line of the segment S-Go from Me and the perpendicular drawn toward the extended line of the segment Cd-Go from Me or the area above the perpendicular drawn toward the extended line of the segment S-Go from Me. In this case, it is possible to obtain the forward moving distance $\Delta$ of the mandible relative to centric occlusion easily.

Figure 99A:
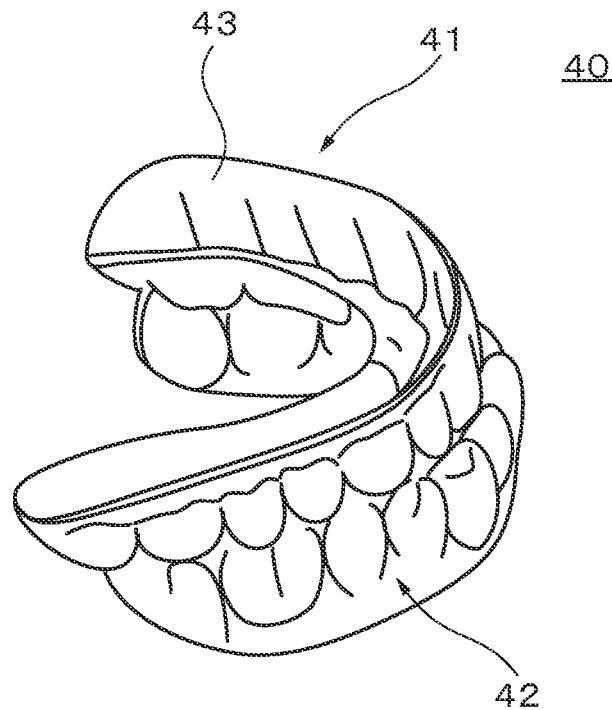
FIG. 99A A perspective view showing an oral appliance made by a method of making an oral appliance according to the twenty-second embodiment of the invention.
Figure 99B:
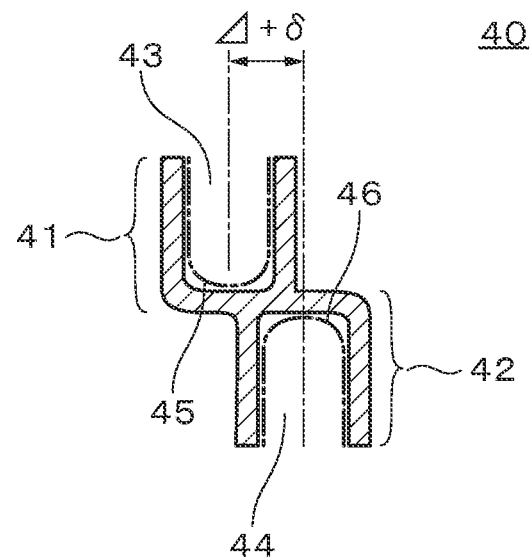
FIG. 99B A cross sectional view showing the oral appliance made by the method of making an oral appliance according to the twenty-second embodiment of the invention.
Figure 100A:
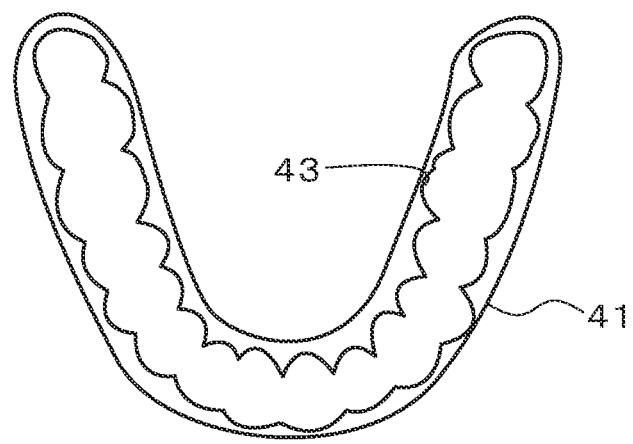
FIG. 100A A plan view showing the state where the maxilla part of the oral appliance made by the method of making the oral appliance according to the twenty-second embodiment of the invention is attached to the maxillary dentition.
Figure 100B:
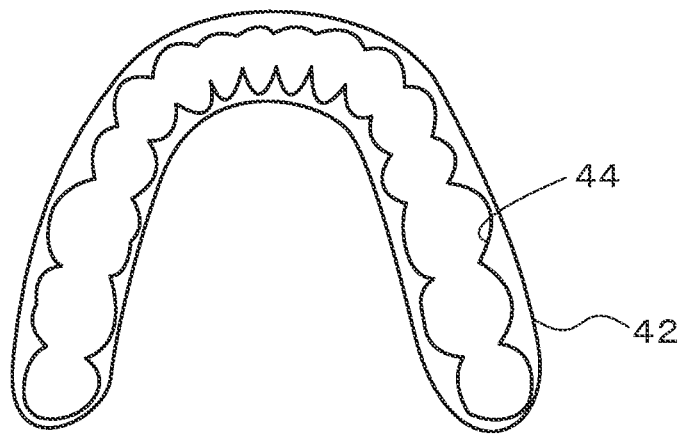
FIG. 100B A plan view showing the state where the mandible part of the oral appliance made by the method of making an oral appliance according to the twenty-second embodiment of the invention is attached to the mandibular dentition.

Then, respective plaster models of the maxillary dentition and the mandibular dentition of the subject are made. By using these plaster models, members for the maxilla and mandible (splint) are made by harmless materials for use in the oral cavity, typically resin. Finally, these members for the maxilla and mandible are combined as one body. In this case, these members for the maxilla and mandible are combined as one body so that the mandible moves forward by $\Delta$ obtained previously. In this way, the oral appliance of the type of forward holding and fixing the mandible is made. As resin, for example, acrylic resin can be used. An example of the oral appliance is shown in FIG. 99A and FIG. 99B. Here, FIG. 99B shows a cross sectional view of the part of the oral appliance shown in FIG. 99A corresponding to the central incisors. As shown in FIG. 99A and FIG. 99B, the oral appliance 40 is comprised of a maxilla part 41 and a mandible part 42. The maxilla part 41 has a part for accommodating dentition 43 of the maxilla and the mandible part 42 has apart for accommodating dentition 44 of the mandible. Reference numeral 45 denotes the central incisors of the maxilla and reference numeral 46 denotes the central incisors of the mandible. As shown in FIG. 99B, the mandible part 42 lies forward by $\Delta+\delta$ relative to the maxilla part 41. Here, $\delta$ shows the distance between the maxilla front teeth and the mandibular front teeth at centric occlusion. FIG. 100A illustrates the state where the maxilla dentition is accommodated in the part for accommodating dentition 43 of the maxilla part 41. FIG. 100B illustrates the state where the mandibular dentition is accommodated in the part for accommodating dentition 44 of the mandible part 42.

Members for the maxilla and mandible are generally made after impression taking, preparation of plaster model, etc., but it is possible to make them as follows. That is, first, the maxilla dentition and the mandibular dentition are photographed by a camera from at least two directions and three-dimensional images of the maxilla dentition and the mandibular dentition are obtained from the photographs. And using the three-dimensional coordinate data obtained from the three-dimensional images, the members for the maxilla and mandible are made by a 3D printer.

Described above is the method of making an oral appliance combining members for the maxilla and mandible as one body, but it is possible to make an oral appliance having members for the maxilla and mandible separated each other. For example, first, members for the maxilla and mandible are made as described above. Then, for example, a connecting member is attached to sides of the member for the maxilla and the member for the mandible so as to connect the both members. In this case, the connecting member is attached so that the mandible lies forward by $\Delta$ relative to the maxilla. The connecting member may be rotatable around the both ends in a constant angle range, or may be elastic in a constant range.

Here, described is the result of experiment to examine that when the mandible moves forward relative to the maxilla, how the hyoid bone moves.

Figure 101:
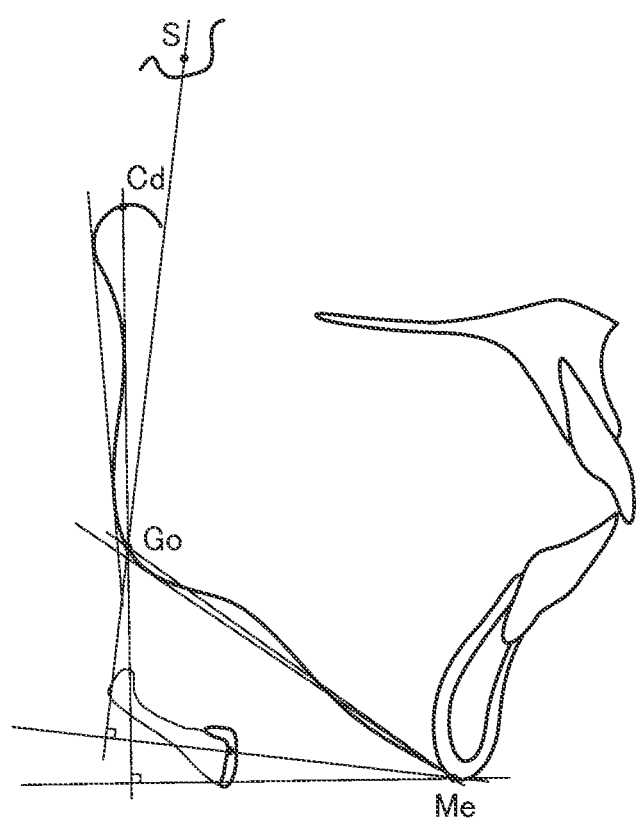
FIG. 101 A tracing made based on a lateral head and neck radiograph taken at centric occlusion of a subject 66.
Figure 102:
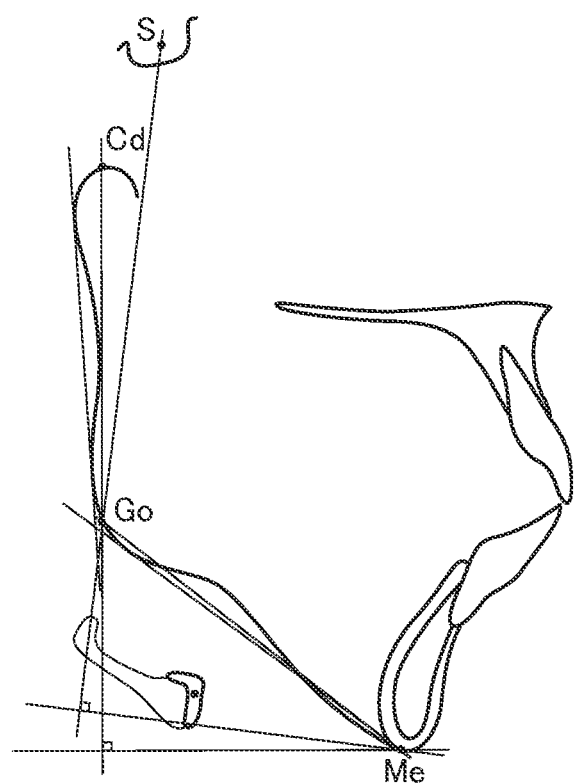
FIG. 102 A tracing made based on a lateral head and neck radiograph taken at edge to edge occlusion of the subject 66.
Figure 103:
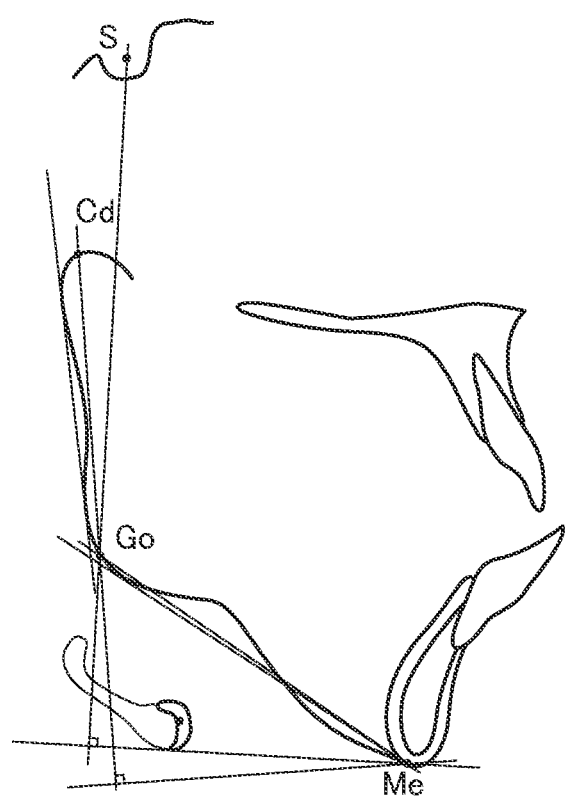
FIG. 103 A tracing made based on a lateral head and neck radiograph taken at a position moving the mandible forward for the maxilla of the subject 66.
Figure 104:
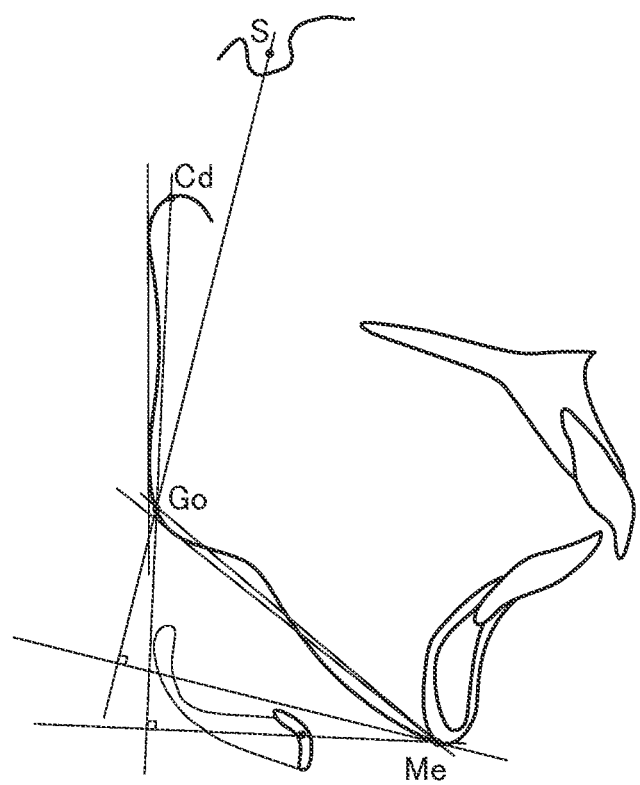
FIG. 104 A tracing made based on a lateral head and neck radiograph taken at centric occlusion of a subject 67.
Figure 105:
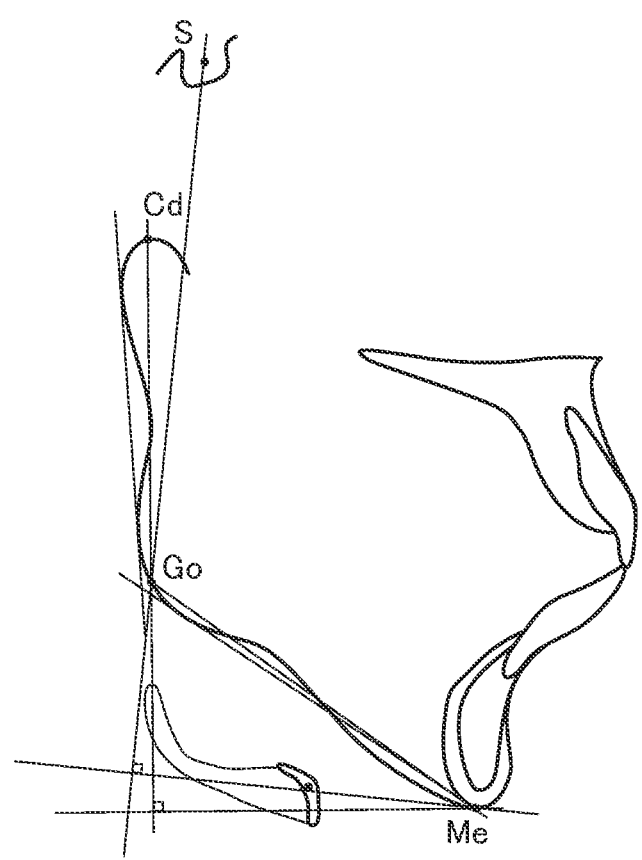
FIG. 105 A tracing made based on a lateral head and neck radiograph taken at edge to edge occlusion of the subject 67.
Figure 106:
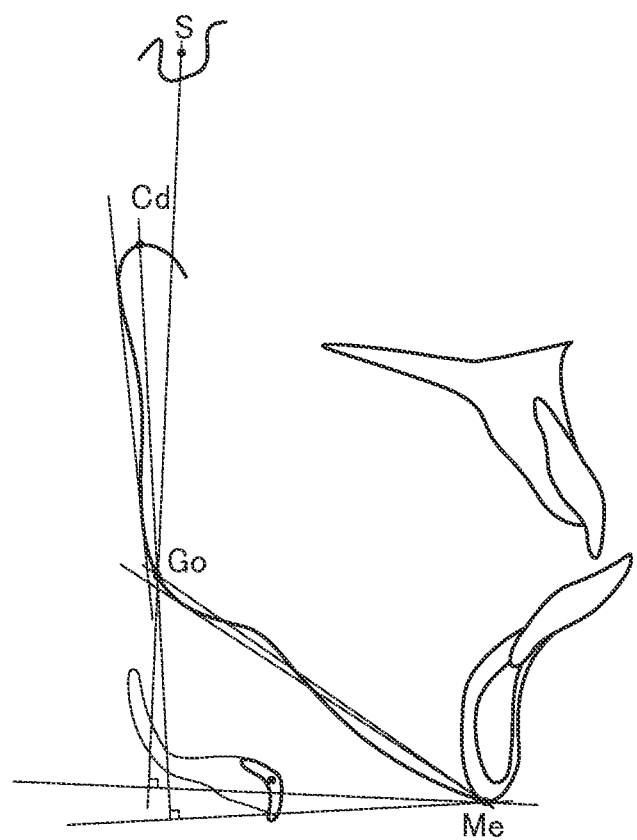
FIG. 106 A tracing made based on a lateral head and neck radiograph taken at a position moving the mandible forward for the maxilla of a subject 68.

FIG. 101, FIG. 102 and FIG. 103 show tracings made based on lateral head and neck radiographs of a subject 66 taken at centric occlusion, edge to edge occlusion and a position in which the mandible moves forward relative to edge to edge occlusion, respectively. FIG. 104, FIG. 105 and FIG. 106 show tracings made based on lateral head and neck radiographs of a subject 67 taken at centric occlusion, edge to edge occlusion and a position in which the mandible moves forward relative to edge to edge occlusion, respectively. As shown in FIG. 101, the center of the body of the hyoid bone of the subject 66 locates near the borders of the area 1 and the area 2 at centric occlusion and it is decided that the possibility of resulting the risk of obstructive sleep apnea syndrome is low. However, as shown in FIG. 102, at edge to edge occlusion in which the mandible moves forward by several millimeters, the center of the body of the hyoid bone is completely pulled up to the area 1. And, as shown in FIG. 103, at a position in which the mandible moves forward further than the edge to edge occlusion, the center of the body of the hyoid bone is also included in the area 1. Furthermore, as shown in FIG. 104, the center of the body of the hyoid bone of the subject 66 locates near the borders of the area 2 and the area 3 at centric occlusion and it is decided that there is the risk of obstructive sleep apnea syndrome or the risk is high. However, as shown in FIG. 105, at edge to edge occlusion in which the mandible moves forward by several millimeters, the center of the body of the hyoid bone is completely pulled up to the area 1. And, as shown in FIG. 106, at a position in which the mandible moves forward further than edge to edge occlusion, the center of the body of the hyoid bone is included in the area 1.

As described above, with respect to the subjects 66 and 67, it was possible to pull up the hyoid bone by moving the mandible forward. Based on the result, for example, with respect to the subjects 66 and 67, it can be decided that the oral appliance may be made so that the mandible moves forward by the same distance as FIG. 102 or FIG. 105. However, it is not always possible for all subjects to pull up the hyoid bone similarly by moving the mandible forward. And when the mandible moves forward by the same distance, the moving distance of the hyoid bone in the upward direction differs among the subjects. Furthermore, for particular subjects, it is almost impossible to pull up the hyoid bone by moving the mandible forward. Therefore, when the oral appliance is made, it is important to confirm previously the manner of movement of the hyoid bone when the mandible moves forward. In fact, for a certain subject, although the center of the body of the hyoid bone was included in the area 2, the body of the hyoid bone was pulled up by about 20 mm at a position in which the mandible moves forward by 5 mm than edge to edge occlusion and the center of the body of the hyoid bone became included in the area 1. In contrast to this, for another subject, although the center of the body of the hyoid bone was included in the area 3 at centric occlusion, the body of the hyoid bone did not almost move even in a position in which the mandible moved forward as much as possible than edge to edge occlusion and the center of the body of the hyoid bone remained in the area 3.

Here, explained is a data processor which is used to carry out the methods of deciding the risk of obstructive sleep apnea syndrome or the methods of deciding sinking of the hyoid bone according to the first to the sixteenth embodiments.

Figure 107:
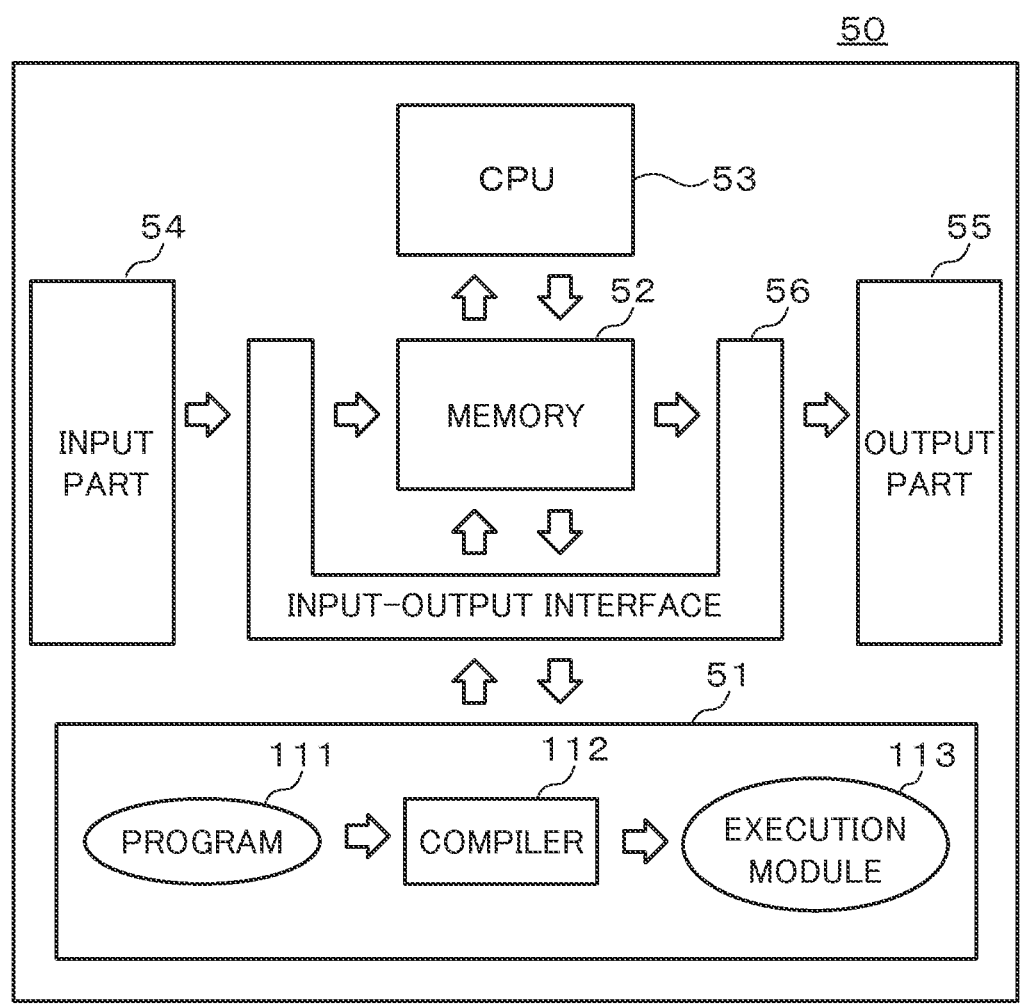
FIG. 107 A schematic drawing showing a data processor to be used for execution of the methods of deciding the risk of obstructive sleep apnea syndrome or the methods of deciding sinking of the hyoid bone according to the first to the sixteenth embodiments of the invention.
Figure 108:
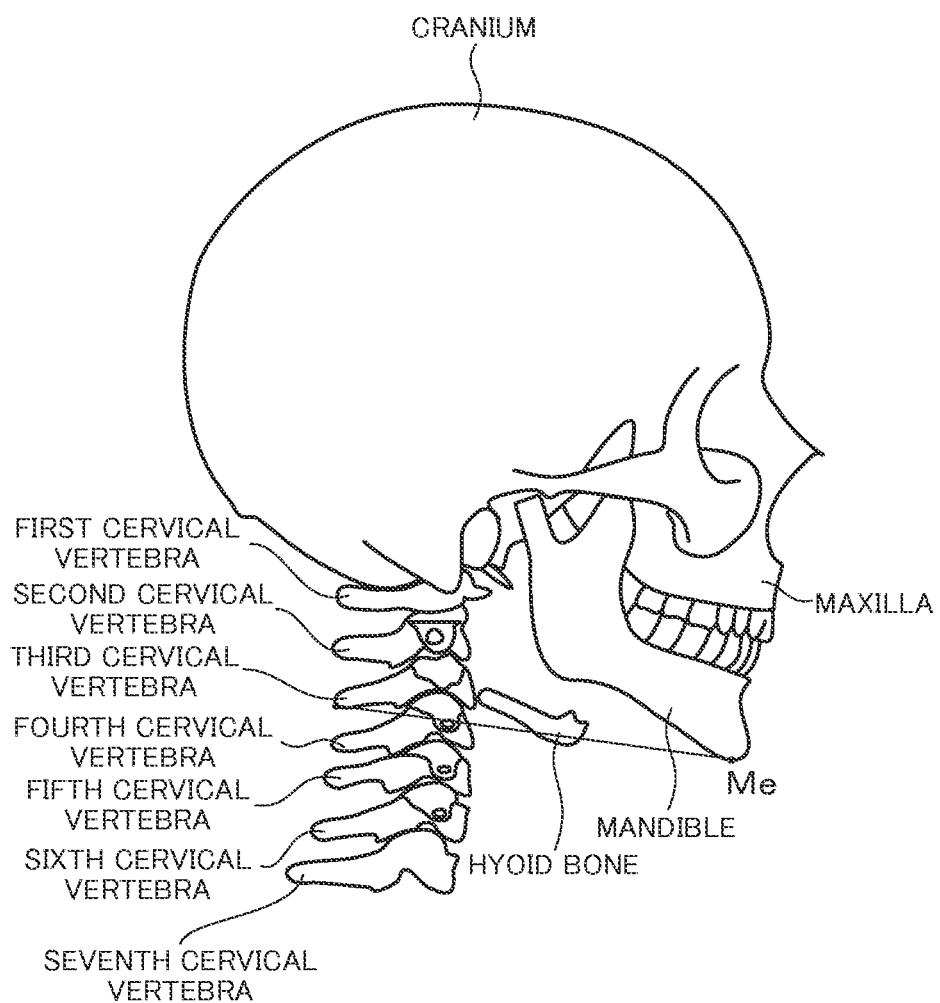
FIG. 108 A schematic drawing for explaining another method of deciding the risk of obstructive sleep apnea syndrome.

FIG. 107 shows an example of the data processor 50. As shown in FIG. 107, the data processor 50 is comprised of an auxiliary storage device 51, a memory 52, a CPU (Central Processing Unit) 53 as a processing part, an input part 54, an output part 55 and an input-output interface 56.

The auxiliary storage device 51 is a device to store various kinds of information. For example, the auxiliary storage device 51 is comprised of a hard disk, a ROM (Read Only Memory), etc. The auxiliary storage device 51 stores a program 111, a compiler 112 and an execution module 113.

The program 111 is a program (source program) describing the processing on the flowcharts shown in FIG. 4, FIG. 7, FIG. 8, FIG. 30, FIG. 33 to FIG. 35, FIG. 50, FIG. 87, FIG. 89, FIG. 91, FIG. 93, FIG. 95, FIG. 97 or FIG. 98. The compiler 112 compiles and links the program 111. The execution module 113 is a module which is compiled and linked by the compiler 112.

The memory 52 is temporary storing means to store various kinds of information, and is comprised of a RAM (Random Access Memory), etc., for example. The CPU 53 executes various types of arithmetic processing such as addition, subtraction, multiplication and division, etc., and plays a role executing the execution module 13 through the memory 52 and the input-output interface 56. The input part 54 is an input device to enter various kinds of execution commands etc. The output part 55 is an output device to output the various kinds of execution results etc. The input-output interface 56 is to mediate the input-output between each composition element of the data processor 50.

Next, the operation of the data processor 50 comprised as described above is explained. First, the compile commands entered from the input part 50 by an operator are stored in the memory 52 through the input-output interface 56. In the memory 52, the program 111 of the auxiliary storage device 51 is compiled and linked by the compiler 112, and the execution module 113 which is a machine language code is generated.

Next, by entering the execution commands from the input part 54 by an operator, the CPU 53 loads the execution module 113 in the memory 52. When the execution module 113 is loaded in the memory 52, by the CPU 53, each processing on the flowcharts shown in FIG. 4, FIG. 7, FIG. 8, FIG. 30, FIG. 33 to FIG. 35, FIG. 50, FIG. 87, FIG. 89, FIG. 91, FIG. 93, FIG. 95, FIG. 97 or FIG. 98 is sequentially called to the CPU 53 from the memory 52, after executing each processing, the execution results are stored in the memory 52. The execution results stored in the memory 52 are output to the output part 55 through the input-output interface 56 by the CPU 53.

Heretofore, embodiments and examples of the present invention have been explained specifically. However, the present invention is not limited to these embodiments and examples, but contemplates various changes and modifications based on the technical idea of the present invention.

For example, numerical numbers, flowcharts, etc. presented in the aforementioned embodiments and examples are only examples, and the different numerical numbers, flowcharts, etc. may be used as necessary. Furthermore, as needed, it may be possible to combine two or more of the methods of deciding the risk of obstructive sleep apnea syndrome or the methods of deciding sinking of the hyoid bone according to the first to the twenty-first embodiments.

Figure 1:
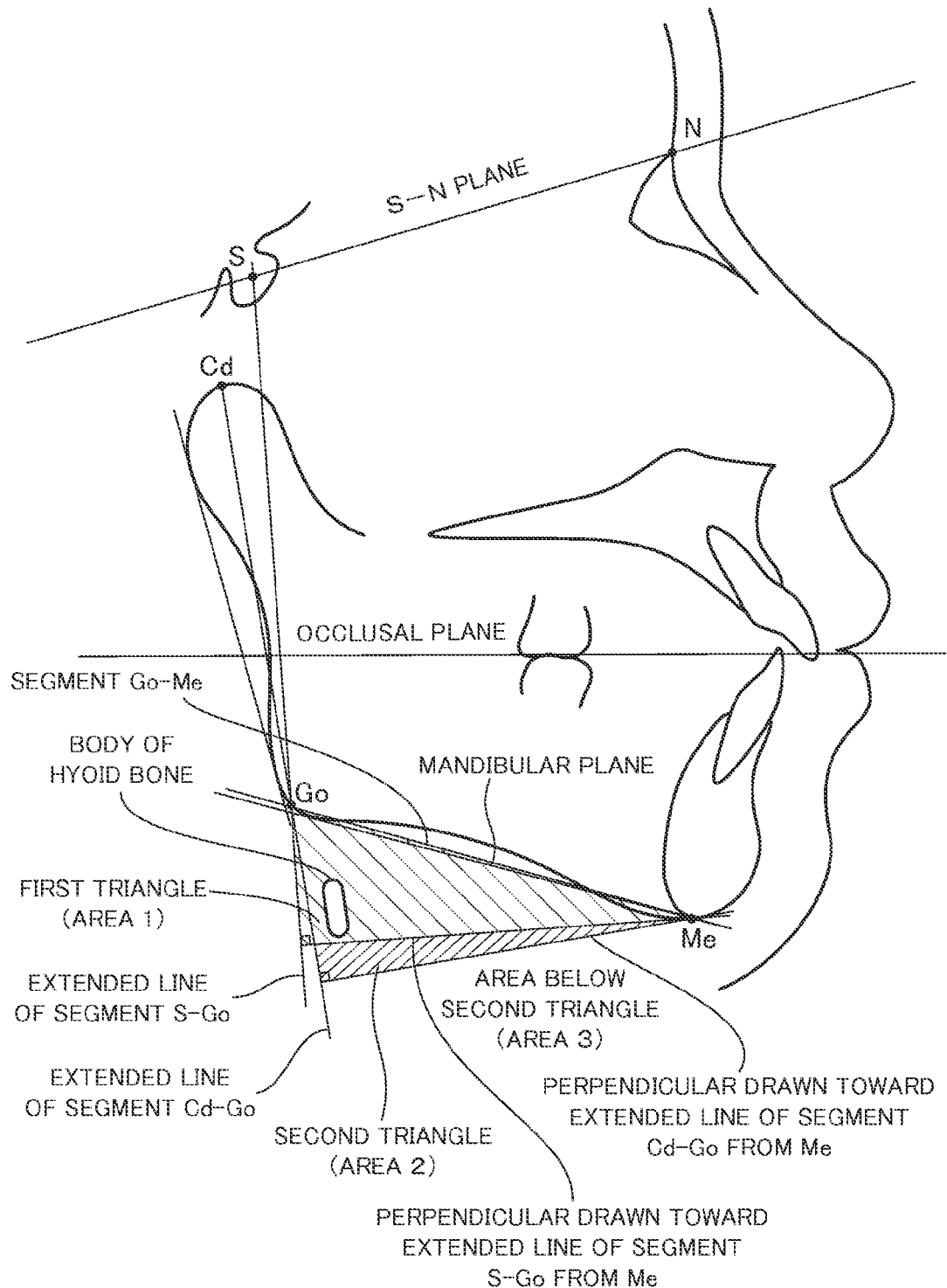
FIG. 1 A schematic drawing for explaining the measured points in the image taken by lateral head and neck radiography, the first triangle and the second triangle.

As needed, it is possible to carry out decision of the risk of obstructive sleep apnea syndrome or decision of sinking of the hyoid bone by detecting the center of the body of the hyoid bone, S, Go, Me and Cd by lateral head and neck radiography of a subject and deciding which area of the area above the perpendicular drawn toward the extended line of the segment S-Go from Me, the area between the perpendicular drawn toward the extended line of the segment S-Go from Me and the perpendicular drawn toward the extended line of the segment Cd-Go from Me and the area below the perpendicular drawn toward the extended line of the segment Cd-Go from Me the detected center of the body of the hyoid bone is included in. Furthermore, instead of Me shown in FIG. 1, it is also possible to use Gn or Pog near to Me.

As needed, when the whole of the body of the hyoid bone, not the center of the body of the hyoid bone, is included in the area above the perpendicular drawn toward the extended line of the segment S-Go from Me, it may be decided that there is no risk of obstructive sleep apnea syndrome, when it is included in the area between the perpendicular drawn toward the extended line of the segment S-Go from Me and the perpendicular drawn toward the extended line of the segment Cd-Go from Me, it may be decided that there is the risk of obstructive sleep apnea syndrome and when it is included in the area below the perpendicular drawn toward the extended line of the segment Cd-Go from Me, it may be decided that the risk of obstructive sleep apnea syndrome is higher.

Depending on circumstances, the center of the body of the hyoid bone, S, Go Me and Cd are detected by lateral head and neck radiography of a subject and when the detected center of the body of the hyoid bone is included in the area above an area between the perpendicular drawn toward the extended line of the segment S-Go from Me and a straight line apart from the perpendicular upward by a small distance d, for example, $0 < d \leq 2$ mm, it may be decided that there is no risk of obstructive sleep apnea syndrome, and when it is included in an area below the straight line, it may be decided that there is the risk of obstructive sleep apnea syndrome. Or, for example, the body of the hyoid bone, S, Go, Me and Cd are detected by lateral head and neck radiography of the subject and when the part of the body of the detected hyoid bone within the predetermined distance from the center of the body of the hyoid bone in the vertical direction or the part of the body within the predetermined distance from the upper edge or the lower edge is included in the area above the perpendicular drawn toward the extended line of the segment S-Go from Me, it may be decided that there is no risk of obstructive sleep apnea syndrome and when it is included in the area below the straight line, it may be decided that there is the risk of obstructive sleep apnea syndrome.

As needed, it may be possible to detect the body of the hyoid bone by methods other than lateral head and neck radiography and obtain the center of the body. For example, it may be possible to detect the body of the hyoid bone by applying ultrasonic wave to the side of the neck of the subject and obtain the center of the body.

As needed, instead of the segment Go-Me, the mandibular plane may be also used. Furthermore, instead of the perpendicular drawn toward the extended line of the segment S-Go from Me or the perpendicular drawn toward the extended line of the segment Cd-Go from Me, it may be possible to use a straight line tilted for the perpendicular drawn toward the extended line of the segment S-Go from Me at the predetermined angle, for example, at an angle within ±5° or a straight line tilted for the perpendicular drawn toward the extended line of the segment Cd-Go from Me at the predetermined angle, for example, at an angle within ±5°. Furthermore, it may be possible to use other segments instead of the segment S-Go or the segment Cd-Go. For example, segments tilted for the segment S-Go or the segment Cd-Go at the predetermined angle, for example, at an angle within ±5° may be used.

Furthermore, as the hyoid bone is generally considered to locate at a height of the same label as the third cervical vertebra of the front neck, as needed, it may be possible to detect the body of the hyoid bone, Me and the cervical vertebrae by lateral head and neck radiography of the subject and draw a straight line (the first straight line) connecting, for example, Me and the end (the rear end) of the spinous process of the third cervical vertebra. And, when the center of the body of the hyoid bone is included in an area above the first straight line, it may be decided that there is no risk of obstructive sleep apnea syndrome, and when it is included in an area below the first straight line, it may be decided that there is the risk of obstructive sleep apnea syndrome. In this case, it may be possible to further draw a straight line (the second straight line) connecting Me and the end (the rear end) of the spinous process of the fourth cervical vertebra. And, when the center of the body of the hyoid bone is included in an area between the first straight line and the second straight line, it may be decided that there is the risk of obstructive sleep apnea syndrome and when it is included in an area below the second straight line, it may be decided that the risk of obstructive sleep apnea syndrome is higher. It is also possible to decide the risk of obstructive sleep apnea syndrome by deciding which area the whole of the body of the hyoid bone, instead of the center of the body of the hyoid bone, belongs to. It may be also possible to use Gn or Pog instead of Me.

Figure 109:
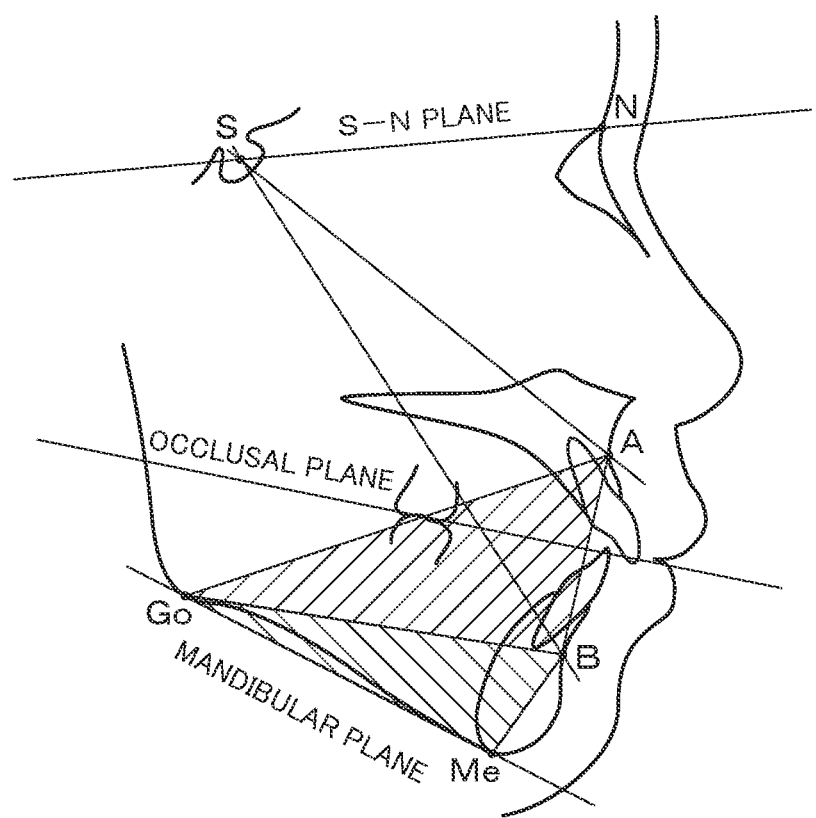
FIG. 109 A schematic drawing for explaining still another method of deciding the risk of obstructive sleep apnea syndrome.

It is well known that the ratio of the mandible occupying the maxilla and mandible of patients of obstructive sleep apnea syndrome tends to be small. Therefore, for example, in FIG. 109, when the area of the triangle GoAB is denoted as $S_1$ and the area of the triangle GoBM is denoted as $S_2$, for example, $(S_1/S_2) \times 100$ may be an index indicating the ratio of the mandible, so it is possible to use it as an index for deciding the risk of obstructive sleep apnea syndrome (OSAS index). It is also possible to use Gn or Pog instead of Me.

As needed, it is also possible to draw a straight line (the first straight line) connecting Me and an arbitrary point on the thyroid cartilage, for example, the rear end of the upper edge of the thyroid cartilage. And, when the center of the body of the hyoid bone is included in an area above the first straight line or it is apart from the first straight line upward more than the predetermined distance, it may be decided that there is no risk of obstructive sleep apnea syndrome, and when it is included in an area below the first straight line or it is not apart from the first straight line upward more than the predetermined distance, it may be decided that there is the risk of obstructive sleep apnea syndrome. Or, it is also possible to draw a straight line (the first straight line) connecting Me and an arbitrary point on the glottis (rima glottidis, vestibular fold and vocal fold). And, when the center of the body of the hyoid bone is included in an area above the first straight line or it is apart from the first straight line upward more than the predetermined distance, it may be decided that there is no risk of obstructive sleep apnea syndrome, and when it is included in an area below the first straight line or it is not apart from the first straight line upward more than the predetermined distance, it may be decided that there is the risk of obstructive sleep apnea syndrome. In these cases, it is possible to decide the risk of obstructive sleep apnea syndrome by deciding which area the whole of the body of the hyoid bone, instead of the center of the body of the hyoid bone, belongs to. It is also possible to use Gn or Pog instead of Me.

Furthermore, the hyoid bone observed by lateral head and neck radiography differs in its tilting angle for the horizontal plane depending on subjects. Therefore, the tilting angle may contribute to decision of the risk of obstructive sleep apnea syndrome. The hyoid bone observed by, for example, posteroanterior head and neck radiography or anteroposterior head and neck radiography may also differ in its tilting angle for the horizontal plane depending on subjects or deviate from the median plane to the right side or the left side. Therefore, the tilting angle or the deviation may also contribute to decision of the risk of obstructive sleep apnea syndrome.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXPLANATION OF REFERENCE NUMERALS

11 X-ray generator
11a X-ray tube
12, 13 Arm
14 Arm control device
15 X-ray detector
16 Reference line
17, 18 Ear rod
19 Head tilt setting device
20 Horizontal plate
21 Head
22 Seal
40 Oral appliance
41 Maxilla part
42 Mandible part
43, 44 Part for accommodating dentition

The invention claimed is:
1. A method of deciding the risk of obstructive sleep apnea syndrome executed by a computer having a program comprising:
a first step of using at least hyoid bone, sella S, gonion Go and menton Me which are detected from an image displayed on a display connected with a computer which is taken by lateral head and neck radiography of a subject and input into the computer, displaying a center of a body or an outline of the whole of the body of the detected hyoid bone, an extended line of the segment S-Go from Me and a perpendicular drawn toward the extended line of the segment S-Go from Me, which are obtained by the computer, on the display, wherein a first triangle formed by the extended line of the segment S-Go, the perpendicular drawn toward the extended line of the segment S-Go from Me and the segment Go-Me obtained by the computer is displayed on the display;

a second step of deciding whether the center of the body or the whole of the body of the detected hyoid bone is included in an area above the perpendicular drawn toward the extended line of the segment S-Go from Me or not, wherein it is decided whether the center of the body or the whole of the body of the detected hyoid bone is included in the inside of the first triangle or not;

a third step of deciding that when the center of the body or the whole of the body of the hyoid bone is included in the area above the perpendicular drawn toward the extended line of the segment S-Go from Me, there is no risk of obstructive sleep apnea syndrome, and when the center of the body or the whole of the body of the hyoid bone is included in an area below the perpendicular drawn toward the extended line of the segment S-Go from Me, there is the risk of obstructive sleep apnea syndrome, wherein it is decided that when the center of the body or the whole of the body of the hyoid bone is included in the inside of the first triangle, there is no risk of obstructive sleep apnea syndrome, and when the center of the body or the whole of the body of the hyoid bone is not included in the first triangle, there is the risk of obstructive sleep apnea syndrome; and a fourth step of outputting a result of decision of the third step.

2. The method of deciding the risk of obstructive sleep apnea syndrome according to claim 1, wherein in the first step, condylion Cd is further detected from the image and the extended line of the segment Cd-Go and a perpendicular drawn toward the extended line of the segment Cd-Go from Me and a second triangle formed by the extended line of the segment Cd-Go, the perpendicular drawn toward the extended line of the segment Cd-Go from Me and the perpendicular drawn toward the extended line of the segment S-Go from Me, which are obtained by the computer, are further displayed on the display; in the second step, it is decided that which area of the inside of the first triangle, the inside of the second triangle and an area below the second triangle the center of the body or the whole of the body of the detected hyoid bone is included in; and in the third step, it is decided that when the center of the body or the whole of the body of the hyoid bone is included in the inside of the first triangle, there is no risk of obstructive sleep apnea syndrome, and when the center of the body or the whole of the body of the hyoid bone is included in the inside of the second triangle or the area below the second triangle, there is the risk of obstructive sleep apnea syndrome.

3. The method of deciding the risk of obstructive sleep apnea syndrome according to claim 1, wherein the lateral head and neck radiography is carried out by setting the tilt of the head of the subject in the front-rear direction so that the Frankfort plane of the head is parallel to the floor surface.

4. A method of deciding sinking of the hyoid bone executed by a computer having a program comprising:

a first step of using at least hyoid bone, sella S, gonion Go and menton Me which are detected from an image displayed on a display connected with a computer which is taken by lateral head and neck radiography of a subject and input into the computer, displaying a center of a body or the outline of the whole of the body of the detected hyoid bone, the extended line of the segment S-Go from Me and a perpendicular drawn toward the extended line of the segment S-Go from Me obtained by the computer on the display, wherein a first triangle formed by the extended line of the segment S-Go, the perpendicular drawn toward the extended line of the segment S-Go from Me and the segment Go-Me is displayed on the display;

a second step of deciding whether the center of the body or the whole of the body of the detected hyoid bone is included in an area above the perpendicular drawn toward the extended line of the segment S-Go from Me or not, wherein it is decided whether the center of the body or the whole of the body of the detected hyoid bone is included in the inside of the first triangle or not; and a third step of outputting the result of decision of the second step.

5. The method of deciding sinking of the hyoid bone according to claim 4, wherein in the first step, condylion Cd is further detected from the image and the extended line of the segment Cd-Go, a perpendicular drawn toward the extended line of the segment Cd-Go from Me and a second triangle formed by the extended line of the segment Cd-Go, the perpendicular drawn toward the extended line of the segment Cd-Go from Me and the perpendicular drawn toward the extended line of the segment S-Go from Me, which are obtained by the computer, are further displayed on the display; and in the second step, it is decided that which area of the inside of the first triangle, the inside of the second triangle and an area below the second triangle the center of the body or the whole of the body of the detected hyoid bone is included in.

6. The method of deciding sinking of the hyoid bone according to claim 4, wherein in the first step, condylion Cd is further detected from the image and the extended line of the segment Cd-Go and a perpendicular drawn toward the extended line of the segment Cd-Go from Me, which are obtained by the computer, are further displayed on the display; and in the second step, it is decided that which area of the area above the perpendicular drawn toward the extended line of the segment S-Go from Me, an area between the perpendicular drawn toward the extended line of the segment S-Go from Me and the perpendicular drawn toward the extended line of the segment Cd-Go from Me and an area below the perpendicular drawn toward the extended line of the segment Cd-Go from Me the center of the body or the whole of the body of the detected hyoid bone is included in.

7. A program for executing by a computer the method of deciding the risk of obstructive sleep apnea syndrome according to claim 1.

8. An x-ray diagnostic system comprising a computer having a program according to claim 7.

9. A program for executing by a computer the method of deciding sinking of the hyoid bone according to claim 4.

10. An x-ray diagnostic system comprising a computer having a program according to claim 9.

* * * * *